United States Patent
Bonfanti et al.

(10) Patent No.: US 9,556,176 B2
(45) Date of Patent: Jan. 31, 2017

(54) PURINE DERIVATIVES FOR THE TREATMENT OF VIRAL INFECTIONS

(71) Applicant: Janssen R&D Ireland, Little Island, Co Cork (IE)

(72) Inventors: Jean-François Bonfanti, Andé (FR); Frédéric Marc Maurice Doublet, Isneauville (FR); Werner Embrechts, Beerse (BE); Jérôme Michel Claude Fortin, Igoville (FR); David Craig McGowan, Brussels (BE); Philippe Muller, Andé (FR); Pierre Jean-Marie Bernard Raboisson, Rosieres (BE)

(73) Assignee: JANSSEN SCIENCES IRELAND UC, Little Island, Co. Cork (IE)

( * ) Notice: Subject to any disclaimer, the term of this patent is extended or adjusted under 35 U.S.C. 154(b) by 0 days.

(21) Appl. No.: 14/357,495

(22) PCT Filed: Nov. 8, 2012

(86) PCT No.: PCT/EP2012/072090
§ 371 (c)(1),
(2) Date: May 9, 2014

(87) PCT Pub. No.: WO2013/068438
PCT Pub. Date: May 16, 2013

(65) Prior Publication Data
US 2014/0323441 A1    Oct. 30, 2014

(30) Foreign Application Priority Data
Nov. 9, 2011 (EP) .................................. 11188511

(51) Int. Cl.
C07D 473/34 (2006.01)
C07D 473/16 (2006.01)
C07D 519/00 (2006.01)
C07F 9/6561 (2006.01)

(52) U.S. Cl.
CPC ........... *C07D 473/34* (2013.01); *C07D 473/16* (2013.01); *C07D 519/00* (2013.01); *C07F 9/65616* (2013.01)

(58) Field of Classification Search
None
See application file for complete search history.

(56) References Cited

U.S. PATENT DOCUMENTS

| | | | |
|---|---|---|---|
| 6,028,076 A | 2/2000 | Hirota et al. | |
| 6,376,501 B1 * | 4/2002 | Isobe | A61K 31/52 |
| | | | 514/263.37 |
| 7,498,409 B2 | 3/2009 | Vlach et al. | |
| 2007/0225303 A1 | 9/2007 | Ogita et al. | |
| 2014/0148433 A1 | 5/2014 | Follmann et al. | |

FOREIGN PATENT DOCUMENTS

| | | |
|---|---|---|
| CN | 101 784 548 A | 7/2010 |
| EP | 0 882 727 A1 | 9/1998 |
| EP | 1 939 198 A1 | 7/2008 |
| EP | 2 138 497 A1 | 12/2009 |
| JP | 2009-528989 A | 8/2009 |
| JP | 2010-522151 A | 7/2010 |
| JP | 2010-532353 A | 10/2010 |
| WO | WO 98/01448 A1 | 1/1998 |
| WO | WO 99/32122 A1 | 7/1999 |
| WO | WO 99/28321 A1 | 10/1999 |
| WO | WO 2005/092892 A1 | 10/2005 |
| WO | WO 2006117670 A1 | 11/2006 |
| WO | WO 2007/034881 A1 | 3/2007 |
| WO | WO 2007/093901 A1 | 8/2007 |
| WO | WO 2008/114008 A1 | 9/2008 |
| WO | WO 2009/005687 A1 | 1/2009 |
| WO | WO 2009/067081 A1 | 5/2009 |
| WO | WO 2008/114819 A1 | 9/2009 |
| WO | WO 2011/049825 A1 | 4/2011 |

OTHER PUBLICATIONS

Hoffmann J.A. "The Immune Response of *Drosophila*" Nature 2003 vol. 426 pp. 33-38.
Isobe et al "Synthesis and Structure-Activity Relationships of 2-Substituted-8-Hydroxyadenine Derivatives As Orally Available Interferon Inducers Without Emetic Side Effects" Bioorganic & Medicinal Chemistry 2003 vol. 11 pp. 3641-3647.
Krieger et al "Enhancement of Hepatitis C Virus RNA Replication by Cell Culture-Adaptive Mutations" Journal of Virology 2001 vol. 75 pp. 4614-4624.
Kurimoto et al "Synthesis and Structure—Activity Relationships of 2-Amino-8-Hydroxyadenines as Orally Active Interferon Inducing Agents" Bioorg Med Chem 2003 vol. 11 pp. 5501-5508.
Liu et al "Synthesis and Biological Activity of 3- and 5-Amino Derivatives Ofpyridine-2-Carboxaldehyde Thiosemicarbazone" J. Med Chem 1996 vol. 39(13) pp. 2586-2593.
Lohmann et al "Viral and Cellular Determinants of Hepatitis C Virus RNA Replication in Cell Culture" Journal of Virology 2003 vol. 77 pp. 3007-3019.
Lohmann et al "Replication of Subgenomic Hepatitis C Virus RNAS in a Hepatoma Cell Line" Science 1999 vol. 285 pp. 110-113.
Musmuca et al "Small-Molecule Interferon Inducers. Toward the Comprehension of the Molecular Determinants Through Ligand-Based Approaches" J. Chem Inf Model. 2009 vol. 49 pp. 1777-1786.
Tran Al "Design and Optimization of Orally Active TLR7 Agonists for the Treatment of Hepatitis C Virus Infection" Bioorganic & Medicinal Chemistry Letters 2011 vol. 21 pp. 2389-2393.
International Search Report for International Publication No. PCT/EP2012/072090 Dated Dec. 17, 2012 4 Pages.

* cited by examiner

*Primary Examiner* — Kendra D Carter
*Assistant Examiner* — Taina D Matos Negron

(57) ABSTRACT

The present invention relates to purine derivatives of formula (I), processes for their preparation, pharmaceutical compositions, and their use in treating viral infections.

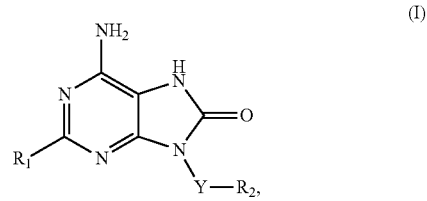

4 Claims, No Drawings

PURINE DERIVATIVES FOR THE TREATMENT OF VIRAL INFECTIONS

CROSS REFERENCE TO RELATED APPLICATION

This application is a national stage of PCT Application PCT/EP2012/072090, filed on Nov. 8, 2012, which claims priority to application EP11188511.7, filed on Nov. 9, 2011.

The current invention relates to purine derivatives, processes for their preparation, pharmaceutical compositions, and their use in treating viral infections.

The present invention relates to the use of purine derivatives in the treatment of viral infections, immune or inflammatory disorders, whereby the modulation, or agonism, of toll-like-receptors (TLRs) is involved. Toll-Like Receptors are primary transmembrane proteins characterized by an extracellular leucine rich domain and a cytoplasmic extension that contains a conserved region. The innate immune system can recognize pathogen-associated molecular patterns via these TLRs expressed on the cell surface of certain types of immune cells. Recognition of foreign pathogens activates the production of cytokines and upregulation of co-stimulatory molecules on phagocytes. This leads to the modulation of T cell behaviour.

It has been estimated that most mammalian species have between ten and fifteen types of Toll-like receptors. Thirteen TLRs (named TLR1 to TLR13) have been identified in humans and mice together, and equivalent forms of many of these have been found in other mammalian species. However, equivalents of certain TLR found in humans are not present in all mammals. For example, a gene coding for a protein analogous to TLR10 in humans is present in mice, but appears to have been damaged at some point in the past by a retrovirus. On the other hand, mice express TLRs 11, 12, and 13, none of which are represented in humans. Other mammals may express TLRs which are not found in humans. Other non-mammalian species may have TLRs distinct from mammals, as demonstrated by TLR14, which is found in the Takifugu pufferfish. This may complicate the process of using experimental animals as models of human innate immunity.

For a review on toll-like receptors see for instance the following journal article: Hoffmann, J. A., Nature, 426, p 33-38, 2003.

Compounds indicating activity on Toll-Like receptors have been previously described such as purine derivatives in WO 2006/117670, adenine derivatives in WO 98/01448 and WO 99/28321, and pyrimidines in WO 2009/067081.

However, there exists a strong need for novel Toll-Like receptor modulators having preferred selectivity, higher potency, higher metabolic stability, higher solubility and an improved safety profile compared to the compounds of the prior art.

In accordance with the present invention compounds of formula (I) are provided

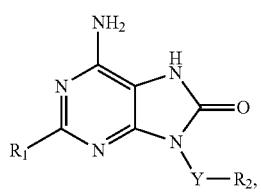

(I)

or a pharmaceutically acceptable salt, solvate or polymorph thereof, wherein
Y is $(C_{1-4})$alkylene,
$R_1$ is a heteroaryl[1] and
$R_2$ an aryl[2] or a heterocyclyl.

The term heteroaryl[1] means imidazolyl, pyridyl, pyrimidyl, pyrrolyl, pyrazolyl, furyl, oxazolyl, oxadiazolyl, isoxazolyl, pyrazinyl or thiazolyl. Heteroaryl[1] is optionally substituted by one or more substituents independently selected from hydroxyl, $C_{1-6}$alkyl, $C_{1-4}$ alkoxy, trifluoromethyl, $C_{3-6}$ cycloalkyl, phenyl, halogen, hydroxyl-$C_{1-4}$ alkyl, $C_{1-4}$-alkoxy-$C_{1-4}$-alkyl-, or $C_{1-4}$alkyl-diethoxyphosphoryl.

The term aryl[2] includes phenyl, naphtyl, anthracenyl and phenanthrenyl and is preferably phenyl. Aryl[2] is optionally substituted by one or more substituents independently selected from hydroxyl, $C_{1-6}$ alkyl, $C_{1-4}$ alkoxy, trifluoromethyl, $CO_2R_3$, $R_4R_5N$—$C_{1-4}$-alkyl-, halogen, hydroxyl-$C_{1-4}$ alkyl-, $NR_6R_7$, $C(O)R_6$, $C(O)NR_6R_7$, $C_{1-4}$alkyl-diethoxyphosphoryl or $C_{1-4}$alkyl-phosphonic acid.

$R_3$ is selected from H and $C_{1-6}$ alkyl.

$R_4$ and $R_5$ taken together with the nitrogen, to which they are both attached, form a heterocycle selected from the group consisting of:

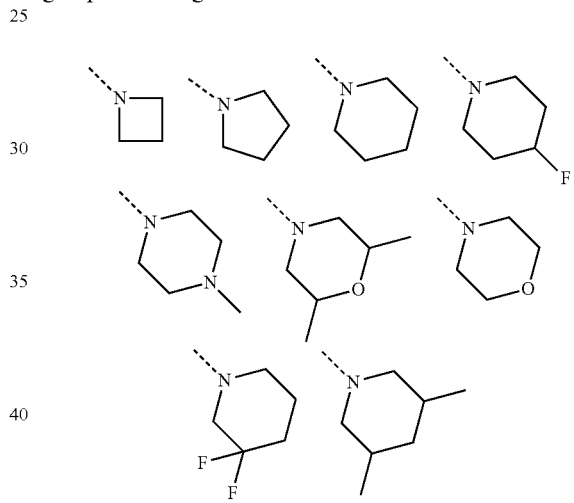

$R_6$ and $R_7$ are each independently selected from H, $C_{1-6}$-alkyl or $C_{1-4}$alkoxy.

The term "heterocyclyl" refers to tetrahydropyran and heteroaryl[2].

The term heteroaryl[2] includes pyridyl, tetrahydroisoquinolinyl, imidazopyridinyl, quinolinyl, isoquinolinyl, pyrazinyl, pyrimidyl, naphtyridinyl, pyridazinyl, benzimidazolyl, benzothiazolyl, pyrazolyl, thiazolyl, imidazolyl, indazolyl. Heteroaryl[2] is optionally substituted by one or more substituents independently selected from halogen, hydroxyl, $C_{1-6}$alkyl, $C_{1-4}$alkoxy, oxy-$C_{1-4}$alkylamine or pyrrolidinylmethanone.

In a further embodiment the current invention encompasses a compound of formula (I) wherein $R_1$ is selected from the group comprising an imidazolyl, a pyrazolyl or a pyridinyl each of which is optionally substituted by one or more substituents independently selected from halogen, hydroxyl, $C_{1-6}$ alkyl, $C_{1-4}$alkoxy or $C_{3-6}$ cycloalkyl.

Preferred compounds according to the invention are compounds listed in Table 1 and Table 2 respectively under the heading of the following numbers: 1, 4, 9, 23, 24, 25, 26, 35, 36, 48, 49, 50, 51 and 54.

Furthermore to the invention belongs a pharmaceutical composition comprising a compound of formula (I) or a pharmaceutically acceptable salt, solvate or polymorph thereof together with one or more pharmaceutically acceptable excipients, diluents or carriers.

Part of the invention is also a compound of formula (I) or a pharmaceutically acceptable salt, solvate or polymorph thereof or a pharmaceutical composition above mentioned for use as a medicament.

The invention also related to a compound of formula (I) or a pharmaceutically acceptable salt, solvate or polymorph thereof or a pharmaceutical composition above mentioned for use in the treatment of a disorder in which the modulation of TLR7 is involved.

The term "alkyl" refers to a straight-chain or branched-chain saturated aliphatic hydrocarbon containing the specified number of carbon atoms.

The term "halogen" refers to fluorine, chlorine, bromine or iodine.

The term "cycloalkyl" refers to a carbocyclic ring containing the specified number of carbon atoms.

The term "alkoxy" refers to an alkyl (carbon and hydrogen chain) group singular bonded to oxygen like for instance a methoxy group or ethoxy group.

Pharmaceutically acceptable salts of the compounds of formula (I) include the acid addition and base salts thereof. Suitable acid addition salts are formed from acids which form non-toxic salts. Suitable base salts are formed from bases which form non-toxic salts.

The compounds of the invention may also exist in unsolvated and solvated forms. The term "solvate" is used herein to describe a molecular complex comprising the compound of the invention and one or more pharmaceutically acceptable solvent molecules, for example, ethanol.

The term "polymorph" refers to the ability of the compound of the invention to exist in more than one form or crystal structure.

The compounds of the invention can be present in a so-called "tautomer(s)" formation referring to isomers of organic compounds that readily interconvert by a chemical reaction called tautomerization. This reaction results in the formal migration of a hydrogen atom or proton, accompanied by a switch of a single bond and adjacent double bond.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral, rectal, or percutaneous administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

Those of skill in the treatment of infectious diseases will be able to determine the effective amount from the test results presented hereinafter. In general it is contemplated that an effective daily amount would be from 0.01 mg/kg to 50 mg/kg body weight, more preferably from 0.1 mg/kg to 10 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

EXPERIMENTAL SECTION

Overall Scheme in the Preparation of Final Compounds

Method 1

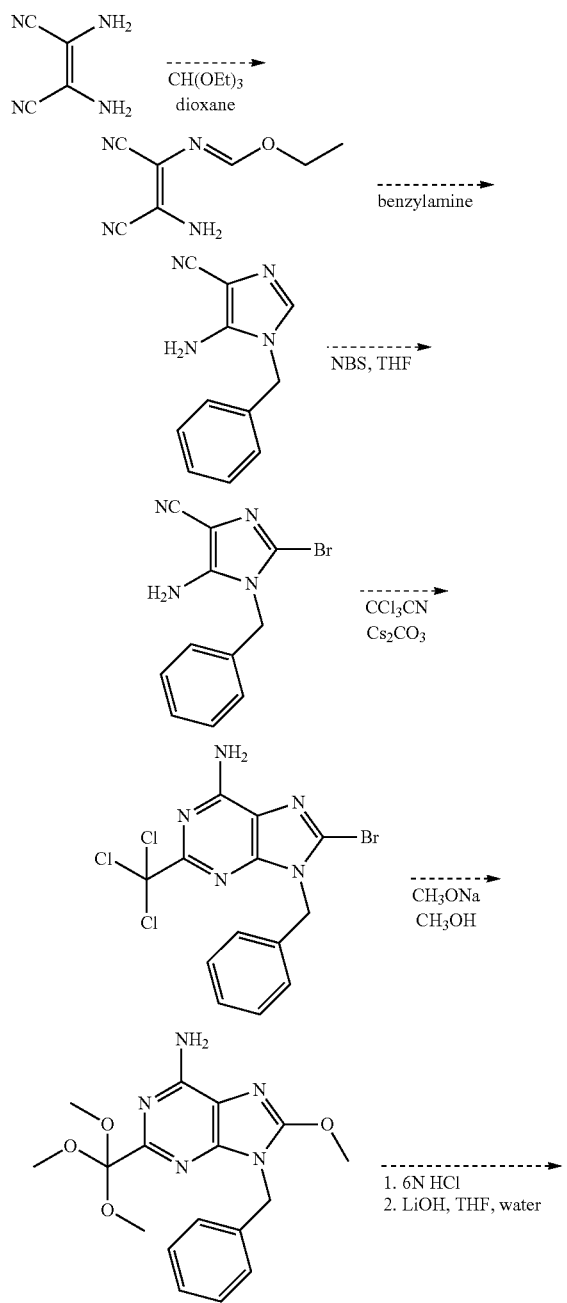

coupling agent

Preparation of Intermediate A-1

Diaminomaleononitrile (6 g, 55 mmol) and triethylorthoformate (9.2 mL, 55 mmol) were combined in 1,4-dioxane (95 mL) and heated under distillation conditions until 65 mL of 1,4-dioxane/ethanol had been collected. The reaction mixture was cooled to room temperature and the solvent evaporated in vacuo. The residue was purified by column chromatography using a petroleum ether to 25% ethyl acetate in petroleum ether gradient to give 5 g of A-1.

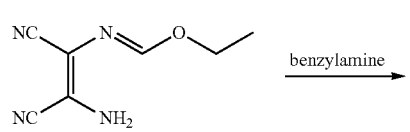

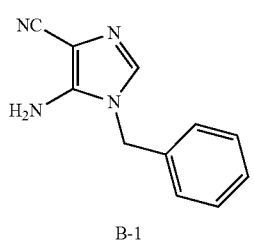

Preparation of Intermediate B-1

Benzylamine (2.86 mL, 26.3 mmol) was added dropwise to a solution of A-1 (4.1 g, 25 mmol) and aniline hydrochloride (50 mg) in ethanol (80 mL), stirring at 10° C. The reaction mixture stirred at room temperature for 18 hours. The reaction mixture was added dropwise to 1M NaOH (50 mL), stirring at 10° C., and the resultant suspension stirred at room temperature for 18 hours. The solid was collected by filtration, washed with water and dried in vacuo. The title compound was obtained as off white solid, B-1 (4 g).

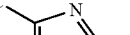

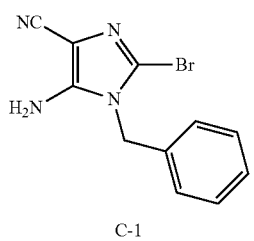

Preparation of Intermediate C-1

N-bromosuccinimide (4 g, 22 mmol) was added portionwise to a suspension of B-1 (4 g, 20 mmol) in THF (50 mL) and the reaction mixture stirred at room temperature for 10 minutes. The solvent was evaporated in vacuo and the residue extracted from a saturated aqueous solution of NaHCO₃ (50 mL) with ethyl acetate (300 mL), dried over Na₂SO₄, the solids were removed by filtration, and the solvents of the filtrate were removed under reduced pressure. The residue was purified via column chromatography using a dichloromethane to 5% methanol in dichloromethane gradient. The best fractions were pooled, the solvents were removed under reduced pressure to afford a pink solid, C-1 (3 g).

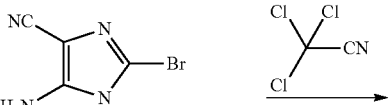

Preparation of Intermediate D-1

Trichloroacetonitrile (4.8 g, 17.3 mmol) was added to a suspension of C-1 (4 g, 14.4 mmol) and Cs₂CO₃ (9.4 g, 29 mmol) in toluene (50 mL) and the reaction mixture was stirred at room temperature for 48 hours. The mixture was poured into water (100 mL) and extracted with ethyl acetate (3×50 mL), dried over Na₂SO₄, the solids were removed by filtration, and the filtrate was concentrated in vacuo. The residue was suspended in ethanol (20 mL) and stirred at room temperature for 2 hours. The resultant solid was collected by filtration and washed with methanol to yield an off white solid, D-1 (2.7 g).

-continued

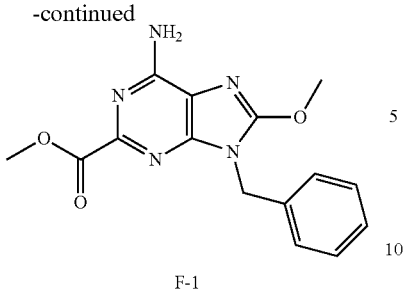

F-1

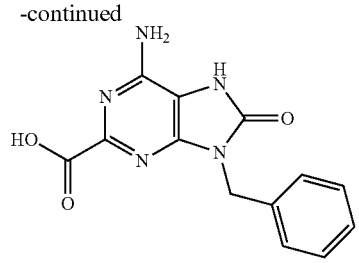

H-1

Preparation of Intermediate F-1

Sodium methoxide (2.4 g, 0.06 mol) was added to a suspension of D-1 (5 g, 12 mmol) in methanol (100 mL) and the reaction mixture was heated at reflux for 16 hours. The mixture was cooled in an ice-water bath and quenched with water. The methanol was evaporated in vacuo and the residue was extracted with ethyl acetate. The organic layer was dried and concentrated to afford F-1 (4.6 g, crude).

Preparation of Intermediate H-1

2N NaOH (aq.) was added to a solution of G-1 (1 g, 3.34 mmol) in methanol (50 mL) and the reaction mixture was stirred at room temperature for 2 hours. Methanol was removed under reduced pressure and the reaction mixture was acidified to pH 2 with 2N HCl (aq). The resultant precipitate was collected by filtration and washed with water to afford H-1 (0.95 g).

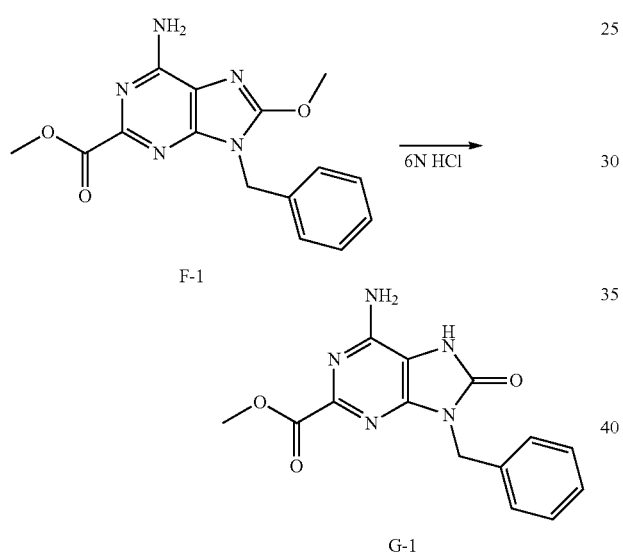

Preparation of Intermediate G-1

Intermediate F-1 (4.6 g, 15 mmol) was suspended in 6N HCl (aq.) (75 mL) and the reaction mixture was stirred for 32 hours at room temperature. The mixture was neutralized with ammonia and the resultant precipitate was collected by filtration and washed with water to afford G-1 (3.2 g).

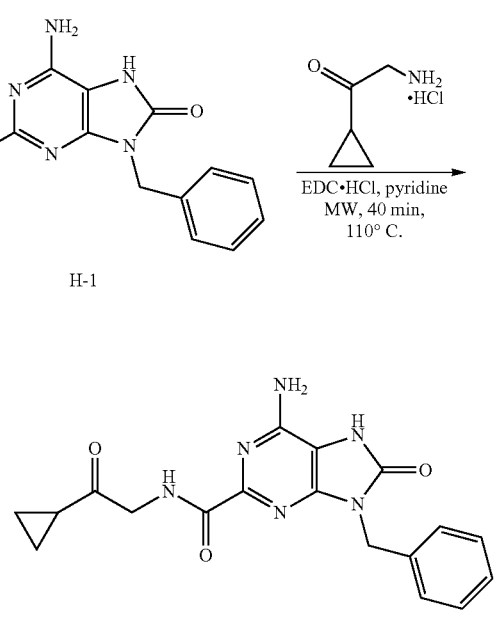

Preparation of Intermediate I-1

A mixture of H-1 (500 mg, 1.4 mmol), Aminoketone 2 (284 mg, 1.6 mmol) and EDCI (460 mg, 2.4 mmol) in pyridine (10 mL) was heated in the microwave to 110 degrees C. for 0.5 hour. The mixture was concentrated to give the crude product which was washed with acetonitrile (10 mL) and cold water to give the intermediate product I-1, as an off-white solid (0.5 g).

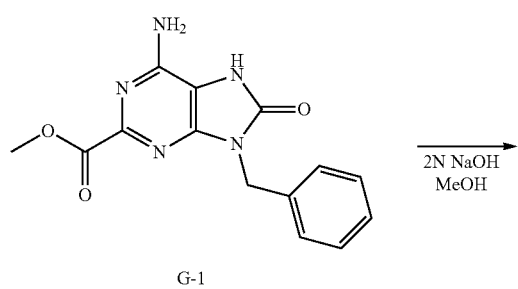

Compound 1

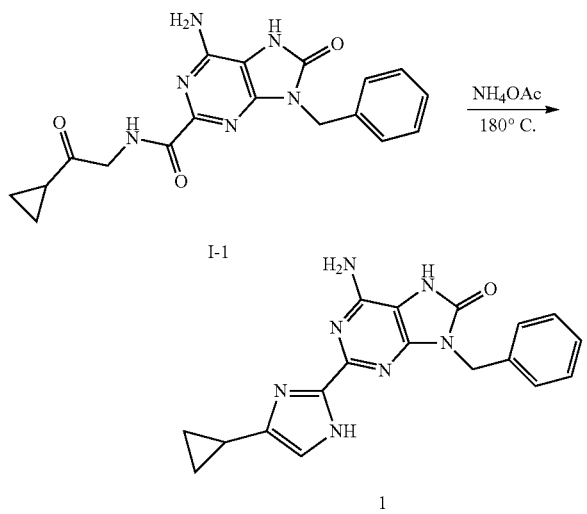

NH$_4$OAc (5 g) was added to a vial and heated in an oil bath until melted. Then I-1 (100 mg) was added and the reaction mixture was heated in the microwave for 1 hour at 180° C. The mixture was poured into water and extracted with a mixed organic solvent (dichloromethane:isopropanol 3:1, 2×60 mL), dried and concentrated. The crude product was purified by preparative HPLC to afford a yellow solid, 1 (105 mg).

Compound 2

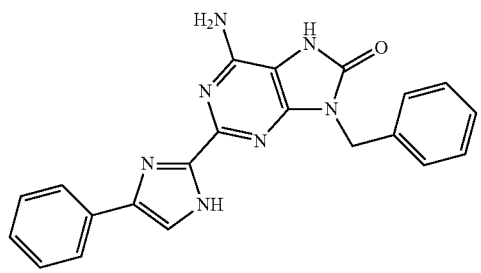

Compound 2 was synthesized according to the procedure to synthesize compound 1 (230 mg).

Compound 3

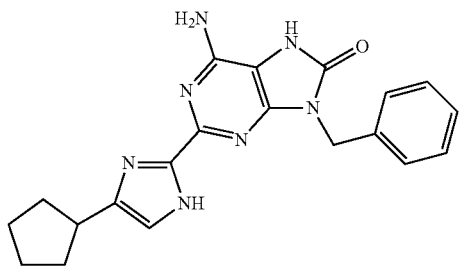

Compound 3 was synthesized according to the procedure to synthesize compound 1 (205 mg).

General Procedure for the Preparation of Aminoketones.

General Chemical Scheme:

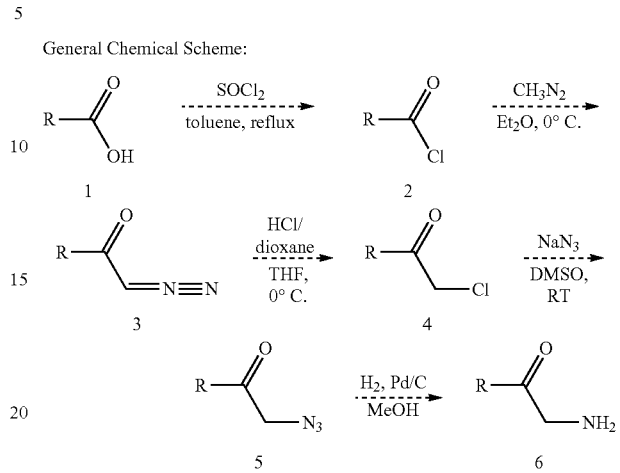

A carboxylic acid (1) is converted to the corresponding acid chloride 2 via thionyl chloride. It is also possible to employ other chlorinating agents, for example oxalyl chloride or phosphorous oxychloride). The acid chloride (2) is treated with diazomethane at lower temperature to afford a diazoketone (3). Diazoketone (3) is converted to its alfa-chloroketone (4) via addition of hydrochloric acid at low temperature. The chlorine of the alfa-chloroketone (4) is displaced by an azide, from an appropriate azide source like sodium azide, in the presence of, usually, a dipolar aprotic solvent, for example DMSO.

Preparation of Aminoketone 1

Reaction scheme:

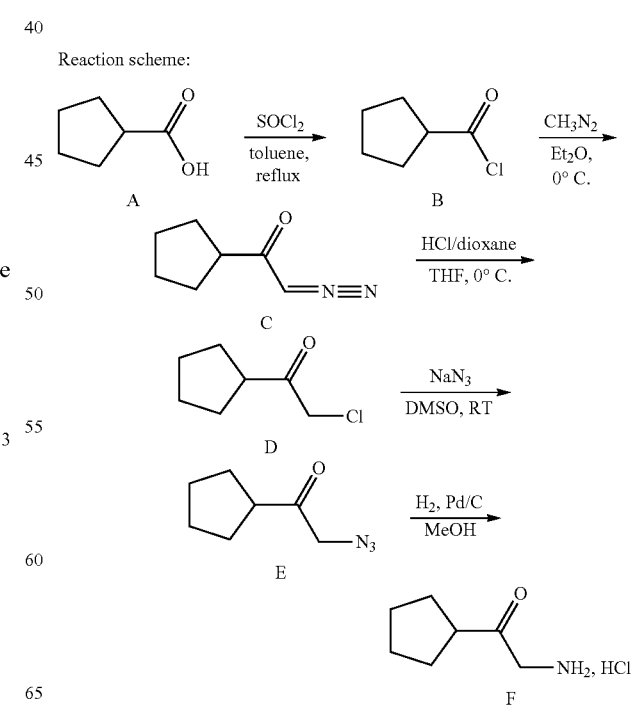

Step 1.

To a solution of A (15 g, 0.13 mol) in toluene (50 mL) was added SOCl$_2$ (15 mL). The reaction mixture was refluxed for 3 h. Toluene was removed under reduced pressure. The acid chloride product was obtained as a brown liquid (16 g) and used in the next step directly.

Step 2.

To a solution of B (16 g, 0.12 mol) in diethylether (100 mL) was added CH$_2$N$_2$ (200 mL) at 0° C. The reaction mixture was stirred for 2 h at this temperature. The ether was removed in vacuo at room temperature. The product was purified by flash chromatography (silica gel, eluent: petroleum ether:ethyl acetate 10:1) to give C (12 g).

$^1$H NMR (CDCl$_3$, 400 MHz): δ (ppm) 5.18 (br. s., 1H), 2.65 (br. s., 1H), 1.45-1.81 (m, 8H)).

Step 3.

To a solution of C (12 g, 0.096 mol) in THF (65 mL) was added 4N HCl/dioxane dropwise at 0° C. The reaction was monitored by TLC. The reaction was neutralized with NaHCO$_3$ (sat. aq.). The mixture was extracted with ethyl acetate (2×150 mL), dried and concentrated to give D (11 g). This product was used to next step immediately.

$^1$H NMR (CDCl$_3$, 400 MHz): δ (ppm) 4.10 (s, 2H), 3.04 (quin, J=7.3 Hz, 1H), 1.54-1.87 (m, 8H)

Step 4.

To a solution of D (7.3 g, 0.05 mol) in DMSO (30 mL) was added NaN$_3$ (3.9 g, 0.06 mol). The reaction was stirred for overnight and monitored by TLC. The reaction was poured into water (50 mL) and extracted with ethyl acetate (2×100 mL), dried over sodium sulfate, the solids were removed by filtration and the solvents of the filtrate were removed under reduced pressure. The crude product was purified by silica gel chromatography using a petroleum ether to ethyl acetate gradient to afford E (5.28 g).

$^1$H NMR (CDCl$_3$, 400 MHz): δ (ppm) 3.93 (s, 2H), 2.83 (quin, J=7.3 Hz, 1H), 1.56-1.84 (m, 8H)

Step 5.

A mixture of E (3.28 g, 0.02 mol), conc. HCl (1.8 mL, 0.02 mol) and 1 g Pd/C (10%) in 30 mL of methanol was stirred for overnight under 50 psi of hydrogen atmosphere. The reaction mixture was filtered and concentrated to give Aminoketone-1 (2 g).

$^1$H NMR (MeOD, 400 MHz): δ (ppm) 4.03 (s, 2H), 3.01-3.12 (quin, J=7.3 Hz, 1H), 1.67-1.98 (m, 8H)

Aminoketone-2

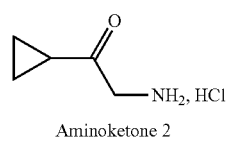

Aminoketone 2

Aminoketone-2 was prepared according to the procedure to prepare Aminoketone-1.

Aminoketone 3

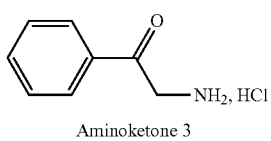

Aminoketone 3

Aminoketone-3 was prepared according to the procedure to prepare Aminoketone-1.

Overall Scheme in the Preparation of Final Products

Method 2

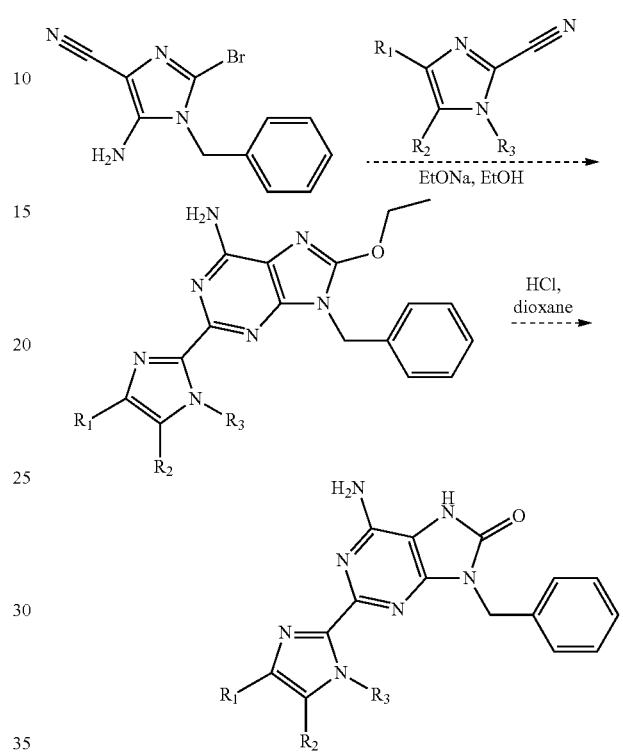

Preparation of Compound 4

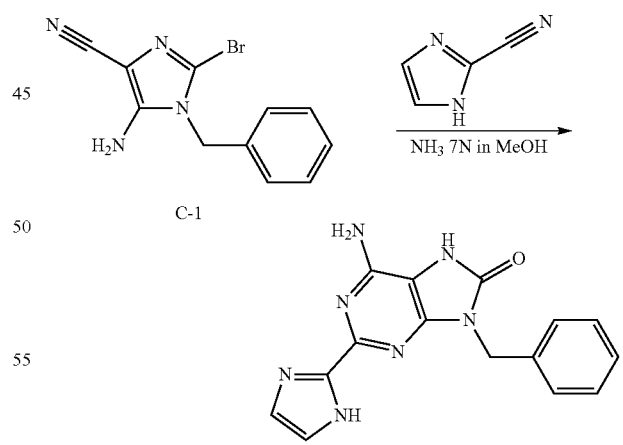

A mixture of C-1 (1.6 g, 5.78 mmol) (its synthesis as such is described in WO20060117670 on pages 59-60: "Preparation 6, 7 and 8" respectively to obtain 5 Amino-1-benzyl-2-bromo-1H-imidazole-4-carbonitrile) and 2-cyano-imidazole (592 mg, 6.35 mmol) in NH$_3$/MeOH (7N) (60 mL) were stirred at 140° C. for 48 hours in a pressure vessel reactor.

The solvent was evaporated. The crude compound was purified by column chromatography over silica gel column (15-40 μm, 40 g), in DCM/MeOH/NH₄OH 97/3/0.5→95/5/0.5) to give compound 4 (78 mg, 4.4% yield).

Alternative Synthesis of Compound 1

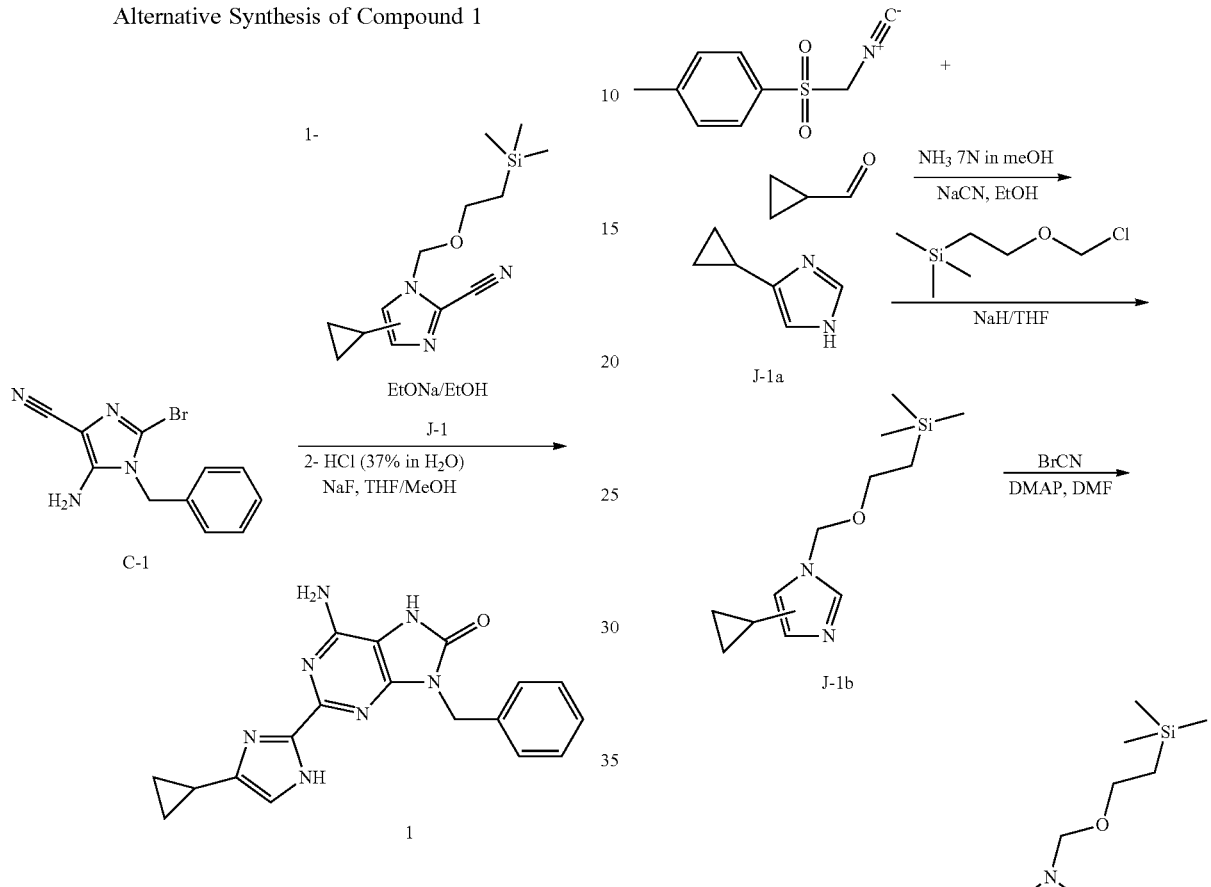

Step 1:

EtONa (904 mg; 13.3 mmol) was added to a solution of 2-cyano-imidazole I-1 (0.7 g; 2.66 mmol) and intermediate C-1 (736 mg; 2.66 mmol) in EtOH (30 mL). The mixture was stirred at 90° C. for 16 h. The solvent was removed under reduced pressure. The crude was purified by preparative LC (irregular SiOH 45 g Merck, mobile phase 97/3/0.1 to 95/5/0.5) to give 0.51 g of the SEM-protected ethoxy intermediate as a lightly yellow solid (38% yield).

HPLC Rt (min)=7.45; MS M+ (H⁺): 506 method (v2003v2002)

Step 2:

NaF (170 mg; 4.05 mmol) was added to a solution of SEM-protected ethoxy intermediate (0.41 g; 0.811 mmol) in THF (28 mL), HCl (37% in H₂O) (28 mL) and MeOH (10 mL). The mixture was stirred at 40° C. for 16 h. The mixture was cooled to RT and a 10% solution of K₂CO₃ was added until the pH of the solution was basic. The aqueous layer was saturated with K₂CO₃ powder and the product was extracted with DCM/MeOH (5%) (3 times). The combined organic layers were dried over MgSO₄, filtered and the solvent was removed under reduced pressure. The crude was purified by preparative LC (irregular SiOH 15-40 μm, mobile phase DCM/MeOH/NH₃aq 95/5/0.5 to 90/10/0.5) to give 120 mg of compound 1 as a white powder (43% yield).

Synthesis of the 2-cyano-imidazole Intermediates

Synthesis of intermediate J-1

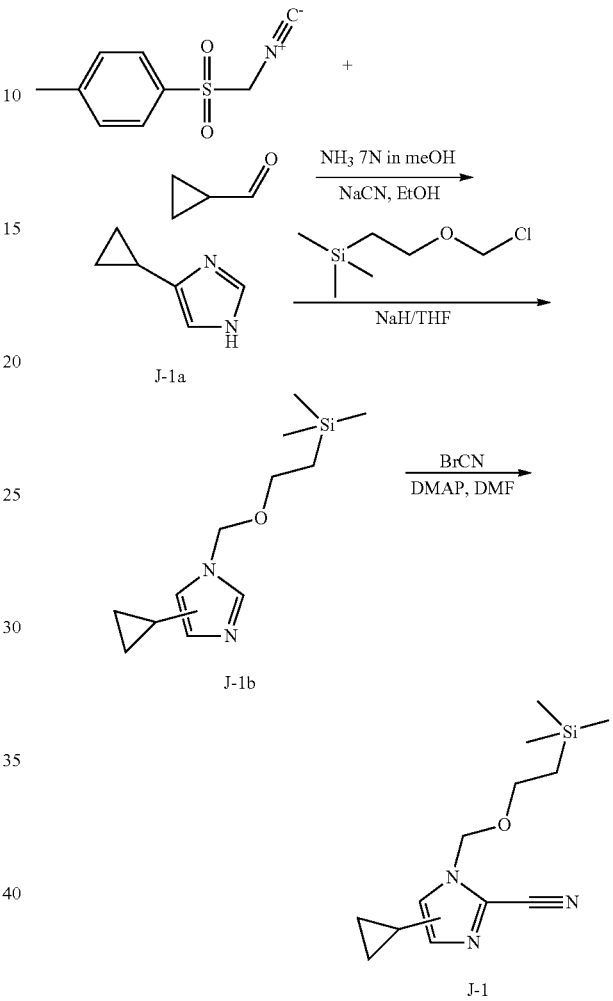

NaCN (360 mg; 7.35 mmol) was added to a suspension of cyclopropane-carboxaldehyde (5 g; 71.3 mmol) and tosyl-methyl-isocyanide (13.7 g; 69.9 mmol) in EtOH (200 mL). The resulting mixture was stirred for 1 h at RT. The solvent was removed under reduced pressure and the residue was washed with a mixture of heptane/ether (1:1). The beige dried powder was stirred in NH₃/MeOH 7N (480 mL; 3.36 mol) and the mixture was stirred at 100° C. in steel bomb for 16 h. The mixture was cooled to RT and the solvent was evaporated under reduced pressure. iPr₂O was added to the residue and the solid was filtered. The filtrate was evaporated to dryness and the crude was purified by preparative LC on (Irregular SiOH 20-45 μm 1000 g DAVISIL). Mobile phase (0.5% NH₄OH, 94% DCM, 6% MeOH). The pure fraction was collected and evaporated to give 4.9 g of intermediate J-1a as a brown oil (65% yield).

¹H NMR (DMSO-d₆, 400 MHz): δ (ppm) 8.60 (br. s., 1H), 7.58 (s, 1H), 6.76 (s, 1H), 1.85 (m, 1H), 0.86 (m, 2H), 0.71 (m, 2H).

J-1a (4.84 g; 44.8 mmol) in THF (60 mL) was added dropwise to a suspension of NaH (1.97 g; 49.2 mmol) in THF (200 mL) at 0° C. under N$_2$. The mixture was stirred at RT for 30 min and SEM-Cl (9.9 mL; 55.9 mmol) in THF (20 mL) was added dropwise at 0° C. The mixture was stirred at RT under N$_2$ for 16 h. Water was added and the product was extracted with DCM. The organic layer was dried over MgSO$_4$, filtered and concentrated under reduced pressure. The crude was purified by preparative LC (Irregular SiOH 20-45 μm, 150 g Merck, Mobile phase Gradient from 50% DCM, 50% heptane to 100% DCM). The fractions containing pure compound were combined and the solvent was removed under reduced pressure to give 6.6 g of J-1b as a yellow oil (62%).

Mixture of 2 regioisomers: 70/30

Minority Regioisomer:

$^1$H NMR (DMSO-d$_6$, 400 MHz): δ(ppm) 7.64 (s, 1H), 6.56 (s, 1H), 5.34 (s, 1H), 3.45 (t, J=8.08 Hz, 2H), 1.73-1.78 (m, 1H), 0.80-0.86 (m, 2H), 0.72-0.74 (m, 2H), 0.52-0.57 (m, 2H), −0.04 (s, 9H).

Majority Regioisomer:

$^1$H NMR (DMSO-d$_6$, 400 MHz): δ(ppm) 7.56 (s, 1H), 6.94 (s, 1H), 5.20 (s, 1H), 3.43 (t, J=8.08 Hz, 2H), 1.73-1.78 (m, 1H), 0.80-0.86 (m, 2H), 0.72-0.74 (m, 2H), 0.56-0.62 (m, 2H), −0.04 (s, 9H).

BrCN (6.11 g; 57.7 mmol) was added to a solution of DMAP (7.05 g; 57.7 mmol) in DMF (60 mL) at 10° C. The reaction was exothermic to 35° C. and a pale yellow precipitate was formed. The mixture was cooled to 10° C. and J-1b (5.5 g; 23.1 mmol) was added. The mixture was stirred at 40° C. for 6 h. Water was added and product was extracted with Et$_2$O (2 times). The combined organic layers were washed with brine, dried over MgSO$_4$, filtered and the solvent was removed under reduced pressure.

The crude was purified by preparative LC (Irregular SiOH 15-40 μm 220 g grace, mobile phase Heptane/DCM 50/50 to 10/90) to give 2.2 g impure J-1, which was further purified by preparative LC (irregular SiOH 15-40 μm 90 g Merck, mobile phase heptane/DCM 30/70) to give 0.94 g of J-1 as a mixture of two region-isomers (15% yield).

HPLC Rt (min)=6.11; MS M+ (H$^+$): 264 (method V1004V1012)

Alternative Synthesis of Intermediate J-1

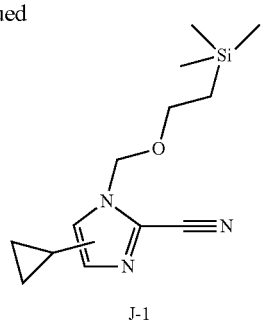

J-1

BuLi (1.6M in hexane) (11 mL; 17.6 mmol) was added to a solution of J-1b (3.5 g; 14.7 mmol) in THF (60 mL) at −50° C. The mixture was stirred at the same temperature for 30 min and DMF (1.7 mL; 22 mmol) was added. The mixture was warmed slowly to RT in 1 h and NH$_2$OH, HCl (970 mg; 29.4 mmol) was added and the mixture was stirred at RT for 16 h. Water was added and the product was extracted with DCM (3 times), washed with brine, dried over MgSO$_4$ and the solvent was removed under reduced pressure to give 4.1 g (quantitative yield) of the mixture of isomers K-1 as yellow oil.

HPLC Rt (min)=5.30, 5.41 and 5.90; MS M+ (H$^+$): 282 (method V2002V2002)

K-1 (3.1 g; 11 mmol) was dissolved in DCM (18 mL) and pyridine (19 mL) at RT. The mixture was cooled to 0° C. and TFAA (4.6 mL; 33 mmol) was added. The mixture was stirred at RT for 24 h. The solvent was removed under reduced pressure and the residue was dissolved in AcOEt. The organic layer was washed with water and brine, dried over MgSO$_4$, filtered and the solvent was removed under reduced pressure. The crude was purified by preparative LC (irregular SiOH 15-40 μm 90 g merck, mobile phase Heptane/DCM 30/70 to DCM 100%) to give 2.14 g of intermediate J-1 (73%) as a mixture of two isomers.

HPLC Rt (min)=6.51; MS M+ (H$^+$): 264 (method V2002V2002)

Overall Scheme in the Preparation of Final Products

Method 3

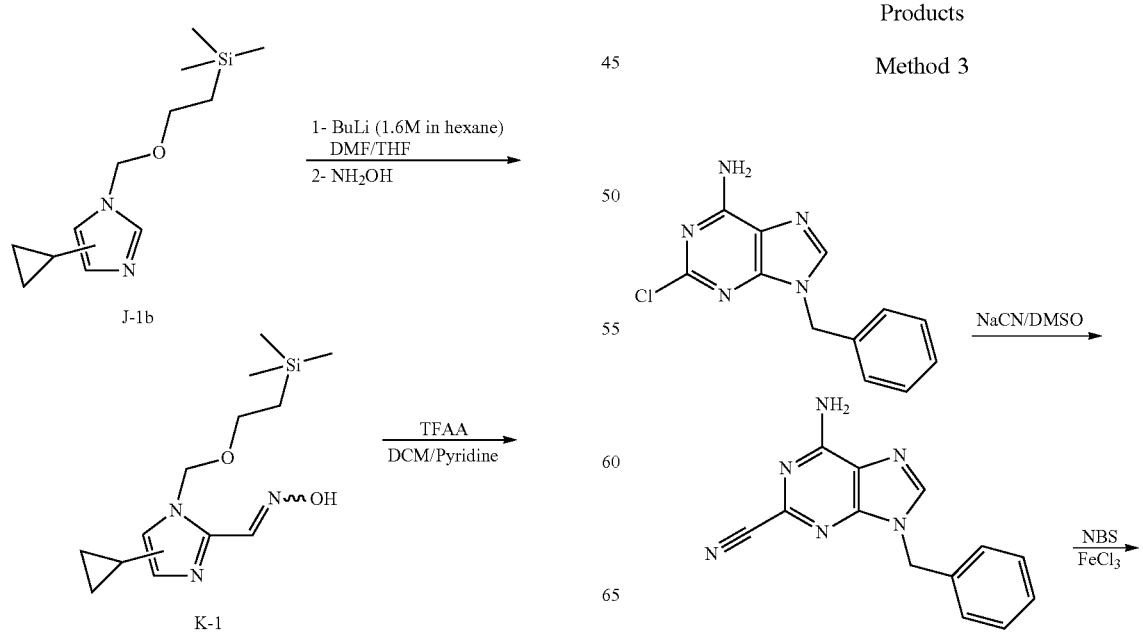

-continued

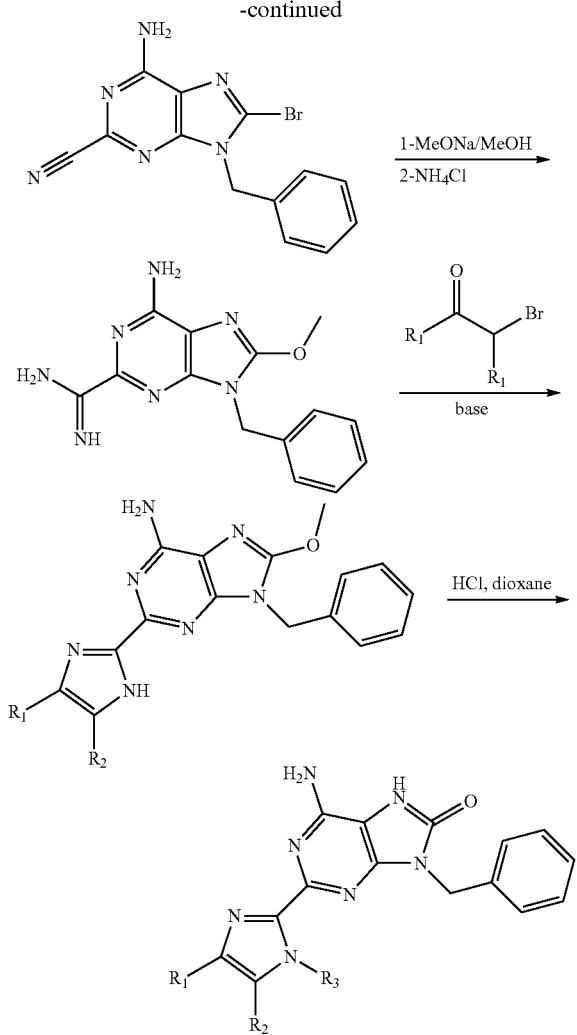

Synthesis of Intermediate N-1

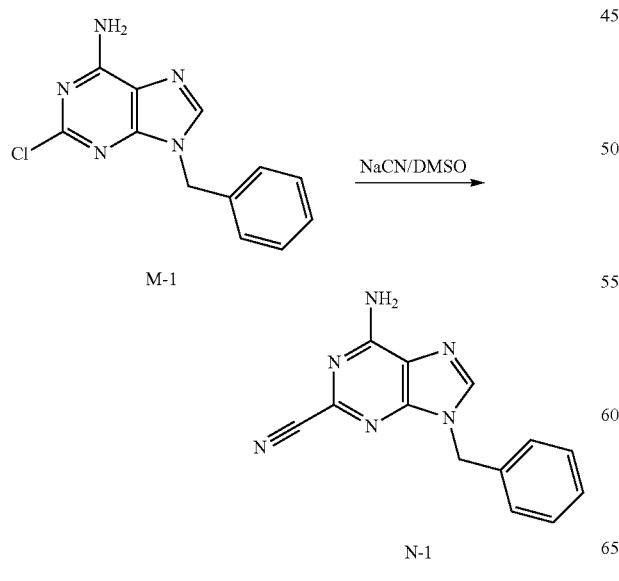

In a CEM microwave oven, a mixture of M-1 (its synthesis as such is described in WO2006117670 pages 57-58 "Preparation 1-4" respectively to obtain 6-Amino-9-benzyl-2-chloro-7,9-dihydro-purin-8-one) (9.7 g, 37.351 mmol), NaCN (3.11 g, 63.50 mmol) in DMSO (100 mL) was stirred at 150° C. for 4 h. The mixture was poured into water and the precipitate was filtered off, washed with water and dried under vacuum at 60° C. to give 8.6 g of intermediate N-1.

HPLC Rt (min)=5.23; MS M+ (H$^+$): 251 (method V2003V2002)

Synthesis of Intermediate O-1

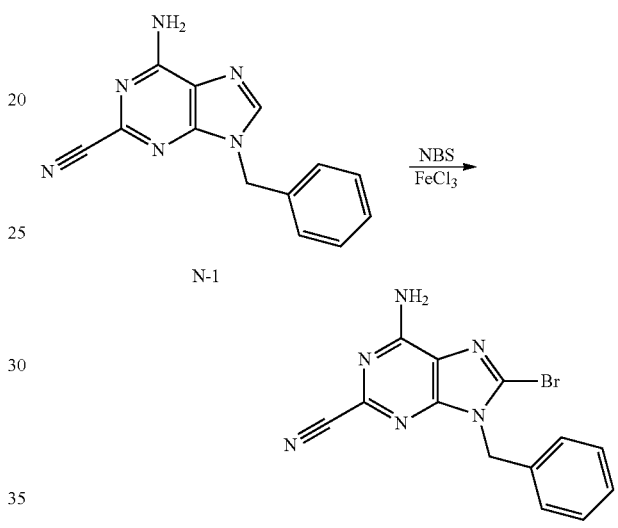

FeCl$_3$ (tip spatula) was added to a mixture of N-1 (3.70 g, 147.84 mmol) and NBS (26.2 g, 147.845 mmol) in CHCl$_3$ (60 mL). The mixture was stirred and refluxed for 3 h and then cooled to RT. The precipitate was filtered off. The filtrate was evaporated and purified by flash chromatography over silica gel (15-40 μm, 120 g, CH$_2$Cl$_2$/CH$_3$OH 99-1) to give 4.5 g of impure intermediate O-1. The fraction was taken up CH$_2$Cl$_2$ and the precipitate was filtered off to give 1.8 g of intermediate O-1.

HPLC Rt (min)=5.77; MS M+ (HCH$_3$CN$^+$): 370-372 (method V2003V2002)

Synthesis of Intermediate P-1

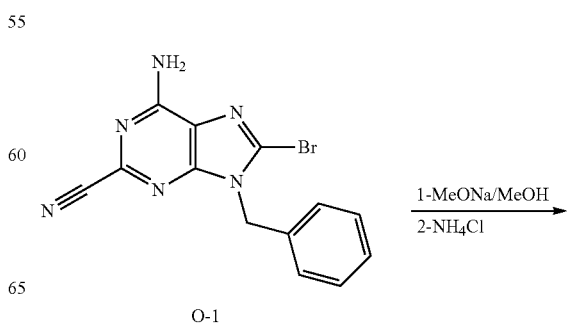

-continued

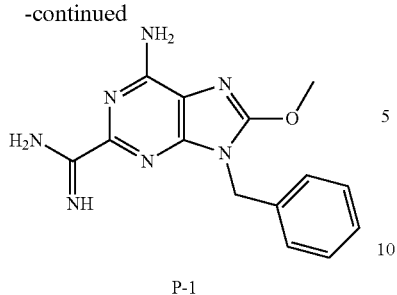

P-1

A mixture of O-1 (0.82 g, 2.491 mmol), MeONa/MeOH (30 wt % solution) (1.15 mL, 6.228 mmol) in MeOH (15 mL) was stirred at 50° C. for 2 h. NH$_4$Cl (333 mg, 6.228 mmol) was added and the mixture was stirred and refluxed for 2 h. The solvent was evaporated under reduced pressure. The crude was purified by flash chromatography over silica gel (15-40 μm, 90 g, CH$_2$Cl$_2$/CH$_3$OH/NH$_4$OH: 85-14-1). The pure fractions were collected and concentrated under reduced pressure to give 0.55 g of intermediate P-1 (74% yield).

HPLC Rt (min)=4.46; MS M+ (H$^+$): 298 (method V2003V2002)

Synthesis of Intermediate Q-1

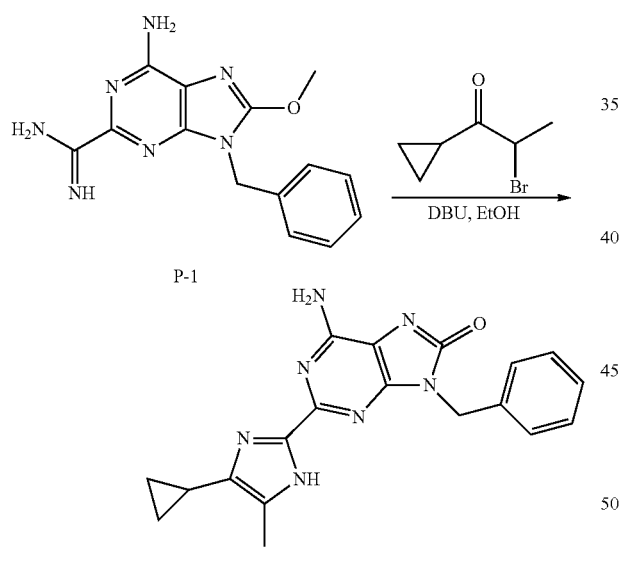

2-bromo-1-cyclopropyl-propan-1-one (104 mg, 0.589 mmol) was added dropwise to a mixture of P-1 (175 mg, 0.589 mmol) and DBU (0.264 mL, 1.766 mmol) in EtOH (5 mL). The mixture was stirred and refluxed for 5 h. The solvent was concentrated under reduced pressure. The crude was purified by flash chromatography over silica gel (15-40 μm, 40 g, CH$_2$Cl$_2$/CH$_3$OH/NH$_4$OH: 95/5/0.1). The pure fractions were collected and concentrated under reduced pressure to give 40 mg of intermediate Q-1. The crude compound was used directly in the next step.

HPLC Rt (min)=5.35; MS M+ (H$^+$): 376 (method V1005V1012)

Synthesis of Final Compound 5

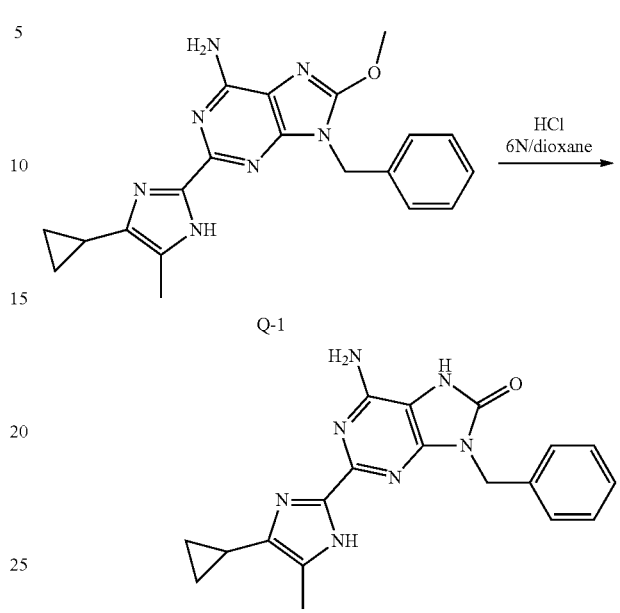

A mixture of Q-1 (40 mg, 0.107 mmol) in HCl 6N (1 mL) and dioxane (1 mL) was stirred at RT for 6 h. The mixture was half-evaporated under reduce pressure. The solution was cooled to 0° C., basified with NaHCO$_3$ and extracted with EtOAc—CH$_3$OH (90-10). The combined organic layers were dried over MgSO$_4$, filtered and the solvent was evaporated under reduce pressure. The crude was purified by flash chromatography over silica gel (15-40 μm, 10 g, CH$_2$Cl$_2$/CH$_3$OH/NH$_4$OH:88-12-0.5) The pure fractions were collected and concentrated under reduced pressure. The resulting solid (35 mg) was crystallized from Et$_2$O to afford 25 mg of Compound 5 (64% yield, MP>260° C.).

Overall Scheme in the Preparation of Final Products

Method 4

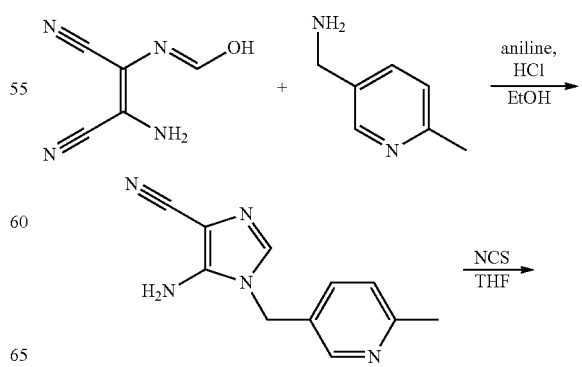

-continued

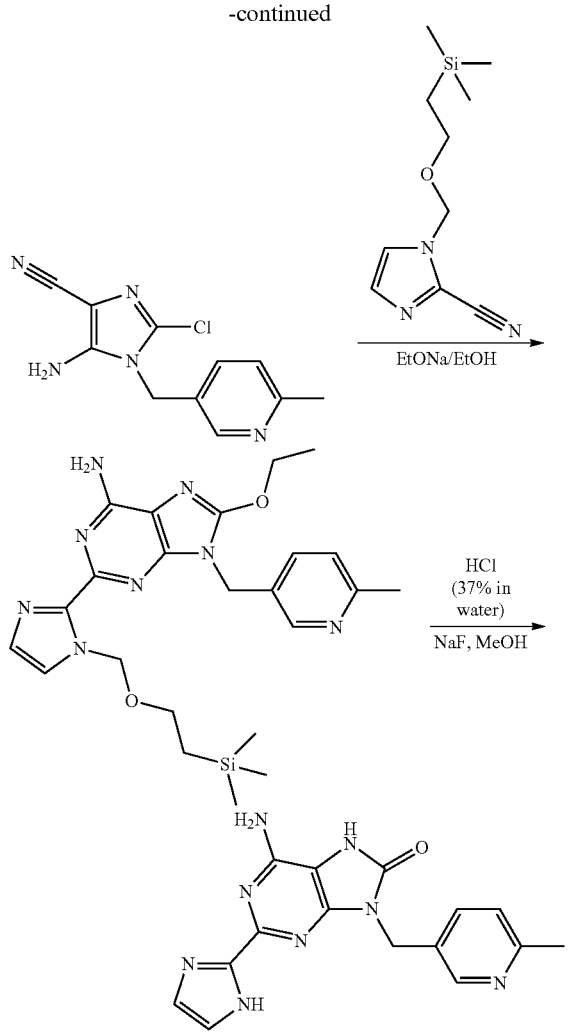

Synthesis of Intermediate T-1

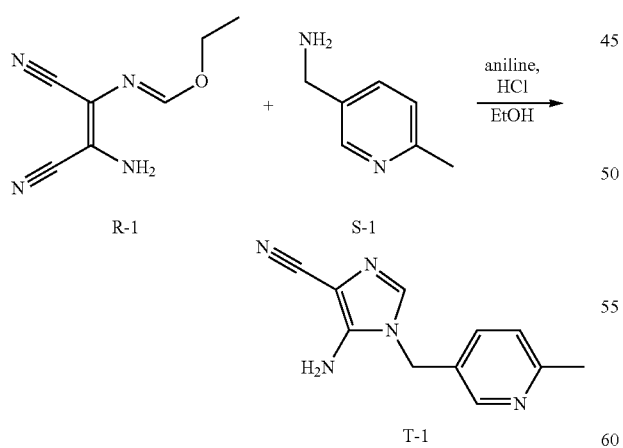

S-1 (synthesis described in J. Med. Chem. 1996, 39, 13, 2586-2593) (1.14 g; 9.33 mmol) was added drop wise to a solution of R-1 (synthesis described in WO2006/117670) (1.46 g; 8.89 mmol) and aniline, HCl (18 mg; 0.14 mmol) in EtOH (30 mL) at 10° C. The reaction mixture was stirred at RT for 20 h. An aqueous solution of NaOH 3M (30 mL) was added dropwise to the solution at 10° C. and the resultant mixture was stirred at RT for 1 h. The aqueous layer was extracted with DCM (3 times). The combined organic layers were washed with a saturated aqueous solution of NaHCO$_3$, dried over MgSO$_4$, filtered and concentrated in vacuo to give 1.20 g of T-1 as a brown solid (63% yield). T-1 was used in the next step without further purification. HPLC Rt (min)=4.45; MS M+ (H$^+$): 214 (method V1010V1012)

Synthesis of Intermediate U-1

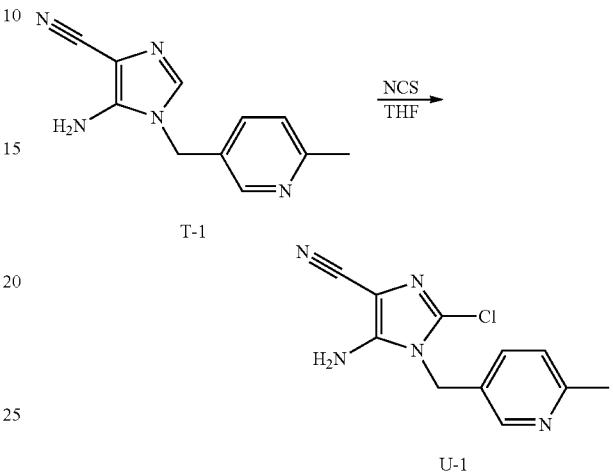

A solution of NCS (475 mg; 3.56 mmol) in THF (10 mL) was added dropwise to a solution of T-1 (690 mg; 3.24 mmol) in THF (35 mL). The solution was stirred at RT for 20 h under N$_2$ flow. A solution of NCS (260 mg; 1.94 mmol) in THF (5 mL) was added drop wise to the solution. The solution was stirred at RT for 16 h under N$_2$ flow. The mixture was taken up with DCM, washed with a saturated aqueous solution of NaHCO$_3$, washed with brine, dried over MgSO$_4$, filtered and evaporated in vacuo to give 950 mg of a brown solid. The crude was purified by preparative LC (Irregular SiOH 15-40 μm, 40 g Grace, liquide sample, mobile phase: 98% DCM, 2% MeOH to 90% DCM, 10% MeOH). The fractions containing pure compound were combined and the solvent was removed in vacuum to give 200 mg of U-1 as a brown solid (25% yield).

HPLC Rt (min)=5.13; MS M+ (H$^+$): 248-250 (method V2012V2002)

Synthesis of Intermediate W-1

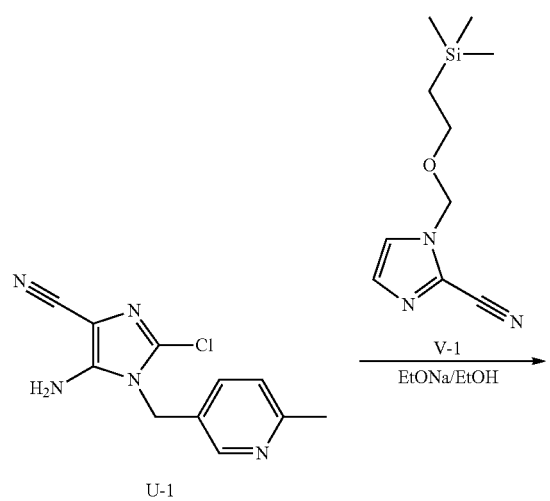

-continued

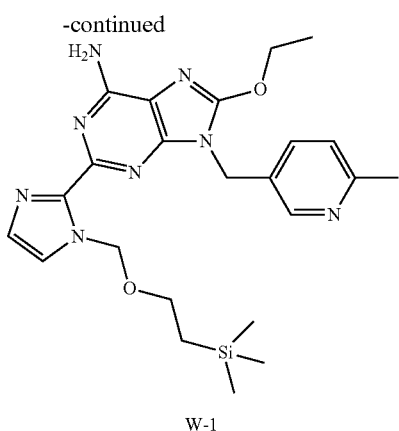

W-1

EtONa (398 mg; 5.85 mmol) was added to a solution of U-1 (290 mg; 1.17 mmol) and V-1 (270 mg; 1.21 mmol) in EtOH (15 mL). The mixture was stirred at 90° C. for 16 h. The solvent was removed under reduced pressure. The crude was purified by preparative LC (irregular SiOH 15-40 μm, 50 g Merck, solid sample, mobile phase 97/3/0.1). The fraction containing pure compound were combined and the solvent was removed to give 210 mg of W-1 as a lightly yellow solid (37% yield).

HPLC Rt (min)=6.68; MS M+ (H+): 248-250 (method V1010V1012)

Synthesis of Compound 9

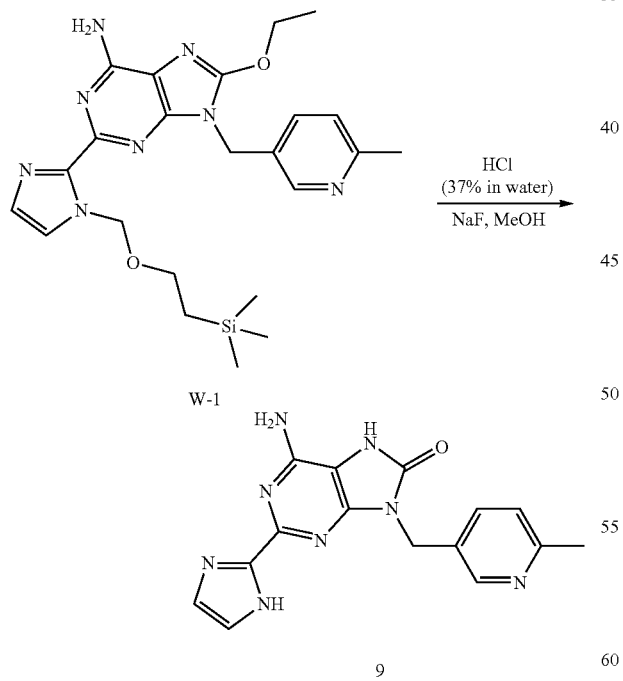

NaF (91 mg; 2.18 mmol) was added to a solution of W-1 (210 mg; 0.44 mmol) in HCl 37% in water (15 mL) and MeOH (10 mL). The mixture was stirred at 40° C. for 16 h. The mixture was cooled to RT and a 10% aqueous solution of $K_2CO_3$ was added until basic pH. The aqueous layer was saturated with $K_2CO_3$ powder and the product was extracted with DCM/MeOH (95/5) (3 times). The combined organic layers were dried over $MgSO_4$, filtered and the solvent was removed under reduced pressure. The crude was purified by preparative LC (irregular SiOH 15-40 μm, Merck 10 g, mobile phase DCM/MeOH/$NH_3$aq 93/3/0.1 to 85/15/1). The fractions containing pure compound were combined, the solvent was removed in vacuo and the title compound was dried in vacuo for 16 h at 60° C. to give 9.8 mg of Compound 9 (6%) as a pale brown solid. m.p.>260° C.

Overall Scheme in the Preparation of Final Products

Method 5

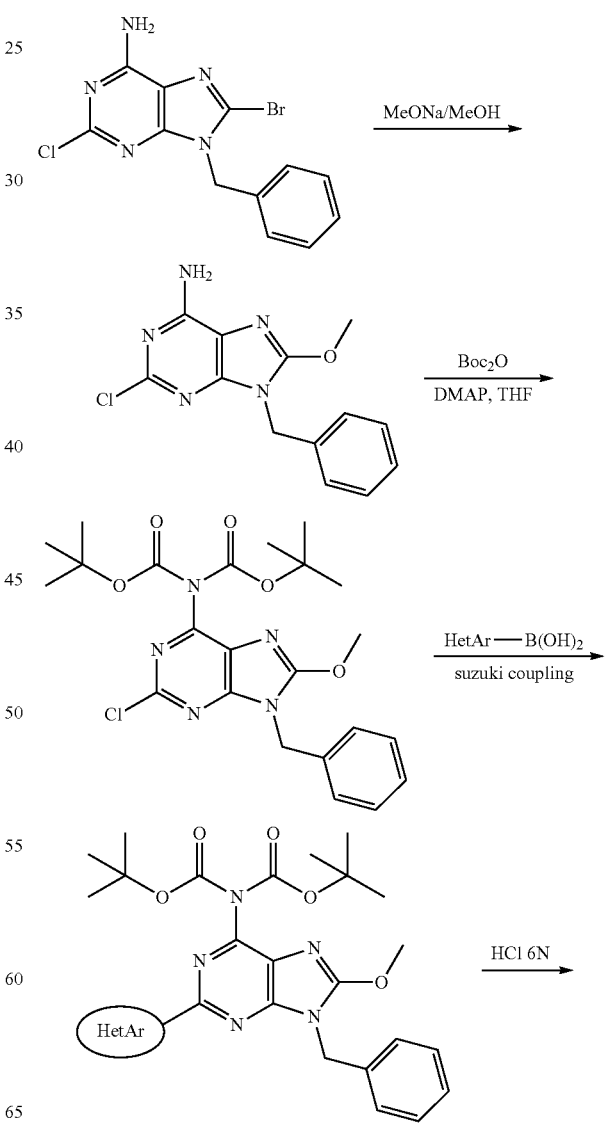

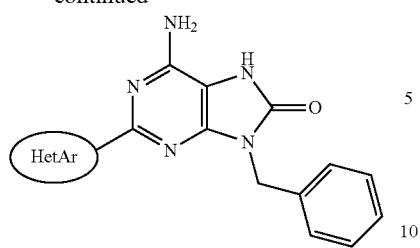

Synthesis of Intermediate Y1

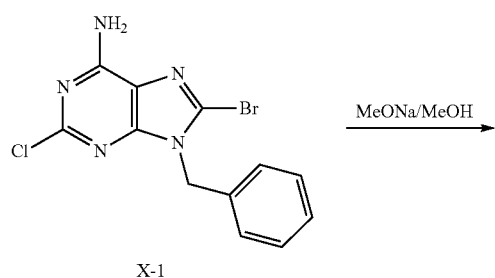

Sodium methoxide (30 wt % in MeOH) (15.6 mL, 84.172 mmol) was added drop wise to a mixture of X1 (synthesis described in Bioorg. Med. Chem., 11, 2003, 5501-5508) (5.7 g, 16.834 mmol) in MeOH (150 mL) at RT. The mixture was stirred at 60° C. for 6 h and then cooled down to RT. The precipitate was filtered off and dried, to yield 3.25 g of Y1. The crude compound was used in the next step.

HPLC Rt (min)=5.53; MS M+ (H⁺): 290-292 (method V2003V2002)

Synthesis of Intermediate Z-1

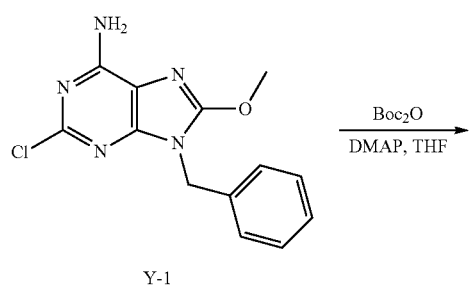

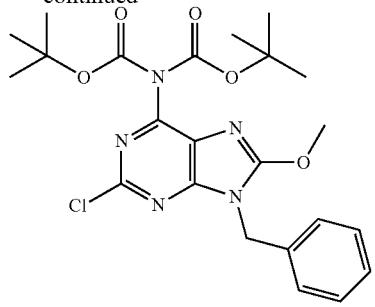

Boc₂O (3.0 g, 13.806 mmol) was added under a N₂ flow to a mixture of Y-1 (1.0 g, 3.452 mmol), DMAP (42 mg, 0.345 mmol) in THF (10 mL) at RT. The mixture was stirred at 80° C. for 2 h. The mixture was poured into water and extracted with EtOAc. The organic layer was washed with water, dried over MgSO₄, filtered and the solvent was evaporated. The crude was purified by preparative LC on (Irregular SiOH 20-45 μm 450 g MATREX). Mobile phase (Gradient from 98% DCM, 2% AcOEt to 95% DCM, 5% AcOEt) to afford 0.825 g of Z-1 (49% yield, MP=159° C.).

HPLC Rt (min)=4.43; MS M+ (H⁺): 490-492 (method V2015V2007)

Synthesis of Intermediate B-2

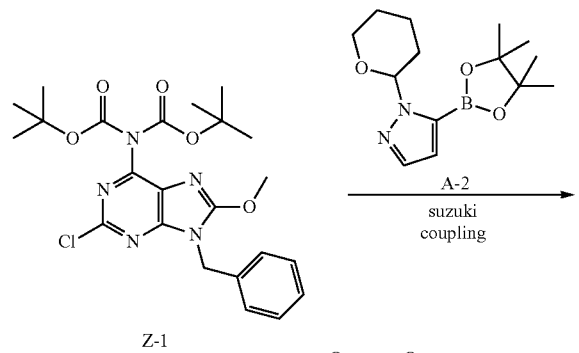

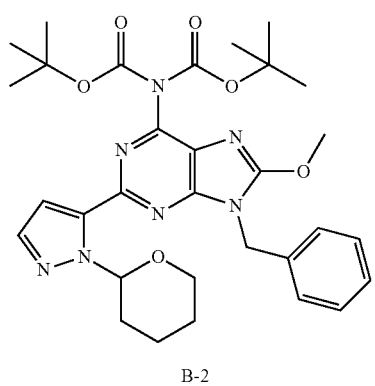

A solution of Z-1 (300 mg, 0.612 mmol), A-2 (255 mg, 0.918 mmol) and NaHCO₃ (257 mg, 3.06 mmol) in dioxane/water (4/1) (3 mL) was degassed by bubbling N₂ for 10 min. Tetrakis-(triphenylphosphine)-Palladium (142 mg, 0.122 mmol) was added and the mixture was stirred at 100° C. for 5 h. Water and EtOAc were added and the layers were decanted. The aqueous layer was extracted with EtOAc. The organic layers were combined, dried over MgSO$_4$, filtered and the solvent was evaporated in the next step without further purification.

Synthesis of Final Compound 23

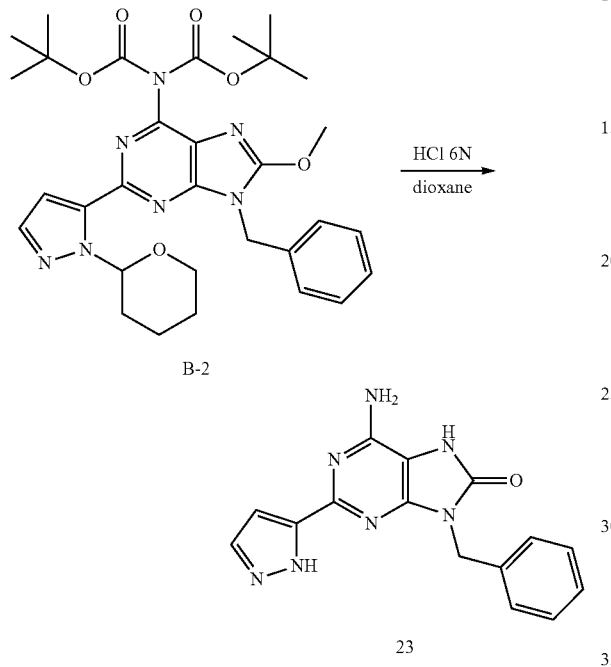

B-2

23

HCl 6N (10 mL) was added to a solution of B-2 (0.7 g, 1.15 mmol) in dioxane (7 mL) at 0° C. The mixture was stirred at RT for 12 h and then cooled down to 0° C. and basified with K$_2$CO$_3$. The mixture was extracted with EtOAc+CH$_3$OH (90-10). The combined organic layers was dried over MgSO$_4$, filtered and the solvent was evaporated. The crude was purified by preparative LC on (Stability Silica 5 μm 150×30.0 mm). Mobile phase (Gradient from 0.3% NH$_4$OH, 97% DCM, 3% MeOH to 1.4% NH$_4$OH, 86% DCM, 14% MeOH), to yield 67 mg of final Compound 23 after crystallization from CH$_3$OH (19% yield).

Overall Scheme in the Preparation of Final Products

Method 6

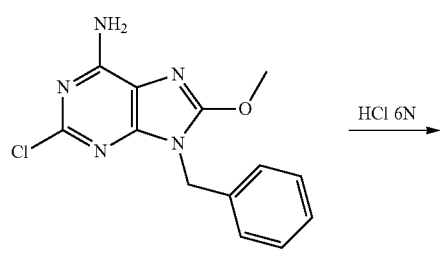

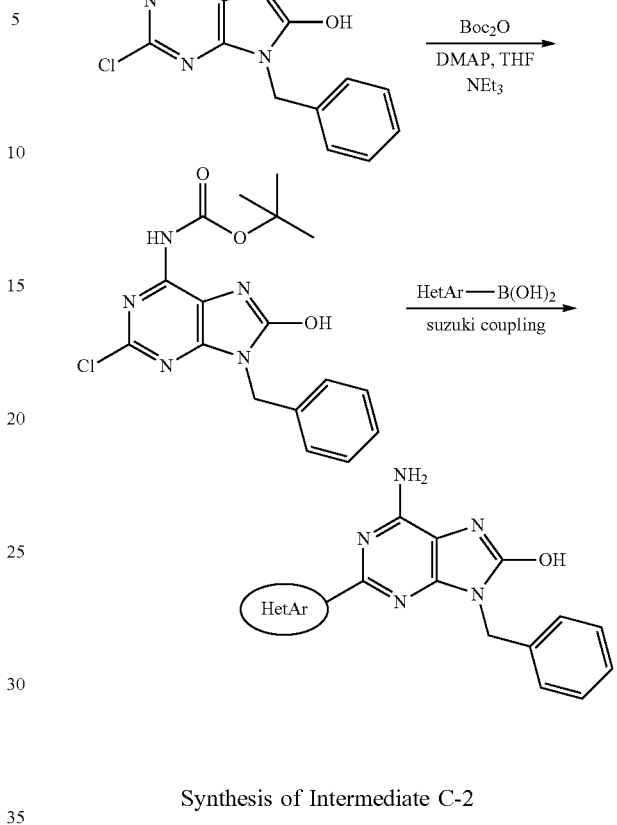

Synthesis of Intermediate C-2

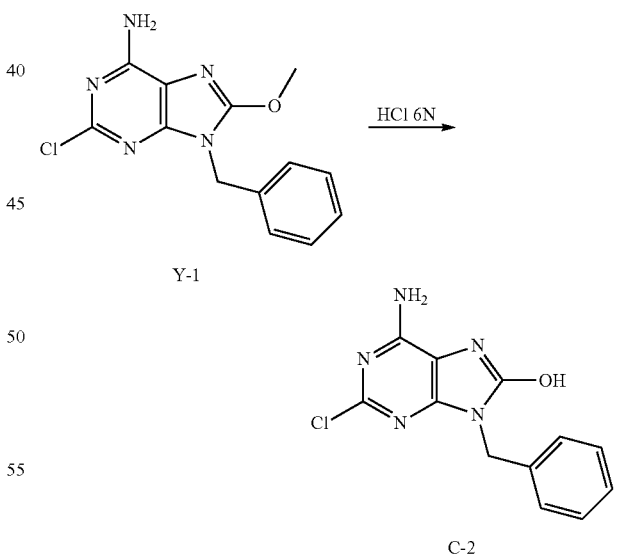

Y-1

C-2

A mixture of Y-1 (0.53 g, 1.829 mmol) in HCl 6N (5 mL) and dioxane (5 mL) was stirred at RT for 18 h. The precipitate was filtered off, washed with the minimum of cold dioxane and dried to afford 0.28 g of crude C-2, which was used in the next step without further purification.

HPLC Rt (min)=4.96; MS M+ (H$^+$): 276-278 (method V2003V2002)

Synthesis of Intermediate D-2

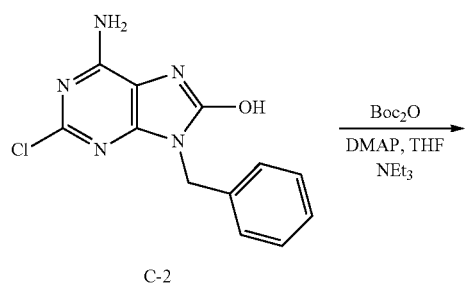

NEt₃ (0.187 mL, 1.345 mmol) and then Boc₂O (0.215 g, 0.987 mmol) were added to a mixture of C-2 (0.28 g, 0.897 mmol) and DMAP (11 mg, 0.0897 mmol) in THF (3 mL) at RT. The mixture was stirred at 80° C. for 2 h. Water and EtOAc were added. The layers were decanted. The organic layer was dried over MgSO₄, filtered and the solvent was evaporated to yield 0.18 g of intermediate D-2. The crude compound was used directly in the next step.

HPLC Rt (min)=6.31; MS M+ (H⁺): 376-378 (method V2002V2002)

Synthesis of Final Compound 20

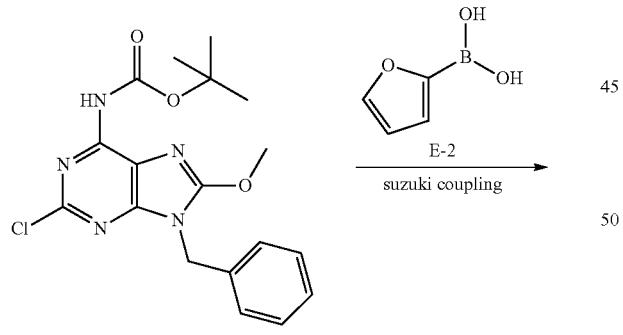

A solution of D-2 (240 mg, 0.64 mmol), E-2 (107 mg, 0.96 mmol) and NaHCO₃ (269 mg, 3.2 mmol) in dioxane/water (4/1) (3.2 mL) was degassed by bubbling N₂ for 10 min. Tetrakis-(triphenylphosphine)-Palladium (148 mg, 0.13 mmol) was added and the mixture was stirred at 100° C. for 16 h. Water and EtOAc were added and the layers were decanted. The aqueous layer was extracted with EtOAc. The organic layers were combined, dried over MgSO₄, filtered and the solvent was evaporated. The crude was purified on a reverse phase to yield 13 mg of final Compound 20 (6% yield).

Overall Scheme in the Preparation of Final Products

Method 7

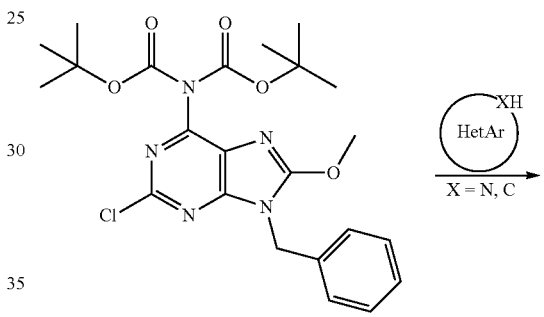

Synthesis of Final Compound 36

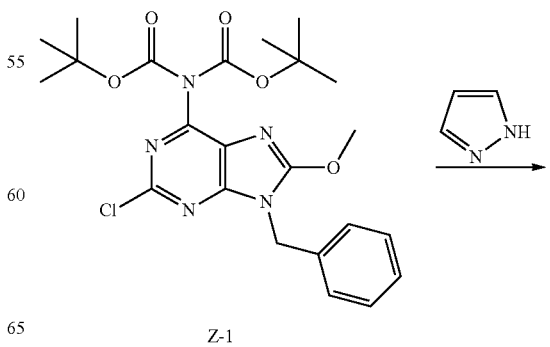

-continued

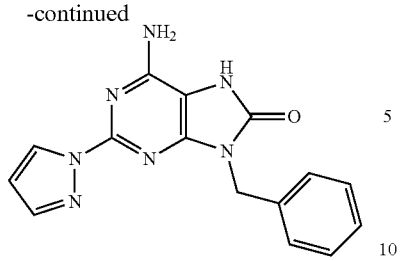

36

A mixture of Z-1 (300 mg, 0.612 mmol) and pyrazole (417 mg, 6.123 mmol) was stirred at 180° C. for 1 h (microwave biotage). The crude compound was purified by chromatography over silicagel column (15-40 μm, 25 g) in CH₂Cl₂/MeOH/NH₄OH 96/4/0.5 to give, after crystallization in diisopropylether and drying under vacuum pressure at 80° C., 85 mg of final compound 36.

Overall Scheme in the Preparation of Final Products

Method 8

Synthesis of Intermediate G-2

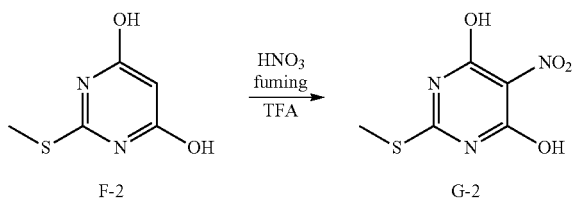

A solution of F-2 (50 g, 316.09 mmol) in TFA (210 mL) was stirred at RT for 30 min. The mixture was cooled to 5° C. then HNO₃ fuming (19.5 mL, 426.73 mmol) was added drop wise at 5° C. The temperature was maintained at 10-15° C. during the addition. The ice bath was removed and when the temperature reached 20° C., a violent exothermic event occurred (from 20° C. to 45° C. in 5 seconds). The mixture was stirred at RT for 16 h. The mixture was poured into a mixture of water and ice. The precipitate was filtered off and washed with water. The precipitate was dried under vacuum at 50° C. to give 42 g (65% yield) of intermediate G-2. This intermediate was directly used in the next step without any further purification.

Synthesis of Intermediate H-2

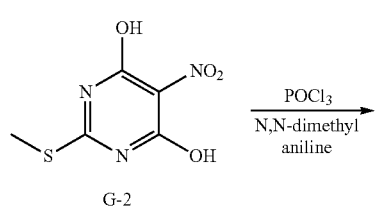

-continued

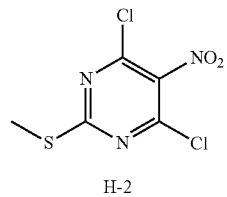

N,N-dimethylaniline (76.7 mL, 0.61 mol) was added drop wise to POCl₃ (93.7 mL, 1.01 mol) at 0° C. G-2 (41 g, 201.79 mmol) was added portion wise at 0° C. then the mixture was warmed to 100° C. for 2 h. The solution was concentrated under vacuum and the residual POCl₃ was removed by azeotropic evaporation with toluene (3 times). The resulting oil was taken up in a solution of CH₂Cl₂-Heptane (70-30) and was filtered through a glass filter of SiO₂. The filtrate was concentrated and the residue was purified by preparative LC on (Irregular SiOH 20-45 μm 1000 g DAVISIL), mobile phase (80% Heptane, 20% CH₂Cl₂). The pure fractions were collected and concentrated to give 37.8 g (78% yield) of intermediate H-2.

Synthesis of Intermediate I-2

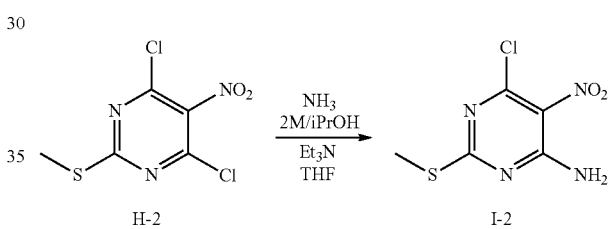

A solution of NH₃ 2M in iPrOH (115 mL, 229.31 mmol) was added drop wise to a solution of H-2 (36.7 g, 152.87 mmol) and Et₃N (23.4 mL, 168.16 mmol) in THF (360 mL) (the temperature was maintained at RT with an ice-water bath during the addition). The reaction mixture was stirred at RT for 5 h. The mixture was evaporated to dryness. Water and EtOAc were added to the residue. The layers were separated and the aqueous layer was extracted with EtOAc (twice). The combined organic layers were dried over MgSO₄, filtered, and the solvent was removed under reduced pressure to give 34.5 g (100% yield) of intermediate I-2.

Synthesis of Intermediate J-2

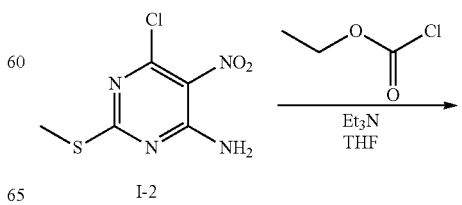

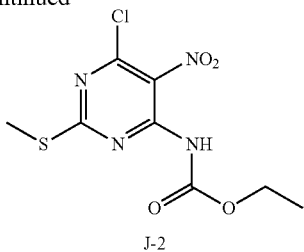

J-2

Ethyl chloroformate (13.5 mL, 138.90 mmol) was added to a solution of I-2 (39.8 g, 126.27 mmol) and Et₃N (26.5 mL, 189.40 mmol) in THF (1300 mL). The mixture was stirred at RT for 6 h and the solvent was partially evaporated under reduced pressure. The residue was taken up in CH₂Cl₂ and water. The layers were separated; the aqueous layer was extracted with CH₂Cl₂ (twice). The combined organic layers were dried over MgSO₄, filtered and the solvent was removed under reduced pressure. The residue was purified by preparative LC on (Irregular SiOH 20-45 μm 1000 g DAVISIL), mobile phase (gradient from 85% heptane, 15% AcOEt to 80% heptane, 20% AcOEt). The pure fractions were collected and concentrated to give 35 g (95% yield) of intermediate J-2.

Synthesis of Intermediate L-2

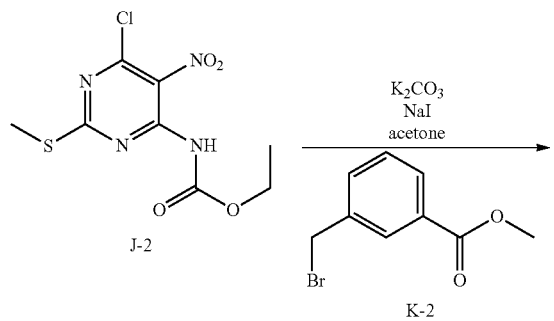

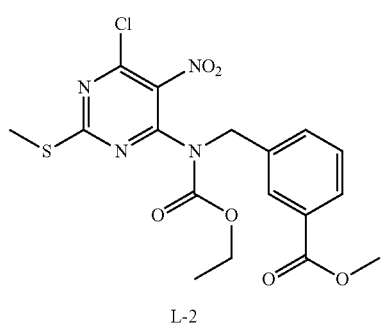

L-2

J-2 (5 g, 17.0 mmol), K-2 (3.91 g, 17.0 mmol), K₂CO₃ (5.90 g, 42.7 mmol) and NaI (2.56 g, 17.0 mmol) in acetone (130 mL) were stirred at RT for 18 h. The solution was filtered and the filtrate was evaporated under reduced pressure. The crude compound was purified by preparative LC (irregular SiOH 15-40 μm, 120 g merck, solid sample, mobile phase: heptane/EtOAc 100/0 to 80/20) to give intermediate L-2 as a pale yellow solid (69% yield).

Synthesis of Intermediate M-2

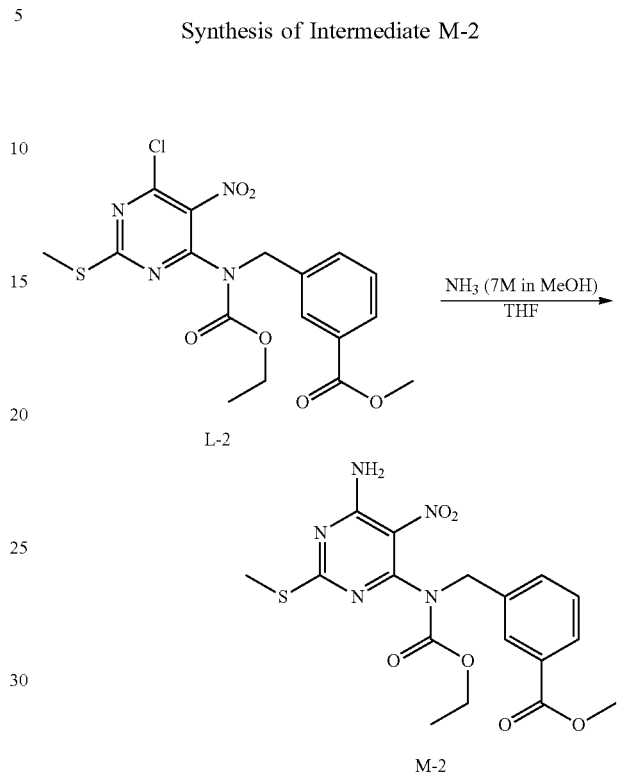

The reaction was done in two batches of 2.7 g of L-2.

Here is the protocol for one batch of 2.7 g: In a sealed tube, L-2 (2.70 g, 6.12 mmol) was stirred in NH₃ (7 M in MeOH) (50 mL) and THF (50 mL) at RT for 2 h.

The two batches were mixed.

The mixture was evaporated in vacuo and the residue was dried by azeotropic distillation with EtOH (twice) to give a yellow solid. Water and EtOAc were added, the layers were separated and the aqueous layer was extracted with EtOAc (twice). The combined organic layers were dried over MgSO₄, filtered and evaporated in vacuo to give 4.9 g of intermediate M-2 as a yellow solid (90% yield).

Synthesis of Intermediate N-2

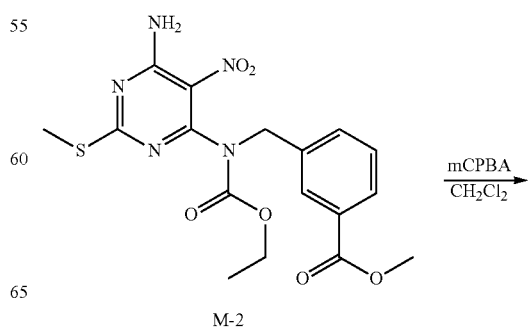

M-2

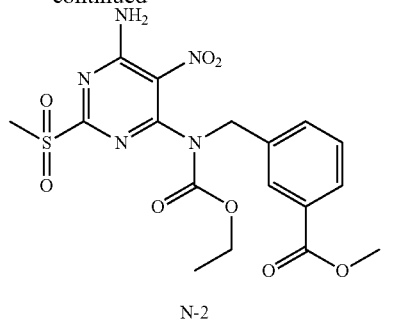

N-2 mCPBA (1.46 g, 5.93 mmol) was added portionwise to a solution of M-2 (1 g, 2.37 mmol) in CH$_2$Cl$_2$ (60 mL) at 0° C. The mixture was stirred at RT for 20 h. An aqueous solution of Na$_2$S$_2$O$_3$ was added to the mixture. The layers were separated and the aqueous layer was extracted with CH$_2$Cl$_2$ (twice). The combined organic layers were washed with a saturated aqueous solution of NaHCO$_3$, dried over MgSO$_4$, filtered and the solvent was removed under reduced pressure to give 980 mg of intermediate N-2 as a yellow solid (91% yield). Intermediate N-2 was used in the next step without further purification.

Synthesis of intermediate O-2

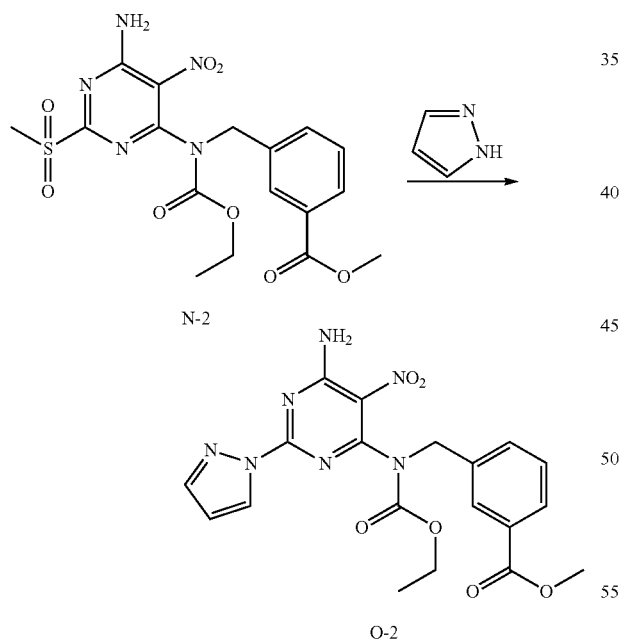

A mixture of N-2 (500 mg, 1.10 mmol) and pyrazole (750 mg, 11.0 mmol) was stirred at 80° C. for 45 min. The resulting mixture was take up with EtOAc and 1 M aqueous solution of HCl. The layers were separated, the organic layer was dried over MgSO$_4$, filtered and dried in vacuo to give 550 mg of a yellow solid. The crude compound was purified by preparative LC (irregular SiOH 15-40 μm, 25 g Grace, solid sample, mobile phase gradient: from CH$_2$Cl$_2$/MeOH/ NH$_3$aq 97/3/0.03 to 80/20/0.3) to give 370 mg of intermediate O-2 as a white solid (76% yield).

Synthesis of Final Compound 37

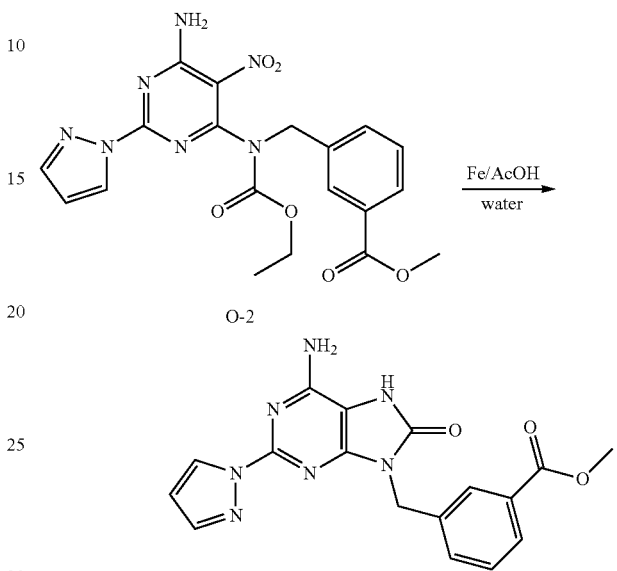

Fe (280 mg, 5.01 mmol) was added to a mixture of O-2 (365 mg, 827 μmol) in AcOH (17 mL) and water (1.8 mL). The mixture was stirred vigorously at RT for 64 h. The reaction mixture was filtered on a pad of celite, concentrated in vacuo and co-evaporated with toluene (twice) to give a dark residue. The crude was purified by preparative LC (Irregular SiOH 15-40 μm, 25 g Merck, solid sample, mobile phase gradient: from CH$_2$Cl$_2$/MeOH/NH$_3$aq 96/4/0.4 to 80/20/3) to give 250 mg of a white solid, which was purified again by preparative LC (Irregular SiOH 15-40 μm, 25 g Merck, solid sample, mobile phase gradient: from CH$_2$Cl$_2$/ MeOH/NH$_3$aq 96/4/0.4 to 80/20/3) to give 110 mg of fraction 1 as a white solid (36%) and 25 mg of fraction 2 as a white solid (8%). Global yield: 45%. 8 mg of fraction 2 were dried in vacuo for 16 h at 40° C. to give 6 mg of final compound 37 as a white solid.

Synthesis of Final Compound 38

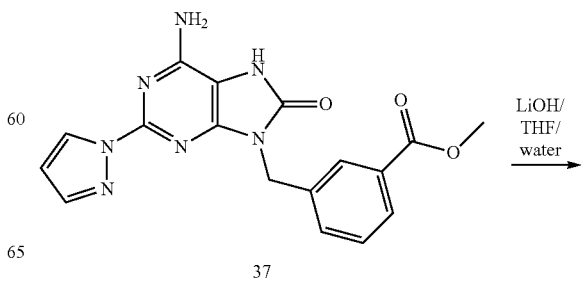

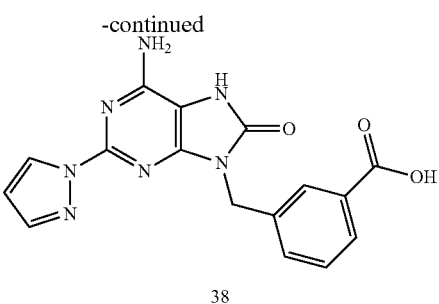

38

LiOH (9 mg, 123 µmol) was added to a suspension of 37 (15 mg, 41.1 µmol) in THF (4 mL) and water (5 mL). The reaction mixture was stirred at RT for 16 h. A 10% aqueous solution of $K_2CO_3$ was added until basic pH. The aqueous layer was saturated with $K_2CO_3$ powder and the product was extracted with $CH_2Cl_2$/MeOH (9/1) (3 times). The combined organic layers were dried over $MgSO_4$, filtered and the solvent was removed under reduced pressure to give 200 mg. The crude was purified by preparative LC on (X-Bridge-C18 5 µm 30*150 mm, mobile phase: gradient $H_2O$ (0.1% Formic Acid)/MeCN 90/10 to 0/100) to give 12 mg of final compound 38 as a white solid (83%).

Synthesis of Final Compound 39

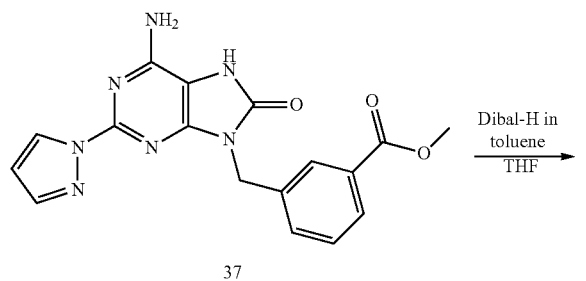

Dibal-H (1.2 M in toluene) (0.2 mL, 240 µmol) was added dropwise to a solution of 37 (30 mg, 82.1 µmol) in THF (3 mL) and toluene (1 mL) under nitrogen at 0° C. The solution was stirred at 0° C. for 2 h. Dibal-H (0.2 mL, 240 µmol) was added and the solution was stirred at RT for 2 h. A saturated aqueous solution of potassium sodium tartrate was added to neutralize the reaction. The mixture was diluted with EtOAc, followed by stirring vigorously for 30 min. The organic layer was separated from the aqueous layer, washed with brine, dried over $MgSO_4$, filtered and concentrated in vacuo to give 40 mg. The crude was purified by preparative LC (irregular SiOH 15-40 µm, 4 g Grace, solid sample, mobile phase gradient: from $CH_2Cl_2$/MeOH/$NH_3$aq 96/4/0.04 to 80/20/2) to give a white solid. The afforded white solid was dried in vacuo for 16 h at 40° C. to give 8 mg of final compound 39 (29%) as a white solid.

Synthesis of Final Compound 40

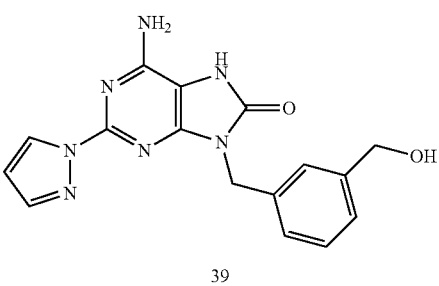

39 (45 mg, 133 µmol) was solubilized in HBr (30% in AcOH) (10 mL). The mixture was stirred at RT for 1 h. The solvent was evaporated and AcOH was azeotropically distilled with toluene (twice) to give 75 mg of intermediate P-2 as a brown solid, which was used for the next step without further purification.

To a suspension of NaH (53 mg, 1.33 mmol) in THF (4 mL) was added dropwise diethyl phosphite (0.130 mL, 1.33 mmol) at RT. The mixture was stirred at RT for 1 h. To the mixture was added a solution of P-2 (64 mg, 133 µmol) in THF (4 mL). The mixture was stirred at RT for 16 h. To a suspension of NaH (53 mg, 1.33 mmol) in THF (4 mL) was added dropwise diethyl phosphite (0.130 mL; 1.33 mmol) at RT. The resulting mixture was added to the reaction mixture. The resulting reaction mixture was stirred at RT for 1 h. Water and EtOAc were added, the layers were separated and the organic layer was washed with an aqueous solution of $NaHCO_3$ and brine, dried over $MgSO_4$, filtered and concentrated in vacuo to give 75 mg of a clear oil. The crude was purified by preparative LC (Irregular SiOH 15-40 µm, 25 g Merck, dry loading, mobile phase gradient: from $CH_2Cl_2$/MeOH 100/0 to 85/15) to give 38 mg of a white solid, which was triturated in pentane. The resulting solid was filtered and dried in vacuo for 16 h at 50° C. to give 28 mg of final compound 40 as a white solid (40% yield).

Synthesis of Final Compound 41

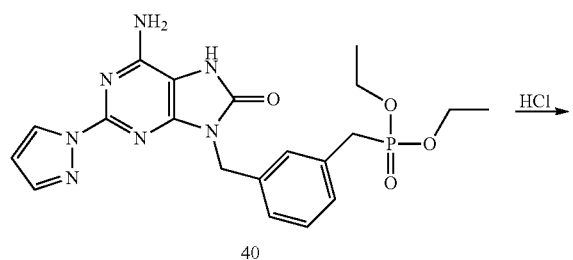

40

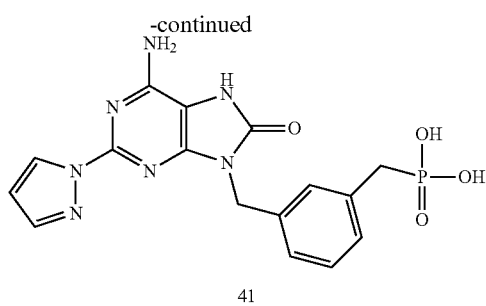

41

40 (590 mg, 1.29 mmol) was solubilized in HCl (37% in water) (60 mL). The mixture was stirred at 100° C. for 16 h. The solvent was evaporated and H₂O was azeotropically distilled with EtOH (twice) to give 605 mg of final compound 41 as a white solid (100% yield).

TABLE 1

Compounds of formula (I).

| # | STRUCTURE | Exact Mass | Mass Found [M + H] | LCMS Ret Time, Method | Synthesis method | MP (° C.) | H NMR |
|---|---|---|---|---|---|---|---|
| 1 | 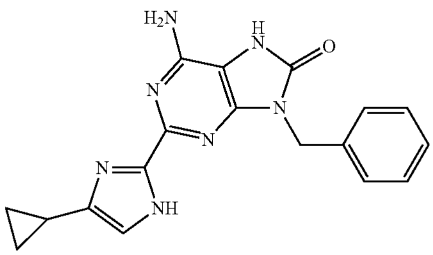 [SMILES: Nc1nc(-c2nc(C3CC3)c[nH]2)nc2c1[nH]c(=O)n2Cc1ccccc1] | 347.15 | 348 | 1.01, B | 1,2 | | ¹H NMR (600 MHz, DMSO-d₆) δ ppm 0.84 (br. s., 2 H), 0.99 (d, J = 6.7 Hz, 2 H), 2.00 (br. s., 1 H), 3.16 (br. s., 1 H), 5.03 (br. s., 2 H), 7 08-7.21 (m, 2 H), 7.24-7.35 (m, 3 H), 7.36-7.45 (m, 3 H), 11.51 (br. s., 1 H) |
| 2 | 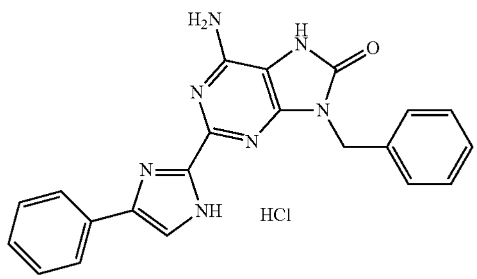 [SMILES: Nc1nc(-c2nc(-c3ccccc3)c[nH]2)nc2c1[nH]c(=O)n2Cc1ccccc1 ; Cl] | 383.15 | 384 | 1.18, B | 1 | | ¹H NMR (400 MHz, DMSO-d₆) δ ppm 5.08 (s, 2 H), 7.04 (br. s., 2 H), 7.29 (m, J = 7.3 Hz, 1 H), 7.34 (t, J = 7.3 Hz, 2 H), 7.40-7 48 (m, 3 H), 7.49-7.56 (m, 2 H), 7.97 (d, J = 7.3 Hz, 2 H), 8.20 (s, 1 H), 11.28 (s, 1 H) |
| 3 | 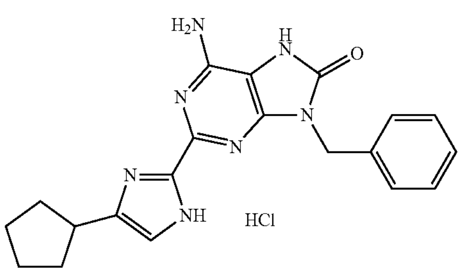 [SMILES: Nc1nc(-c2nc(C3CCCC3)c[nH]2)nc2c1[nH]c(=O)n2Cc1ccccc1 ; Cl] | 375.18 | 376 | | 1 | | ¹H NMR(DMSO-d₆, 400 MHz): δ ppm 14.45 (br. s., 1 H), 11.49 (s, 1H), 7.54 (s, 1H), 7.41 (d, J = 8 Hz, 2H), 7.31 (t, J = 8 Hz, 2H), 7.28 (t, J = 8 Hz, 1H), 7.14 (br. s., 2 H), 5.06 (s, 2 H), 3.15 (m, 1 H), 2.08-2.06 (m, 2 H), 1.74-1.62 (m, 6 H) |
| 4 | 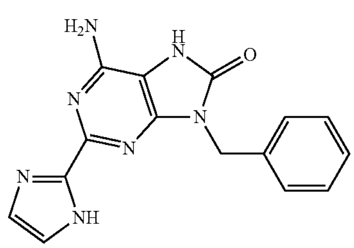 [SMILES: Nc1nc(-c2ncc[nH]2)nc2c1[nH]c(=O)n2Cc1ccccc1] | 307.12 | 308 | 1.87, V3018V3001 | 2 | >260 | ¹H NMR (DMSO-d₆, 400 MHz): δ ppm 12.34 (br. s., 1 H), 10.32 (br. s., 1 H). 7.22-7.44 (m, 5 H), 7.18 (s, 1 H), 7.01 (s, 1 H), 6.48 (br. s., 2 H), 5.00 (s, 2 H) |

TABLE 1-continued

Compounds of formula (I).

| # | STRUCTURE | Exact Mass | Mass Found [M + H] | LCMS Ret Time, Method | Synthesis method | MP (° C.) | H NMR |
|---|---|---|---|---|---|---|---|
| 5 | 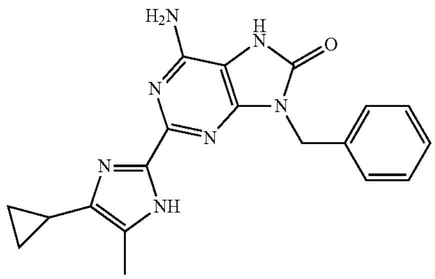 [SMILES: Cc1[nH]c(-c2nc(N)c3[nH]c(=O)n(Cc4ccccc4)c3n2)nc1C1CC1] | 361.16 | 362 | 2.35, V3018V3001 | 3 | >260 | $^1$H NMR (DMSO-d$_6$, 500 MHz): δ ppm 11.89 (br. s., 1 H), 10.24 (br. s., 1 H), 7.21-7.40 (m, 5 H), 6.51 (br. s., 2 H), 5.01 (s, 2 H), 2.24 (s, 3 H), 1.72- 1.80 (m, 1 H), 0.65-0.78 (m, 4 H) |
| 6 | 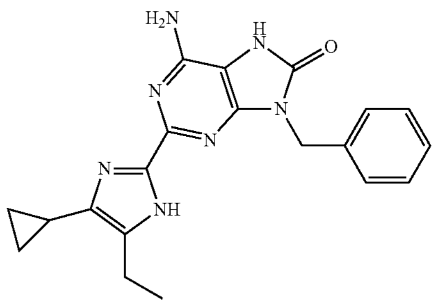 [SMILES: CCc1[nH]c(-c2nc(N)c3[nH]c(=O)n(Cc4ccccc4)c3n2)nc1C1CC1] | 375.18 | 376 | 2.52, V3018V3001 | 3 | >260 | $^1$H NMR (DMSO-d$_6$, 500 MHz): δ ppm 11.85 (br. s., 1 H), 10.26 (s, 1 H). 7.21-7.39 (m, 5 H), 6.51 (br. s., 2 H), 5.02 (s, 2 H), 2.65 (m, 2 H), 1.78 (br. s., 1 H), 1.17 (t, J = 6.5 Hz, 3 H), 0.65-0.78 (m, 4 H) |
| 7 | 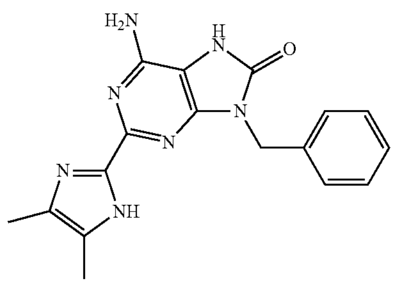 [SMILES: Cc1nc(-c2nc(N)c3[nH]c(=O)n(Cc4ccccc4)c3n2)[nH]c1C] | 335.15 | 336 | 2.1, V3018V3001 | 3 | 230 | $^1$H NMR(DMSO-d$_6$, 500 MHz): δ ppm 11.98 (br. s., 1 H), 10.27 (s, 1 H), 7.20-7.40 (m, 5 H), 6.40 (s, 2 H), 5.01 (s, 2 H), 2.10 (br. s., 6 H) |
| 8 | 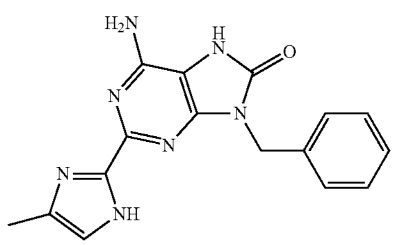 [SMILES: Cc1c[nH]c(-c2nc(N)c3[nH]c(=O)n(Cc4ccccc4)c3n2)n1] | 321.13 | 322 | 2.01, V3018V3001 | 3 | | $^1$H NMR (500 MHz, DMSO-d$_6$) δ ppm 12.00-12.17 (m, 1 H), 10.29 (s, 1 H), 7.35-7.40 (m, 2 H), 7.32 (t, J = 7.41 Hz, 2 H), 7.23-7.29 (m, 1 H), 6.66-6.90 (m, 1 H), 6.44 (br. s., 2 H), 5.00 (br. s., 2 H), 2.10-2.26 (m, 3 H). |
| 9 | 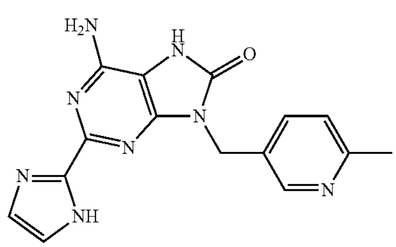 [SMILES: Cc1ccc(Cn2c(=O)[nH]c3c(N)nc(-c4ncc[nH]4)nc32)cn1] | 322.13 | 323 | 2.47, V3018V3001 | 4 | >260 | $^1$H NMR (400 MHz, DMSO-d$_6$) δ ppm 10.38 (br. s., 1 H), 8.56 (br. s., 1 H), 7.71 (d, J = 7.07 Hz, 1 H), 7.09-7.30 (m, 4 H), 6.45 (br. s., 2 H), 4.99 (s, 2 H), 1.25 (br. s., 3 H). |

TABLE 1-continued

Compounds of formula (I).

| # | STRUCTURE | Exact Mass | Mass Found [M + H] | LCMS Ret Time, Method | Synthesis method | MP (° C.) | H NMR |
|---|---|---|---|---|---|---|---|
| 10 | 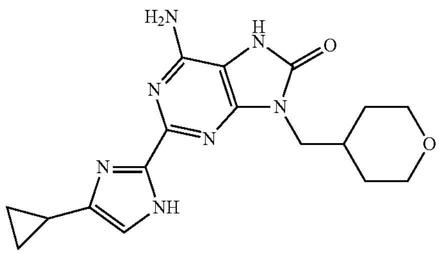 [SMILES: Nc1nc(-c2nc(C3CC3)c[nH]2)nc2c1[nH]c(=O)n2CC1CCOCC1] | 355.18 | 356 | 1.86, V3018V3001 | 4 | >260 | $^1$H NMR (500 MHz, MeOD) δ ppm 6.83 (s, 1 H), 3.95 (dd, J = 2.84, 11.35 Hz, 2 H), 3.87 (d, J = 7.57 Hz, 2 H), 3.36-3.44 (m, 2 H), 2.25-2.37 (m, 1 H), 1.89-1.98 (m, 1 H), 1.60 (dd, J = 1.89, 12.93 Hz, 2 H), 1.41-1.52 (m, 2 H), 0.88-0.96 (m, 2 H), 0.71-0.77 (m, 2 H). |
| 11 | 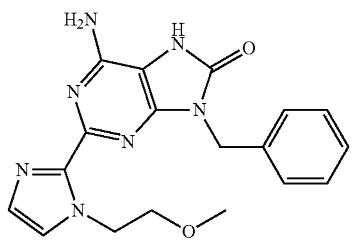 [SMILES: COCCn1ccnc1-c1nc(N)c2[nH]c(=O)n(Cc3ccccc3)c2n1] | 365.16 | 366 | 2.11, V3018V3001 | 2 | >260 | $^1$H NMR (DMSO-d$_6$, 500 MHz): δ ppm 10.47 (br. s., 1 H), 7.22-7.38 (m, 5 H), 7.20 (s, 1 H), 6.91 (s, 1 H), 6.62 (br. s., 2 H), 4.97 (s, 2 H), 4.52 (t, J = 5.4 Hz, 2 H), 3.48 (t, J = 5.4 Hz, 2 H), 3.10 (s, 3 H) |
| 12 | 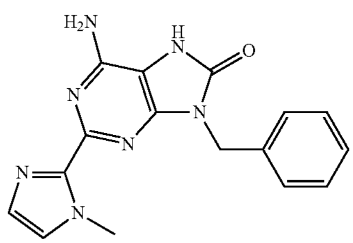 [SMILES: Cn1ccnc1-c1nc(N)c2[nH]c(=O)n(Cc3ccccc3)c2n1] | 321.13 | 322 | 2.06, V3018V3001 | 2 | >260 | $^1$H NMR (DMSO-d$_6$, 500 MHz): δ ppm 7.16-7.33 (m, 5 H), 7.10 (s, 1 H), 6.84 (s, 1 H), 6.24 (br. s., 2 H), 4.91 (s, 2 H), 3.85 (s, 3 H) |
| 15 | 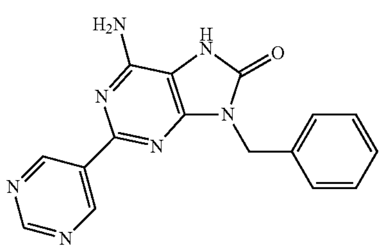 [SMILES: Nc1nc(-c2cncnc2)nc2c1[nH]c(=O)n2Cc1ccccc1] | 319.12 | 320 | 2.3, Villa | 6 | | $^1$H NMR (DMSO-d$_6$, 300 MHz): δ ppm 10.25 (br. s, 1 H), 9.47 (s, 2 H), 9.23 (s, 1 H), 7.40 (t, J = 7.2 Hz, 2 H), 7.34 (t, J = 7.2 Hz, 2 H), 7.27 (d, J = 7.2 Hz, 1 H) 6.70 (s, 2 H), 5.75 (s, 1 H), 5.02 (s, 2 H) |
| 18 | 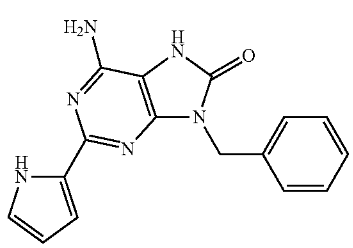 [SMILES: Nc1nc(-c2ccc[nH]2)nc2c1[nH]c(=O)n2Cc1ccccc1] | 306.12 | 307 | 2.45, Villa | 6 | | $^1$H NMR (DMSO-d$_6$, 300 MHz): δ ppm 11.10 (br. s., 1 H), 10.20 (br. s., 1 H), 7.43 (d, J = 7.1 Hz, 2 H), 7.33 (t, J = 7.1 Hz, 2 H), 7.26 (t, J = 7.1 Hz, 1 H), 6.83 (d, J = 1.5 Hz, 1 H), 6.68 (br. s., 1 H), 6.35 (s, 2 H), 6.10 (d, J = 1.5 Hz, 1 H), 4.98 (s, 2 H) |

TABLE 1-continued

Compounds of formula (I).

| # | STRUCTURE | Exact Mass | Mass Found [M + H] | LCMS Ret Time, Method | Synthesis method | MP (° C.) | H NMR |
|---|---|---|---|---|---|---|---|
| 19 | 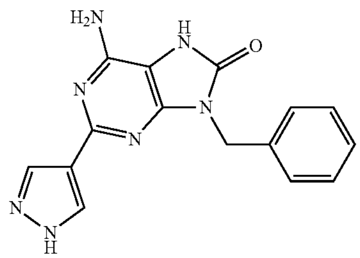 [SMILES: Nc1nc(-c2cn[nH]c2)nc2c1[nH]c(=O)n2Cc1ccccc1] | 307.12 | 308 | 1.82, Villa | 6 | | $^1$H NMR (DMSO-d$_6$, 300 MHz): δ ppm 12.97 (br. s., 1 H), 10.25 (br. s., 1 H), 8.02 (br. s., 2 H), 7.18-7.44 (m, 5 H), 6.42 (s, 2 H), 4.95 (s, 2 H) |
| 20 | 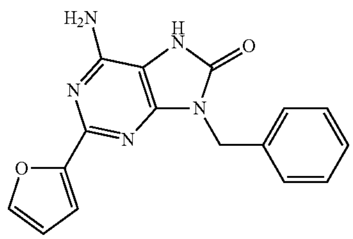 [SMILES: Nc1nc(-c2ccco2)nc2c1[nH]c(=O)n2Cc1ccccc1] | 307.11 | 308 | 2.57, Villa | 6 | | $^1$H NMR (DMSO-d$_6$, 300 MHz): δ ppm 10.60 (br. s., 1 H), 7.76 (br.s, 1 H), 7.19-7.40 (m, 5 H), 7.00 (d, J = 3.3 Hz, 1 H), 6.66 (s, 2 H), 6.59 (dd, J = 3.3, 1.8 Hz, 1 H), 5.0 (s, 2 H) |
| 23 | 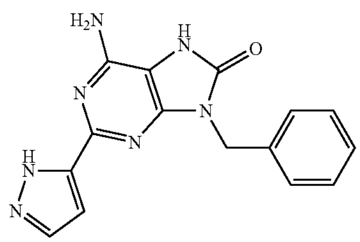 [SMILES: Nc1nc(-c2ccn[nH]2)nc2c1[nH]c(=O)n2Cc1ccccc1] | 307.12 | 308 | 2.03, V3018V3001 | 5 | >260 | $^1$H NMR (500 MHz, DMSO-d$_6$) δ ppm 12.84-13.37 (m, 1 H), 10.30 (br. s., 1 H), 7.23-7.76 (m. 6 H), 6.70 (br. s., 1 H), 6.49 (br. s., 2 H), 4.98 (s, 2 H). |
| 24 | 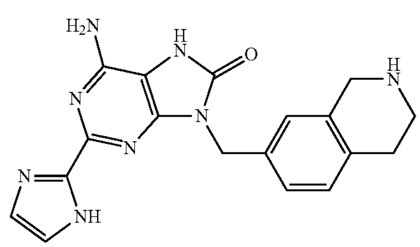 [SMILES: Nc1nc(-c2ncc[nH]2)nc2c1[nH]c(=O)n2Cc1ccc2c(c1)CNCC2] | 362.16 | 363 | 2.20 V3018V3001 | 4 | 240 | $^1$H NMR (DMSO-d$_6$, 400 MHz): δ ppm 12.25 (br. s., 1 H), 7.18 (d, J = 8.1 Hz, 1 H), 6.99-7.14 (m, 4 H), 6.50 (s, 2 H), 4.94 (s, 2 H), 3.93 (s, 2 H), 3.01-307 (m, 2 H), 2.72 (t, J = 5.6 Hz, 2 H) |
| 25 | 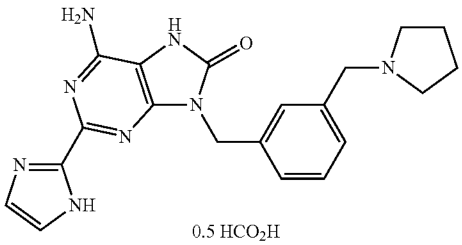 [SMILES: Nc1nc(-c2ncc[nH]2)nc2c1[nH]c(=O)n2Cc1cccc(CN2CCCC2)c1] | 390.19 | 391 | 2.47 V3018V3001 | 4 | 196 | $^1$H NMR (DMSO-d$_6$, 400 MHz): δ ppm 12.13 (br. s, 1 H), 10.38 (br. s, 1 H), 8.15 (br. s., 0.49 H, formate salt pic), 7.39 (br. s., 1 H), 7.18-7.34 (m, 3 H), 7.09 (br. s., 2 H), 6.50 (br. s., 2 H), 5.01 (br. s., 2 H), 3.71 (br. s, 2 H), 2.50-2.61 (m, 4 H), 1.67 (br. s., 4 H) |

TABLE 1-continued

Compounds of formula (I).

| # | STRUCTURE | Exact Mass | Mass Found [M + H] | LCMS Ret Time, Method | Synthesis method | MP (° C.) | H NMR |
|---|---|---|---|---|---|---|---|
| 26 | (structure with 0.5 HCO₂H) | 362.16 | 363 | 1.90 V3018V3001 | 4 | >260 | ¹H NMR (DMSO-d₆, 400 MHz): δ ppm 12.05 (s br, 1 H), 10.27 (s, 1 H), 8.56 (d, J = 1.8 Hz, 1 H), 8.15 (s, 0.59 H, formate salt pic), 7.70 (dd, J = 8.2, 1.8 Hz, 1 H), 7.20 (d, J = 8.2 Hz, 1 H), 6.93 (s br, 1 H), 6.49 (s br, 2 H), 4.97 (s, 2 H), 2.41 (s, 3 H), 1.78-1.90 (m, 1 H), 0.70-0.87 (m, 2 H), 0.64-0.70 (m, 2 H) |
| 27 | (structure) | 351.14 | 352 | 1.78 V3018V3001 | 2 | 260 | ¹H NMR (DMSO-d₆, 500 MHz): δ ppm 10.37 (s, 1 H), 7.23-7.38 (m, 5 H), 7.21 (d, J = 0.9 Hz, 1 H), 6.91 (d, J = 0.9 Hz, 1 H), 6.58 (br. s., 2 H), 4.96 (s, 2 H), 4.81 (t, J = 5.7 Hz, 1 H), 4.41 (t, J = 5.7 Hz, 2 H), 3.59 (q, J = 5.7 Hz, 2 H) |
| 28 | (structure) | 363.18 | 364 | 2.51 V3018V3001 | 2 | >260 | ¹H NMR (DMSO-d₆, 500 MHz): δ ppm 11.78-12.24 (m, 1 H), 10.28 (s, 1 H), 7.07-7.47 (m, 5 H), 6.21-6.93 (m, 3 H), 5.01 (s, 2 H), 1.13-1.45 (m, 9 H) |
| 29 | (structure) | 349.17 | 350 | 2.35 V3018V3001 | 2 | >260 | ¹H NMR (DMSO-d₆, 500 MHz): δ ppm 11.80-12.14 (m, 1 H), 10.41 (br. s., 1 H), 7.06-7.70 (m, 5 H), 6.65-6.89 (m, 1 H), 6.37-6.62 (m, 2 H), 4.89-5.21 (m, 2 H), 2.73-3.16 (m, 1 H), 1.04-1.31 (m, 6 H) |
| 30 | (structure) | 335.15 | 336 | 2.18 V3018V3001 | 2 | >260 | ¹H NMR (DMSO-d₆, 500 MHz): δ ppm 11.82-12.28 (m, 1 H), 10.47 (br. s., 1 H), 7.08-7.56 (m, 5 H), 6.63-7.01 (m, 1 H), 6.38-6.59 (m, 2 H), 4.78-5.07 (m, 2 H), 2.53-2.69 (m, 2 H), 0.95-1.35 (m, 3 H) |

TABLE 1-continued

Compounds of formula (I).

| # | STRUCTURE | Exact Mass | Mass Found [M + H] | LCMS Ret Time, Method | Synthesis method | MP (° C.) | H NMR |
|---|-----------|------------|---------------------|------------------------|------------------|-----------|-------|
| 31 | 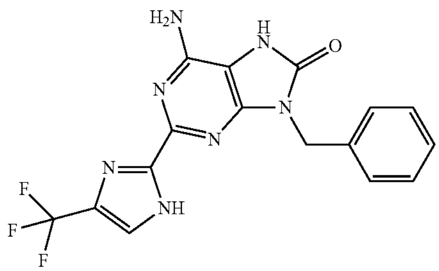 [SMILES: Nc1nc(-c2nc(C(F)(F)F)c[nH]2)nc2c1[nH]c(=O)n2Cc1ccccc1] | 375.11 | 376 | 2.38 V3018V3001 | 2 | >260 | ¹H NMR (DMSO-d₆, 500 MHz): δ ppm 13.07 (br. s., 1 H), 10.46 (br. s., 1 H), 7.83 (s, 1 H), 7.39 (d, J = 8.2 Hz, 2 H), 7.32 (t, J = 8.2 Hz, 2 H), 7.26 (t, J = 8.2 Hz, 1 H), 6.65 (br. s., 2 H), 4.98 (s, 2 H) |
| 32 | 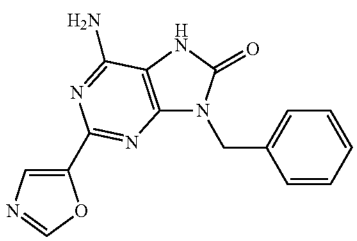 [SMILES: Nc1nc(-c2cnco2)nc2c1[nH]c(=O)n2Cc1ccccc1] | 308.10 | 309 | 2.06 V3018V3001 | 5 | | ¹H NMR (DMSO-d₆, 500 MHz): δ ppm 10.44 (br. s., 1 H), 8.45 (s, 1 H), 7.63 (s, 1 H), 7.16-7.37 (m, 5 H), 6.70 (br. s., 2 H), 4.96 (s, 2 H) |
| 33 | 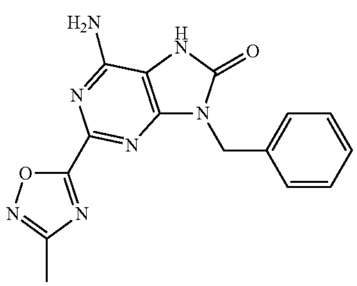 [SMILES: Cc1noc(-c2nc(N)c3[nH]c(=O)n(Cc4ccccc4)c3n2)n1] | 323.11 | 324 | 2.23 V3018V3001 | 5 | >250 | ¹H NMR (DMSO-d₆, 500 MHz): δ ppm 10.72 (br. s., 1 H), 7.11-7.56 (m, 5 H), 6.94 (br. s., 2 H), 5.00 (br. s., 2 H), 2.41 (s, 3 H) |
| 34 | 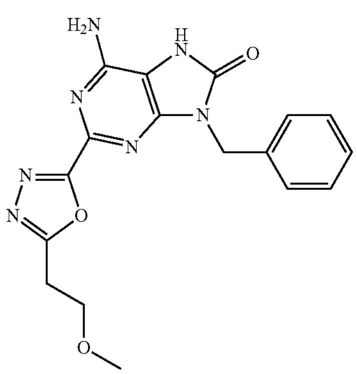 [SMILES: COCCc1nnc(-c2nc(N)c3[nH]c(=O)n(Cc4ccccc4)c3n2)o1] | 367.14 | 368 | 2.27 V3018V3001 | 5 | >250 | ¹H NMR (DMSO-d₆, 500 MHz): δ ppm 10.71 (br. s., 1 H), 7.16-7.49 (m, 5 H), 6.96 (br. s., 2 H), 5.01 (s, 2 H), 3.72 (t, J = 6.3 Hz, 2 H), 3.24 (s, 3 H), 3.01 (t, J = 6.3 Hz, 2 H) |
| 35 | 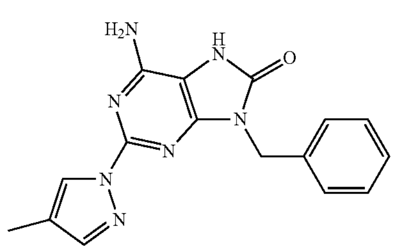 [SMILES: Cc1cnn(-c2nc(N)c3[nH]c(=O)n(Cc4ccccc4)c3n2)c1] | 321.13 | 322 | 2.42 V3018V3001 | 7 | >260 | ¹H NMR (DMSO-d₆, 500 MHz): δ ppm 10.31 (br. s., 1 H), 8.24 (s, 1 H), 7.51 (s, 1 H), 7.18-7.40 (m, 5 H), 6.78 (br. s., 2 H), 4.96 (s, 2 H), 2.08 (s, 3H) |

TABLE 1-continued

Compounds of formula (I).

| # | STRUCTURE | Exact Mass | Mass Found [M + H] | LCMS Ret Time, Method | Synthesis method | MP (° C.) | H NMR |
|---|---|---|---|---|---|---|---|
| 36 | 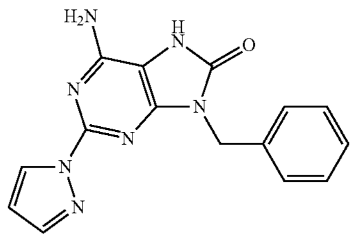 [SMILES: Nc1nc(-n2cccn2)nc2c1[nH]c(=O)n2Cc1ccccc1] | 307.12 | 308 | 2.25 V3018V3001 | 7 | >260 | ¹H NMR (DMSO-d₆, 500 MHz): δ ppm 10.33 (br. s., 1 H), 8.46 (d, J = 2.5 Hz, 1 H), 7.70 (s, 1 H), 7.20-7.40 (m, 5 H), 6.82 (br. s., 2 H), 6.48 (d, J = 3.8 Hz, 1 H), 4.97 (s, 2 H) |
| 37 | 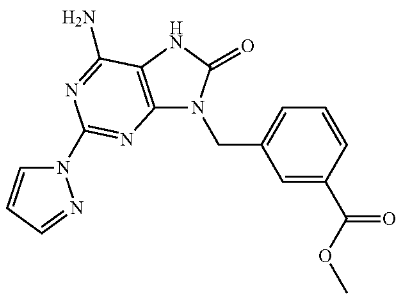 [SMILES: COC(=O)c1cccc(Cn2c(=O)[nH]c3c(N)nc(-n4cccn4)nc32)c1] | 365.12 | 366 | 2.24 V3018V3001 | 8 | | ¹H NMR (DMSO-d₆, 400 MHz): δ (ppm) 9.80 (br. s., 1 H), 8.47 (d, J = 2.5 Hz, 1 H), 7.99 (s, 1 H), 7.87 (d, J = 7.6 Hz, 1 H), 7.70 (s, 1 H), 7.65 (d, J = 7.6 Hz, 1 H), 7.50 (t, J = 7.6 Hz, 1 H), 6.84 (br. s., 2 H), 6.43-6.63 (m, 1 H), 5.04 (s, 2 H), 3.83 (s, 3 H) |
| 38 | 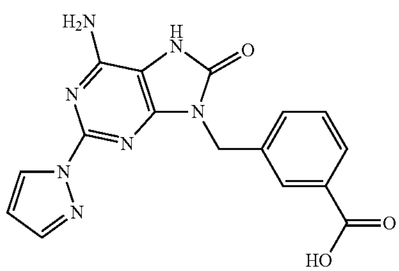 [SMILES: Nc1nc(-n2cccn2)nc2c1[nH]c(=O)n2Cc1cccc(C(=O)O)c1] | 351.11 | 352 | 2.27 V3014V3001 | 8 | 332 | ¹H NMR (DMSO-d₆, 400 MHz): δ (ppm) 13.01 (br. s., 1 H), 10.46 (br. s., 1 H), 8.47 (s, 1 H), 7.95 (s, 1 H), 7.84 (d, J = 7.6 Hz, 1 H), 7.69 (s, 1 H), 7.60 (d, J = 7.6 Hz, 1 H), 7.46 (t, J = 7.6 Hz, 1 H), 6.87 (br. s., 2 H), 6.48 (s, 1 H), 5.03 (s, 2 H) |
| 39 | 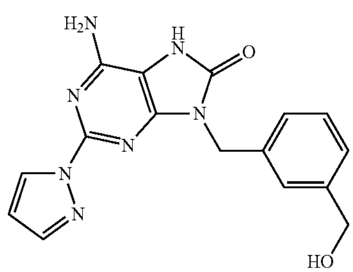 [SMILES: Nc1nc(-n2cccn2)nc2c1[nH]c(=O)n2Cc1cccc(CO)c1] | 337.13 | 338 | 1.87 V3018V3001 | 8 | | ¹H NMR (DMSO-d₆, 500 MHz): δ (ppm) 10.28 (br. s., 1 H), 8.46 (s, 1 H), 7.70 (s, 1 H), 7.10-7.37 (m, 4 H), 6.82 (br. s., 2 H), 6.35-6.57 (m, 1 H), 5.17 (t, J = 5.7 Hz, 1 H), 4.96 (s, 2 H), 4.45 (d, J = 5.7 Hz, 2 H) |
| 40 | 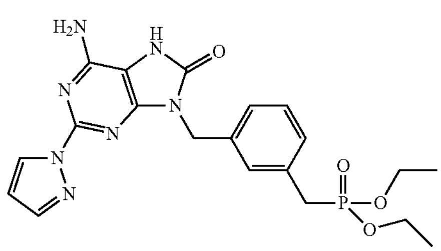 [SMILES: CCOP(=O)(Cc1cccc(Cn2c(=O)[nH]c3c(N)nc(-n4cccn4)nc32)c1)OCC] | 457.16 | 458 | 2.13 V3018V3001 | 8 | 218 | ¹H NMR (DMSO-d₆, 500 MHz): δ (ppm) 10.41 (br. s., 1 H), 8.46 (br. s., 1 H), 7.69 (s, 1 H), 7.04-7.38 (m, 4 H), 6.85 (br. s., 2 H), 6.47 (br. s., 1 H), 4.95 (br. s., 2 H), 3.85 (quin, J = 7.0 Hz, 4 H), 3.18 (d, J = 21.4 Hz, 2 H), 1.06 (t, J = 7.0 Hz, 6 H) |

TABLE 1-continued

Compounds of formula (I).

| # | STRUCTURE | Exact Mass | Mass Found [M + H] | LCMS Ret Time, Method | Synthesis method | MP (° C.) | H NMR |
|---|---|---|---|---|---|---|---|
| 41 | (structure: 6-amino-2-(pyrazol-1-yl)-9-(3-(phosphonomethyl)benzyl)-purin-8(7H)-one · HCl) | 401.10 | 402 | 5.40 V2012V2002 | 8 | 101 | $^1$H NMR (DMSO-$d_6$, 400 MHz): δ (ppm) 10.43 (s, 1 H), 8.46 (d, J = 2.5 Hz, 1 H), 7.69 (s, 1 H), 7.10-7.31 (m, 4 H), 6.84 (br. s., 2 H), 6.47 (dd, J = 2.5, 1.5 Hz, 1 H), 6.29 (br. s, 2 H), 4.90 (s, 2 H), 2.92 (d, J = 21.2 Hz, 2 H) |
| 42 | (structure: 6-amino-2-(1H-pyrazol-3-yl)-9-((6-methylpyridin-1-oxide-2-yl)methyl)purin-8(7H)-one) | 338.12 | 339 | 2.45 V3014V3001 | 7 | | $^1$H NMR (DMSO-$d_6$, 500 MHz): δ (ppm) 10.20 (br. s., 1 H), 8.37 (d, J = 2.2 Hz, 1 H), 7.65 (s, 1 H), 7.48 (d, J = 6.9 Hz, 1 H), 7.19 (t, J = 6.9 Hz, 1 H), 6.82-7.00 (m, 3 H), 6.44 (dd, J = 2.4, 1.7 Hz, 1 H), 4.95-5.14 (m, 2 H), 2.43 (s, 3 H) |
| 43 | (structure: 6-amino-2-(1H-pyrazol-3-yl)-9-(imidazo[1,2-a]pyridin-2-ylmethyl)purin-8(7H)-one) | 347.12 | 348 | 2.54 V3014V3001 | 7 | | $^1$H NMR (DMSO-$d_6$, 400 MHz): δ (ppm) 12.48-13.42 (m, 1 H), 9.90-10.57 (m, 1 H), 8.44 (d, J = 9.1 Hz, 1 H), 7.37-7.99 (m, 3 H), 7.19 (t, J = 9.1 Hz, 1 H), 6.83 (t, J = 9.1 Hz, 1 H), 6.69 (br. s., 1 H), 6.47 (br. s., 2 H), 5.12 (br. s., 2 H) |
| 44 | (structure: 6-amino-2-(1H-pyrazol-3-yl)-9-(3-(methoxycarbonyl)benzyl)purin-8(7H)-one) | 365.12 | 366 | 3.05 V3014V3001 | 7 | | $^1$H NMR (DMSO-$d_6$, 400 MHz): δ (ppm) 12.32-13.87 (m, 1 H), 9.94-10.53 (m, 1 H), 7.4-8.26 (m, 5 H), 6.61-6.89 (m, 1 H), 6.28-6.59 (m, 2 H), 5.05 (s, 2 H), 3.83 (s, 3 H) |
| 45 | (structure: 6-amino-2-(1H-pyrazol-3-yl)-9-(3-carboxybenzyl)purin-8(7H)-one) | 351.11 | 352 | 2.13 V3014V3001 | 7 | | $^1$H NMR (DMSO-$d_6$, 400 MHz): δ (ppm) 13.06 (br. s., 2 H), 10.32 (br. s., 1 H), 7.97 (s, 1 H), 7.83 (d, J = 7.6 Hz, 1 H), 7.69 (d, J = 7.6 Hz, 1 H), 7.57 (br. s., 1 H), 7.46 (t, J = 7.6 Hz, 1 H), 6.72 (d, J = 1.5 Hz, 1 H), 6.48 (s, 2 H), 5.04 (s, 2 H) |

TABLE 1-continued

Compounds of formula (I).

| # | STRUCTURE | Exact Mass | Mass Found [M + H] | LCMS Ret Time, Method | Synthesis method | MP (° C.) | H NMR |
|---|---|---|---|---|---|---|---|
| 46 | 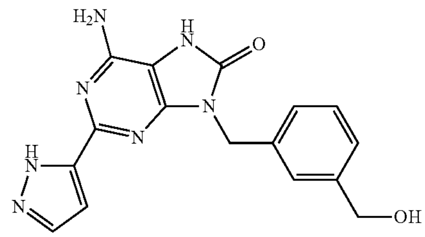 [SMILES: Nc1nc(-c2ccn[nH]2)nc2c1[nH]c(=O)n2Cc1cccc(CO)c1] | 337.13 | 338 | 1.63 V3018V3001 | 7 | >260 | $^1$H NMR (DMSO-d$_6$, 500 MHz): δ (ppm) 12.48-13.52 (m, 1 H), 9.83-10.74 (m, 1 H), 7 01-7.98 (m, 5 H), 6.22-6.84 (m, 3 H), 5.17 (t, J = 5.7 Hz, 1 H), 4.97 (s, 2 H), 4.44 (d, J = 5.7 Hz, 2 H) |
| 47 | 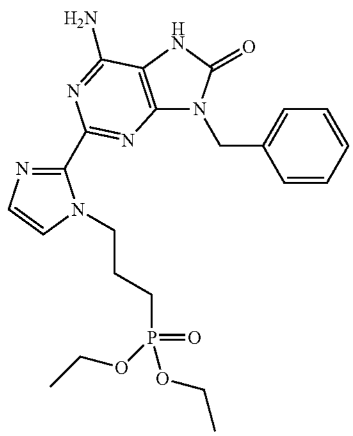 [SMILES: CCOP(=O)(CCCn1ccnc1-c1nc(N)c2[nH]c(=O)n(Cc3ccccc3)c2n1)OCC] | 485.19 | 486 | 2.11 V3018V3001 | 2 | | $^1$H NMR (DMSO-d$_6$, 400 MHz): δ (ppm) 10.45 (s, 1 H), 7.13-7.54 (m, 6 H), 6.94 (s, 1 H), 6.62 (br. s., 2H), 4.98 (s, 2 H), 4.33-4.48 (m, 2 H), 3.82-4.02 (m, 4 H), 1.76-1.92 (m, 2 H), 1.47-1.66 (m, 2 H), 1.15 (t, J = 6.8 Hz, 6 H) |
| 48 | 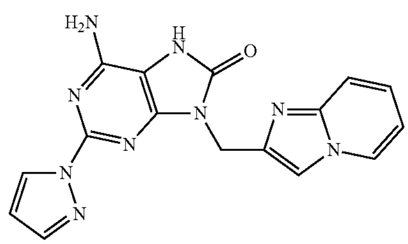 [SMILES: Nc1nc(-n2cccn2)nc2c1[nH]c(=O)n2Cc1cn2ccccc2n1] | 347.12 | 348 | 1.81 V3018V3001 | 8 | | $^1$H NMR (DMSO-d$_6$, 400 MHz): δ (ppm) 10.35 (br. s., 1 H), 8.27-8.53 (m, 2 H), 7.77 (s, 1 H), 7.67 (s, 1 H), 7.47 (d, J = 9.1 Hz, 1 H), 7.15-7.27 (m, 1 H), 6.76-6.88 (m, 3 H), 6.36-6.53 (m, 1 H), 5.09 (s, 2 H) |
| 49 | 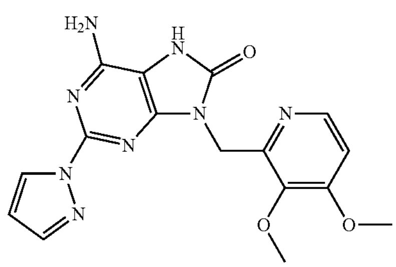 [SMILES: COc1ccnc(Cn2c(=O)[nH]c3c(N)nc(-n4cccn4)nc32)c1OC] | 368.13 | 369 | 1.94 V3018V3001 | 8 | >260 | $^1$H NMR (DMSO-d$_6$, 500 MHz): δ (ppm) 9.42-10.55 (m, 1 H), 8.35 (d, J = 2.5 Hz, 1 H), 8.01 (d, J = 5.4 Hz, 1 H), 7.65 (s, 1 H), 7.02 (d, J = 5.4 Hz, 1 H), 6.80 (br. s., 2 H), 6.36-6.55 (m, 1 H), 5.07 (s, 2 H), 3.81-3.96 (m, 6 H) |
| 50 | 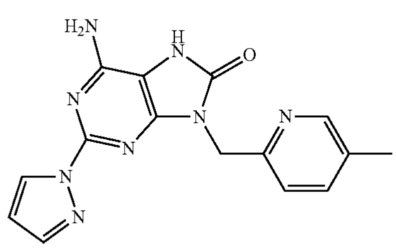 [SMILES: Cc1ccc(Cn2c(=O)[nH]c3c(N)nc(-n4cccn4)nc32)nc1] | 322.13 | 323 | 2.78 V3014V3001 | 8 | >260 | $^1$H NMR (DMSO-d$_6$, 500 MHz): δ (ppm) 10.31 (br. s., 1 H), 8.49 (d, J = 8.5 Hz, 2 H), 7.71 (s, 1 H), 7.65 (d, J = 7.6 Hz, 1 H), 7.21 (d, J = 7.6 Hz, 1 H), 6.82 (br. s., 2 H), 6.50 (br. s., 1 H), 4.95 (s, 2 H), 2.39 (s, 3 H) |

TABLE 1-continued

Compounds of formula (I).

| # | STRUCTURE | Exact Mass | Mass Found [M + H] | LCMS Ret Time, Method | Synthesis method | MP (° C.) | H NMR |
|---|---|---|---|---|---|---|---|
| 51 | 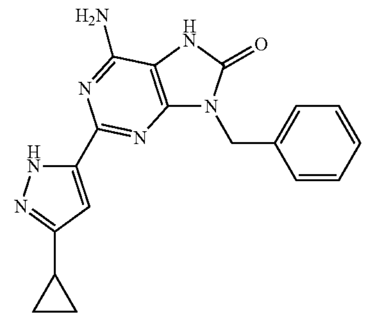 [SMILES: Nc1nc(-c2cc(C3CC3)n[nH]2)nc2c1[nH]c(=O)n2Cc1ccccc1] | 347.15 | 348 | 2.35 V3018V3001 | 7 | >260 | ¹H NMR (DMSO-d₆, 500 MHz): δ (ppm) 12.36-12.99 (m, 1 H), 10.33 (br. s., 1 H), 6.94-7.75 (m, 5 H), 5.99-6.73 (m, 3 H), 4.97 (s, 2 H), 1.81-1.97 (m, 1 H), 0.54-1.02 (m, 4 H) |
| 52 | 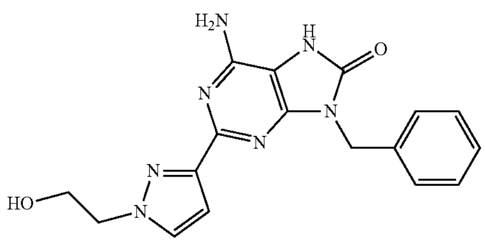 [SMILES: Nc1nc(-c2ccn(CCO)n2)nc2c1[nH]c(=O)n2Cc1ccccc1] | 351.14 | 352 | 1.93 V3018V3001 | 7 | | ¹H NMR (DMSO-d₆, 400 MHz): δ (ppm) 10.23 (br. s., 1 H), 7.68 (d, J = 2.0 Hz, 1 H), 7.15-7.40 (m, 5 H), 6.72 (d, J = 2.0 Hz, 1 H), 6.46 (s, 2 H), 4.97 (s, 2 H), 4.87 (t, J = 5.1 Hz, 1 H), 4.17 (t, J = 5.1 Hz, 2 H), 3.75 (q, J = 5.1 Hz, 2 H) |
| 53 | 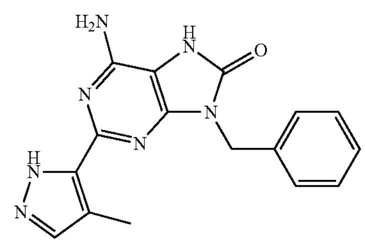 [SMILES: Cc1cn[nH]c1-c1nc(N)c2[nH]c(=O)n(Cc3ccccc3)c2n1] | 321.13 | 322 | 2.26 V3018V3001 | 7 | 192 | ¹H NMR (DMSO-d₆, 500 MHz): δ (ppm) 12.94 (br. s., 1 H), 10.28 (s, 1 H), 7.17-7.49 (m, 6 H), 6.41 (br. s., 2 H), 4.97 (s, 2 H), 2.28-2.39 (m, 3 H) |
| 54 | 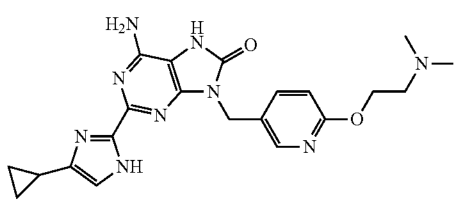 [SMILES: CN(C)CCOc1ccc(Cn2c(=O)[nH]c3c(N)nc(-c4nc(C5CC5)c[nH]4)nc32)cn1] | 435.21 | 436 | 1.32 V3018V3001 | 2 | 211 | ¹H NMR (DMSO-d₆, 500 MHz): δ (ppm) 11.90-12.42 (m, 1 H), 10.14 (br. s., 1 H), 7.85-8.01 (m, 1 H), 7.35-7.56 (m, 1 H), 6.21-7.07 (m, 4 H), 4.65-4.77 (m, 2 H), 3.86-3.94 (m, 2 H), 2.38-2.44 (m, 2 H), 2.04 (s, 6 H), 1.77-1.89 (m, 1 H), 0.60-0.92 (m, 4 H) |
| 55 | 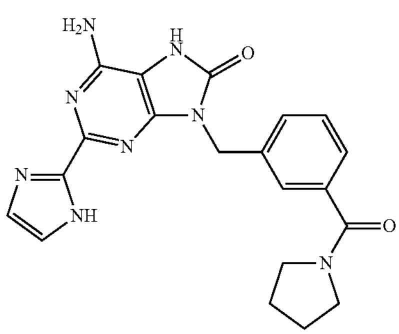 [SMILES: Nc1nc(-c2ncc[nH]2)nc2c1[nH]c(=O)n2Cc1cccc(C(=O)N2CCCC2)c1] | 404.17 | 405 | 2.80 V3014V3001 | 2 | 218 | ¹H NMR (DMSO-d₆, 400 MHz): δ (ppm) 12.52 (br. s., 1 H), 10.32 (s, 1 H), 7.59 (s, 1 H), 7.46-7.51 (m, 1 H), 7.34-7.45 (m, 2 H), 7.12 (br. s., 2 H), 6.49 (s, 2 H), 4.94-5.25 (m, 2 H), 3.41 (t, J = 7.1 Hz, 2 H), 3.20-3.29 (m, 2 H), 1.79 (quin, J = 7.1 Hz, 2 H), 1.64 (quin, J = 7.1 Hz, 2 H) |

TABLE 1-continued

Compounds of formula (I).

| # | STRUCTURE | Exact Mass | Mass Found [M + H] | LCMS Ret Time, Method | Synthesis method | MP (° C.) | H NMR |
|---|---|---|---|---|---|---|---|
| 57 | 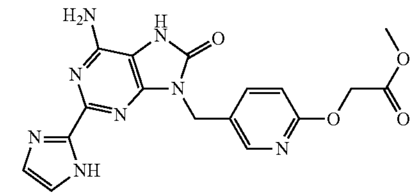 [SMILES: COC(=O)COc1ccc(Cn2c(=O)[nH]c3c(N)nc(-c4ncc[nH]4)nc32)cn1] | 396.13 | 397 | 1.79 V3018V3001 | 2 | >260 | $^1$H NMR (DMSO-d$_6$, 500 MHz): δ (ppm) 12.47 (br. s., 1 H), 10.30 (br. s., 1 H), 8.25 (br. s., 1 H), 7.84 (d, J = 8.2 Hz, 1 H), 7.13 (br. s., 2 H), 6.90 (d, J = 8.2 Hz, 1 H), 6.50 (br. s., 2 H), 4.94 (br. s., 2 H), 4.87 (br. s., 2 H), 3.63 (s, 3 H) |
| 58 | 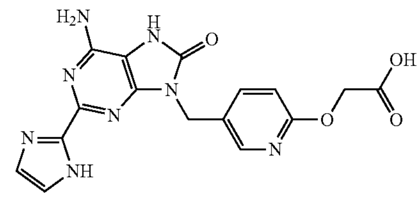 [SMILES: Nc1nc(-c2ncc[nH]2)nc2c1[nH]c(=O)n2Cc1ccc(OCC(=O)O)nc1] | 382.11 | 383 | 2.00 V3014V3001 | 2 | >260 | $^1$H NMR (DMSO-d$_6$, 500 MHz): δ (ppm) 11.87-13.45 (m, 2 H), 10.50 (br. s., 1 H), 8.27 (br. s., 1 H), 7.83 (d, J = 7.6 Hz, 1 H), 7.22 (br. s., 2 H), 6.86 (d, J = 7.6 Hz, 1 H), 6.61 (br. s., 2 H), 4.94 (br. s., 2 H), 4.77 (br. s., 2 H) |
| 60 | 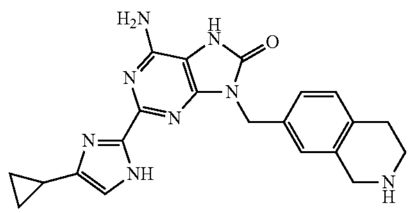 [SMILES: Nc1nc(-c2nc(C3CC3)c[nH]2)nc2c1[nH]c(=O)n2Cc1ccc2c(c1)CNCC2] | 402.19 | 403 | 2.61 V3014V3001 | 2 | 242 | $^1$H NMR (DMSO-d$_6$, 400 MHz): δ (ppm) 8.98-12.14 (m, 1 H), 8.21 (s, 1 H), 6.04-7.47 (m, 6 H), 4.95 (br. s., 2 H), 4.02 (br. s., 2 H), 3.13 (br. s., 2 H), 2.79 (br. s., 2 H), 1.67-1.97 (m, 1 H), 0.42-0.94 (m, 4 H) |
| 61 | 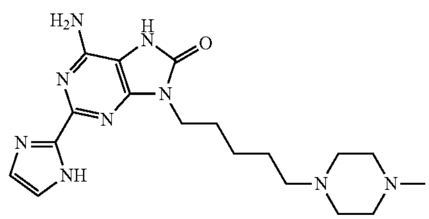 [SMILES: CN1CCN(CCCCCn2c(=O)[nH]c3c(N)nc(-c4ncc[nH]4)nc32)CC1] | 385.23 | 386 | 2.14 V3014V3001 | 2 | | $^1$H NMR (DMSO-d$_6$, 400 MHz): δ (ppm) 11.85 (br. s., 1 H), 10.32 (s, 1 H), 7.09 (s, 2 H), 6.46 (s, 2 H), 3.81 (t, J = 7.2 Hz, 2 H), 2.30-2.48 (m, 10 H), 2.27 (s, 3 H), 1.74 (quin, J = 7.2 Hz, 2 H), 1.49 (quin, J = 7.2 Hz, 2 H), 1.20-1.36 (m, 2 H) |
| 62 | 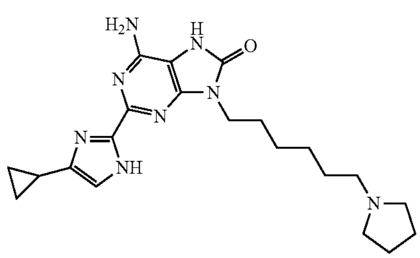 [SMILES: Nc1nc(-c2nc(C3CC3)c[nH]2)nc2c1[nH]c(=O)n2CCCCCCN1CCCC1] | 410.25 | 411 | 1.67 V3018V3001 | 2 | 174 | $^1$H NMR (DMSO-d$_6$, 500 MHz): δ (ppm) 11.91 (br. s., 1 H), 10.29 (br. s., 1 H), 6.84 (br. s., 1 H), 6.49 (br. s., 2 H), 3.79 (t, J = 6.9 Hz, 2 H), 2.52-2.70 (m, 6 H), 1.80-1.90 (m, 1 H), 1.71 (br. s., 5 H), 1.39-1.52 (m, 2 H), 1.17-1.38 (m, 5 H), 0.51-0.91 (m, 4 H) |
| 63 | 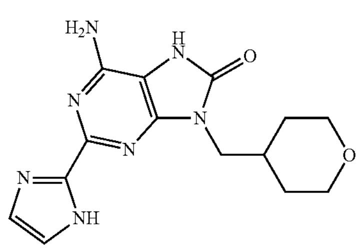 [SMILES: Nc1nc(-c2ncc[nH]2)nc2c1[nH]c(=O)n2CC1CCOCC1] | 315.14 | 316 | 2.37 V3014V3001 | 2 | >260 | $^1$H NMR (DMSO-d$_6$, 400 MHz): δ (ppm) 12.35 (br. s., 1 H), 10.24 (br. s., 1 H), 7.11 (br. s., 2 H), 6.44 (s, 2 H), 3.78-3.87 (m, 2 H), 3.70 (d, J = 7.1 Hz, 2 H), 3.24 (t, J = 10.9 Hz, 2 H), 1.99-2.18 (m, 1 H), 1.08-1.76 (m, 4 H) |

Analytical Methods.

All compounds were characterized by LC-MS. The following LC-MS methods were used:

Method VILLA:

All analyses were performed using an Agilent 1100 series LC/MSD quadrupole coupled to an Agilent 1100 series liquid chromatography (LC) system consisting of a binary pump with degasser, autosampler, thermostated column compartment and diode array detector. The mass spectrometer (MS) was operated with an atmospheric pressure electro-spray ionisation (API-ES) source in positive ion mode. The capillary voltage was set to 3000 V, the fragmentor voltage to 70 V and the quadrupole temperature was maintained at 100° C. The drying gas flow and temperature values were 12.0 L/min and 350° C. respectively. Nitrogen was used as the nebulizer gas, at a pressure of 35 psig. Data acquisition was performed with Agilent Chemstation software.

In addition to the general procedure, analyses were carried out on a YMC pack ODS-AQ C18 column (50 mm long×4.6 mm i.d.; 3 μm particles) at 35° C., with a flow rate of 2.6 mL/min. A gradient elution was performed from 95% (water+0.1% formic acid)/5% Acetonitrile to 5% (water+0.1% formic acid)/95% Acetonitrile in 4.80 minutes, then the final mobile phase composition was held for an additional 1.00 min. The standard injection volume was 2 μL. Acquisition ranges were set to 190-400 nm for the UV-PDA detector and 100-1400 m/z for the MS detector.

Method B

ACQUITY UPLC System with SQD-detector

Mobile Phase: A: methanol, B: 10 mM Ammonium acetate in 90% water and 10% Acetonitrile Column: Type column: Aquity UPLC BEH C18 1.7 μm 2.1×50 mm Column (Waters No 186002350), Temperature: 70° C. Gradient timetable. Flow: 0.7 ml/min, Acquisition stop: 1.8 min. Stop time: 2 min.

| Time (min.) | % A | % B | Flow (ml/min.) |
|---|---|---|---|
| 0.00 | 5 | 95 | 0.7 |
| 1.30 | 95 | 5 | 0.7 |
| 1.50 | 95 | 5 | 0.7 |
| 1.70 | 5 | 95 | 0.7 |
| 2.00 | 5 | 95 | 0.7 |

Injection Vol.: 0.75 μl. Inject Type: Partial Loop With Needle Overfill

Start wavelength: 210 nm. End wavelength: 400 nm. Resolution: 1.2 nm. Sampling Rate: 20 points/sec MS-Method:

Function 1:

Ion Mode: ES+, Data Format: Centroid

Start Mass: 160. End Mass: 1000

Scan time (sec): 0.1, Start Time (min): 0.0, End Time (min): 2.0, Cone Voltage (V): 30

Function 2:

Ion Mode: ES−, Data Format: Centroid, Start Mass: 160, End Mass: 1000

Scan time (sec): 0.1, Start Time (min): 0.0, End Time (min): 2.0, Cone Voltage (V): 30, Flow in MS: 700 μl/min General Procedure VDR1 (for Methods V100xV10xx.olp and V200xV20xx.olp)

The HPLC measurement was performed using an Alliance HT 2795 (Waters) system comprising a quaternary pump with degasser, an autosampler, a diode-array detector (DAD) and a column as specified in the respective methods below, the column is hold at a temperature of 30° C. Flow from the column was split to a MS spectrometer. The MS detector was configured with an electrospray ionization source. The capillary needle voltage was 3 kV and the source temperature was maintained at 100° C. on the LCT (Time of Flight Zspray™ mass spectrometer from Waters—for methods V100xV10xx.olp), and 3.15 kV at 110° C. on the ZQ™ (simple quadrupole Zspray™ mass spectrometer from Waters—for methods V200xV20xx.olp). Nitrogen was used as the nebulizer gas. Data acquisition was performed with a Waters-Micromass MassLynx-Openlynx data system.

General Procedure VDR2 (for Methods V300xV30xx.olp)

The LC measurement was performed using a UPLC (Ultra Performance Liquid Chromatography) Acquity (Waters) system comprising a binary pump with degasser, an autosampler, a diode-array detector (DAD) and a column as specified in the respective methods below, the column is hold at a temperature of 40° C. Flow from the column was brought to a MS detector. The MS detector was configured with an electrospray ionization source. The capillary needle voltage was 3 kV and the source temperature was maintained at 130° C. on the Quattro (triple quadrupole mass spectrometer from Waters). Nitrogen was used as the nebulizer gas. Data acquisition was performed with a Waters-Micromass MassLynx-Openlynx data system.

Method V1005V1012

In addition to the general procedure VDR1: Reversed phase HPLC was carried out on a Waters X-bridge C18 column (3.5 μm, 4.6×100 mm) with a flow rate of 0.8 ml/min. Two mobile phases (mobile phase A: 100% 7 mM ammonium acetate; mobile phase B: 100% acetonitrile) were employed to run a gradient condition from 80% A and 20% B (hold for 0.5 minute) to 90% B in 4.5 minutes, 90% B for 4 minutes and reequilibrated with initial conditions for 3 minutes. An injection volume of 5 μl was used. Cone voltage was 20 V for positive and negative ionization mode. Mass spectra were acquired by scanning from 100 to 1000 in 0.4 seconds using an interscan delay of 0.3 seconds.

Method V1004V1012

In addition to the general procedure VDR1: Reversed phase HPLC was carried out on a Kromasil C18 column (3.5 μm, 4.6×100 mm) with a flow rate of 0.85 ml/min. Three mobile phases (mobile phase A: 100% 7 mM ammonium acetate; mobile phase B: 100% acetonitrile; mobile phase C: 0.2% formic acid+99.8% ultra-pure Water) were employed to run a gradient condition from 35% A, 30% B and 35% C (hold for 1 minute) to 100% B in 3 minutes, 100% B for 4.5 minutes and reequilibrated with initial conditions for 3 minutes. An injection volume of 5 μl was used. Cone voltage was 20 V for positive and negative ionization mode. Mass spectra were acquired by scanning from 100 to 1000 in 0.4 seconds using an interscan delay of 0.3 seconds.

Method V1010V1012

In addition to the general procedure VDR1: Reversed phase HPLC was carried out on a Waters Atlantis C18 column (5 μm, 3.9×100 mm) with a flow rate of 0.8 ml/min. Three mobile phases (mobile phase A: 100% 7 mM ammonium acetate; mobile phase B: 100% acetonitrile; mobile phase C: 0.2% formic acid+99.8% ultra-pure water) were employed to run a gradient condition from 50% A and 50% C (hold for 1.5 minute) to 10% A, 80% B and 10% C in 4.5 minutes, hold for 4 minutes and reequilibrated with initial conditions for 3 minutes. An injection volume of 5 μl was used. Cone voltage was 20 V for positive and negative ionization mode. Mass spectra were acquired by scanning from 100 to 1000 in 0.4 seconds using an interscan delay of 0.3 seconds.

Method V2002V2002+LCpos_court.olp

In addition to the general procedure VDR1: Reversed phase HPLC was carried out on a Kromasil C18 column (3.5 μm, 4.6×100 mm) with a flow rate of 0.8 ml/min. Three mobile phases (mobile phase A: 100% 7 mM ammonium acetate; mobile phase B: 100% acetonitrile; mobile phase C: 0.2% formic acid+99.8% ultra-pure water) were employed to run a gradient condition from 35% A, 30% B and 35% C (hold for 1 minute) to 100% B in 4 minutes, 100% B for 4 minutes and reequilibrated with initial conditions for 2 minutes. An injection volume of 10 μl was used. Cone voltage was 20 V for positive and negative ionization mode. Mass spectra were acquired by scanning from 100 to 1000 in 0.4 seconds using an interscan delay of 0.3 seconds.

Method V2003V2002

In addition to the general procedure VDR1: Reversed phase HPLC was carried out on a X-Bridge C18 column (3.5 μm, 4.6×100 mm) with a flow rate of 0.8 ml/min. Two mobile phases (mobile phase A: 100% 7 mM ammonium acetate; mobile phase B: 100% acetonitrile; were employed to run a gradient condition from 80% A, 20% B (hold for 0.5 minute) to 10% A, 90% B in 4.5 minutes, hold at 10% A and 90% B for 4 minutes and reequilibrated with initial conditions for 3 minutes. An injection volume of 10 μl was used. Cone voltage was 20 V for positive and negative ionization mode. Mass spectra were acquired by scanning from 100 to 1000 in 0.4 seconds using an interscan delay of 0.3 seconds.

Method V2012V2002

In addition to the general procedure VDR1: Reversed phase HPLC was carried out on a Waters Atlantis C18 column (5 μm, 3.9×100 mm) with a flow rate of 0.8 ml/min. Three mobile phases (mobile phase A: 100% 7 mM ammonium acetate; mobile phase B: 100% acetonitrile; mobile phase C: 0.2% formic acid+99.8% ultra-pure Water) were employed to run a gradient condition from 50% A, 0% B and 50% C (hold for 1.5 minutes) to 10% A, 80% B and 10% in 3.5 minutes, hold in these conditions for 4 minutes and reequilibrated with initial conditions for 3 minutes. An injection volume of 10 μl was used. Cone voltage was 20 V for positive and negative ionization mode. Mass spectra were acquired by scanning from 100 to 1000 in 0.4 seconds using an interscan delay of 0.3 seconds.

Method V2015V2007

In addition to the general procedure VDR1: Reversed phase HPLC was carried out on a Supelco Ascentis Express 018 column (2.7 μm, 3.0×50 mm) with a flow rate of 0.7 ml/min. Two mobile phases (mobile phase A: 100% 7 mM ammonium acetate; mobile phase B: 100% acetonitrile) were employed to run a gradient condition from 80% A and 20% B (hold for 0.5 minute) to 5% A and 95% B in 2.5 minutes, hold for 4.5 minutes and back to initial conditions in 1.5 minutes and hold for 1 min. An injection volume of 5 ml was used. Cone voltage was 20 V for positive and negative ionization mode. Mass spectra were acquired by scanning from 100 to 1000 in 0.4 seconds using an interscan delay of 0.3 seconds.

Method V3018V3001

In addition to the general procedure VDR2: Reversed phase UPLC was carried out on a Waters Acquity BEH (bridged ethylsiloxane/silica hybrid) C18 column (1.7 μm, 2.1×100 mm) with a flow rate of 0.343 ml/min. Two mobile phases (mobile phase A: 95% 7 mM ammonium acetate/5% acetonitrile; mobile phase B: 100% acetonitrile) were employed to run a gradient condition from 84.2% A and 15.8% B (hold for 0.49 minutes) to 10.5% A and 89.5% B in 2.18 minutes, hold for 1.94 min and back to the initial conditions in 0.73 min, hold for 0.73 minutes. An injection volume of 2 μl was used. Cone voltage was 20V for positive and negative ionization mode. Mass spectra were acquired by scanning from 100 to 1000 in 0.2 seconds using an interscan delay of 0.1 seconds.

Method V3014V3001

In addition to the general procedure VDR2: Reversed phase UPLC was carried out on a Waters HSS (High Strength Silica) T3 column (1.8 μm, 2.1×100 mm) with a flow rate of 0.35 ml/min. Two mobile phases (mobile phase A: 95% 7 mM ammonium acetate/5% acetonitrile; mobile phase B: 100% acetonitrile) were employed to run a gradient condition from 99% A (hold for 0.5 minutes) to 15% A and 85% B in 4.5 minutes, hold for 2 min and back to the initial conditions in 0.5 min, hold for 1.5 minutes. An injection volume of 2 □l was used. Cone voltage was 20 V for positive and negative ionization mode. Mass spectra were acquired by scanning from 100 to 1000 in 0.2 seconds using an interscan delay of 0.1 seconds.

Biological Activity of Compounds of Formula (I)

Description of Biological Assays

Reporter Assays for Assessment of TLR7 Activity (24 h)

The ability of compounds to activate human TLR7 was assessed in a cellular reporter assay using HEK293 cells transiently transfected with a TLR7 or TLR8 expression vector and NFκB-luc reporter construct. In one instance the TLR expression construct expresses the respective wild type sequence or a mutant sequence comprising a deletion in the second leucine-rich repeat (dIRR2) of the TLR. Such mutant TLR proteins have previously been shown to be more susceptible to agonist activation (U.S. Pat. No. 7,498,409).

Briefly, HEK293 cells were grown in culture medium (DMEM supplemented with 10%

FCS and 2 mM Glutamine). For transfection of cells in 10 cm dishes, cells were detached with Trypsin-EDTA, transfected with a mix of CMV-TLR7 or TLR8 plasmid (750 ng), NFκB-luc plasmid (375 ng) and a transfection reagent and incubated 24 hours or 48 hours respectively at 37° C. in a humidified 5% CO2 atmosphere. Transfected cells were then detached with Trypsin-EDTA, washed in PBS and resuspended in medium to a density of 1.67×105 cells/mL. Thirty microliters of cells were then dispensed into each well in 384-well plates, where 10 μL of compound in 4% DMSO was already present. Following 6 hours incubation at 37° C., 5% CO2, the luciferase activity was determined by adding 15 μl of Steady Lite Plus substrate (Perkin Elmer) to each well and readout performed on a ViewLux ultraHTS microplate imager (Perkin Elmer). Dose response curves were generated from measurements performed in quadruplicates. Lowest effective concentrations (LEC) values, defined as the concentration that induces an effect which is at least two fold above the standard deviation of the assay, were determined for each compound. Compound toxicity was determined in parallel using a similar dilution series of compound with 30 μL per well of cells transfected with the CMV-TLR7 construct alone (1.67×105 cells/mL), in 384-well plates. Cell viability was measured after 6 hours incubation at 37° C., 5% CO2 by adding 15 μL of ATP lite (Perkin Elmer) per well and reading on a ViewLux ultraHTS microplate imager (Perkin Elmer). Data was reported as 0050.

Measurement of Interferon Production in Human PBMC (PBMC-HUH7_EC50)

Activation of human TLR7 results in robust production of interferon by plasmacytoid dendritic cells present in human blood. The potential of compounds to induce interferon was evaluated by looking at the antiviral activity in the HCV replicon system upon incubation with conditioned media from peripheral blood mononuclear cells (PBMC). The HCV replicon assay is based on a bicistronic expression construct, as described by Lohmann et al. (Science (1999) 285: 110-113; Journal of Virology (2003) 77: 3007-15 3019) with modifications described by Krieger et al. (Journal of Virology (2001) 75: 4614-4624). The assay utilized the stably transfected cell line Huh-7 luc/neo harboring an RNA encoding a bicistronic expression construct comprising the wild type NS3-NS5B regions of HCV type 1b translated from an Internal Ribosome Entry Site (IRES) from encephalomyocarditis virus (EMCV), preceded by a reporter gene (Firefly-luciferase) and a selectable marker gene (neoR, neomycine phosphotransferase). The construct is flanked by 5' and 3' NTRs (non-translated regions) from HCV type 1b. Continued culture of the replicon cells in the presence of G418 (neoR) is dependent on the replication of the HCV RNA. The stably transfected replicon cells that replicate HCV RNA autonomously and to high levels, encoding inter alia luciferase, were used for profiling of the conditioned cell culture media. Briefly, PBMCs were prepared from buffy coats of at least two donors using a standard Ficoll centrifugation protocol. Isolated PBMCs were resuspended in RPMI medium supplemented with 10% human AB serum and 2×105 cells/well were dispensed into 384-well plates containing compounds (70 µL total volume). After overnight incubation, 10 µL of supernatant was transferred to 384-well plates containing 2.2×103 replicon cells/well in 30 µL (plated the day before). Following 24 hours of incubation, replication was measured by assaying luciferase activity using 40 µL/well Steady Lite Plus substrate (Perkin Elmer) and measured with ViewLux ultraHTS microplate imager (Perkin Elmer). The inhibitory activity of each compound on the Huh7-luc/neo cells were reported as EC50 values, defined as the compound concentration applied to the PBMCs resulting in a 50% reduction of luciferase activity which in turn indicates the degree of replication of the replicon RNA on transfer of a defined amount of PBMC culture medium. Recombinant interferon α-2a (Roferon-A) was used as a standard control compound. All compounds showed CC50 of >24 µM in the HEK 293 TOX assay described above.

Measurement of Interferon Production in Human PBMC (PBMC HEK-ISRE-luc LEC)

Activation of human TLR7 results in robust production of interferon by plasmacytoid dendritic cells present in human blood. The potential of compounds to induce interferon was evaluated by determination of interferon in the conditioned media from peripheral blood mononuclear cells (PBMC). The presence of interferon in the samples was determined, using an interferon reporter cell line stably expressing an interferon-stimulated responsive elements (ISRE)-luc reporter construct. The ISRE element with sequence GAAACTGAAACT is highly responsive to the STAT1-STAT2-IRF9 transcription factor, which becomes activated upon binding of IFN-I to the IFN receptor. Briefly, PBMCs were prepared from buffy coats of at least two donors using a standard Ficoll centrifugation protocol. Isolated PBMCs were resuspended in RPMI medium supplemented with 10% human AB serum and 2×105 cells/well were dispensed into 384-well plates containing compounds (70 µL total volume). After overnight incubation of the PBMCs with the compounds, 10 µL of supernatant was transferred to 384-well plates containing 5×103 HEK-ISRE-luc cells/well in 30 µL (plated the day before). Following 24 hours of incubation, activation of the ISRE elements was measured by assaying luciferase activity using 40 µL/well Steady Lite Plus substrate (Perkin Elmer) and measured with ViewLux ultraHTS microplate imager (Perkin Elmer). The stimulating activity of each compound on the HEK-ISRE-luc cells was reported as LEC. The LEC in turn indicates the degree of ISRE activation on transfer of a defined amount of PBMC culture medium. Recombinant interferon alfa-2a (Roferon-A) was used as a standard control compound.

The LEC values for the compounds in table 2 on HEK293 TLR8-NF☐B-luc and HEK293 NF☐B-luc where greater than the highest tested concentration (>10 µM for compound 6 and >25 µM for all other compounds).

TABLE 2

Biological activity of compounds of formula (I)

| # | STRUCTURE | TLR7-wt_LEC 24 h (µM) | TLR7-dIRR2_LEC 24 h (µM) | TLR7-wt_LEC 48 h (µM) | TLR7-dIRR2_LEC 48 h (µM) | PBMC-HUH7_EC50 (µM) | PBMC HEK-ISRE-luc (LEC; µM) |
|---|---|---|---|---|---|---|---|
| 1 | 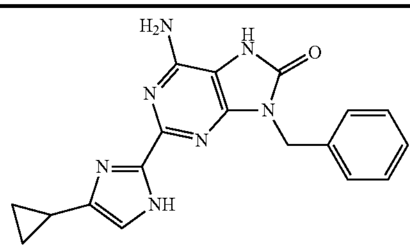 | | 0.33 | 8.25 | 0.18 | 0.081 | 0.064 |
| 2 | 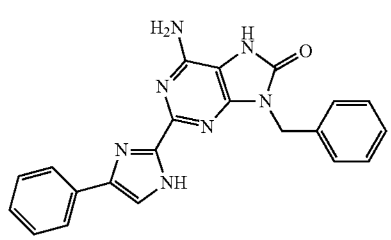 [SMILES: Nc1nc(-c2nc(-c3ccccc3)c[nH]2)nc2c1[nH]c(=O)n2Cc1ccccc1] | 4.72 | 1.2 | | | | 0.531 |

TABLE 2-continued
| | | Biological activity of compounds of formula (I) | | | | | |
|---|---|---|---|---|---|---|---|
| # | STRUCTURE | TLR7-wt_LEC 24 h (μM) | TLR7-dlRR2_LEC 24 h (μM) | TLR7-wt_LEC 48 h (μM) | TLR7-dlRR2_LEC 48 h (μM) | PBMC-HUH7_EC50 (μM) | PBMC HEK-ISRE-luc (LEC; μM) |
| 3 | 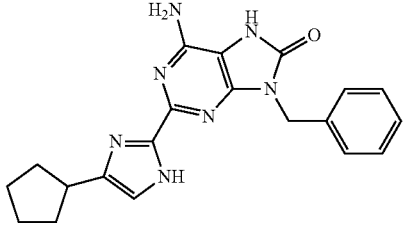 [SMILES: Nc1nc(-c2nc(C3CCCC3)c[nH]2)nc2c1[nH]c(=O)n2Cc1ccccc1] | >24.59 | 7.67 | | | 13.97 | |
| 4 | 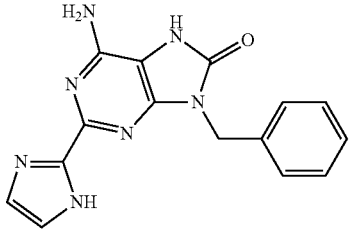 [SMILES: Nc1nc(-c2ncc[nH]2)nc2c1[nH]c(=O)n2Cc1ccccc1] | | 0.077 | 1.23 | 0.04 | 0.16 | 0.12 |
| 5 | 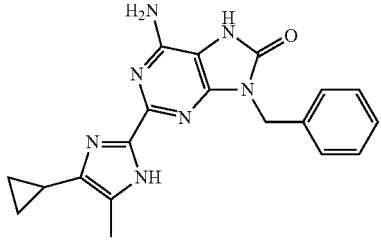 [SMILES: Cc1[nH]c(-c2nc(N)c3[nH]c(=O)n(Cc4ccccc4)c3n2)nc1C1CC1] | | 2.2 | 21.47 | 1.13 | 0.2 | 0.13 |
| 6 | 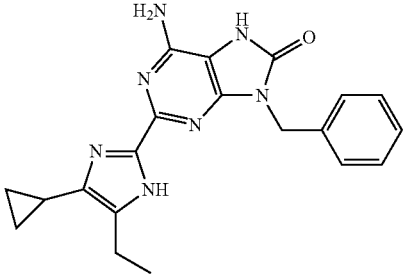 [SMILES: CCc1[nH]c(-c2nc(N)c3[nH]c(=O)n(Cc4ccccc4)c3n2)nc1C1CC1] | | 0.66 | 6.32 | 0.34 | 0.053 | 0.04 |
| 7 | 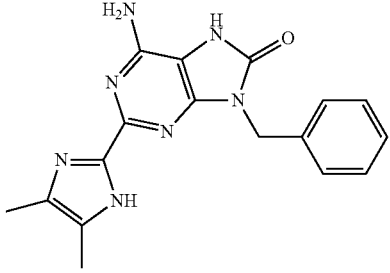 [SMILES: Cc1nc(-c2nc(N)c3[nH]c(=O)n(Cc4ccccc4)c3n2)[nH]c1C] | | >25 | 1.46 | 0.64 | 0.88 | |

TABLE 2-continued
Biological activity of compounds of formula (I)
| # | STRUCTURE | TLR7-wt_LEC 24 h (μM) | TLR7-dlRR2_LEC 24 h (μM) | TLR7-wt_LEC 48 h (μM) | TLR7-dlRR2_LEC 48 h (μM) | PBMC-HUH7_EC50 (μM) | PBMC HEK-ISRE-luc (LEC; μM) |
|---|---|---|---|---|---|---|---|
| 8 | 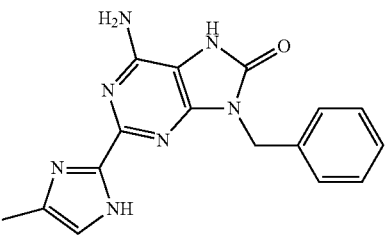 [SMILES: Cc1c[nH]c(-c2nc(N)c3[nH]c(=O)n(Cc4ccccc4)c3n2)n1] | | | 5.91 | 0.17 | 0.17 | 0.25 |
| 9 | 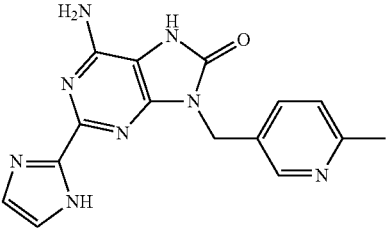 [SMILES: Cc1ccc(Cn2c(=O)[nH]c3c(N)nc(-c4ncc[nH]4)nc32)cn1] | | | 0.88 | 0.07 | 0.05 | 0.03 |
| 10 | 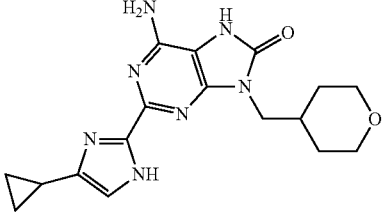 [SMILES: Nc1nc(-c2nc(C3CC3)c[nH]2)nc2c1[nH]c(=O)n2CC1CCOCC1] | 18.93 | >25 | 10.13 | 0.73 | 0.44 | |
| 11 | 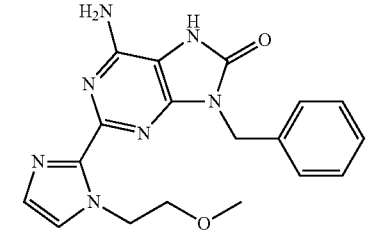 [SMILES: COCCn1ccnc1-c1nc(N)c2[nH]c(=O)n(Cc3ccccc3)c2n1] | | | 5.36 | 0.19 | 0.33 | 0.32 |
| 12 | 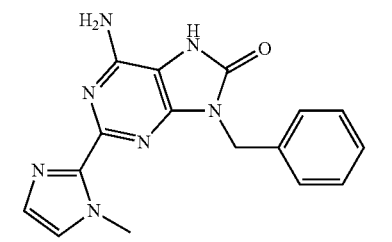 [SMILES: Cn1ccnc1-c1nc(N)c2[nH]c(=O)n(Cc3ccccc3)c2n1] | | | 8.08 | 0.3 | 0.59 | 0.34 |
| 15 | 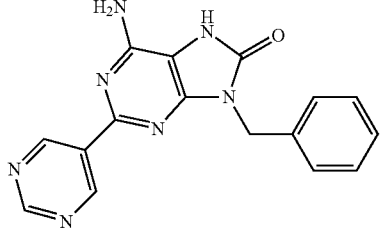 | >24.59 | 10.57 | >25 | 9.75 | 16.94 | |

TABLE 2-continued

Biological activity of compounds of formula (I)

| # | STRUCTURE | TLR7-wt_LEC 24 h (μM) | TLR7-dlRR2_LEC 24 h (μM) | TLR7-wt_LEC 48 h (μM) | TLR7-dlRR2_LEC 48 h (μM) | PBMC-HUH7_EC50 (μM) | PBMC HEK-ISRE-luc (LEC; μM) |
|---|---|---|---|---|---|---|---|
| 18 | 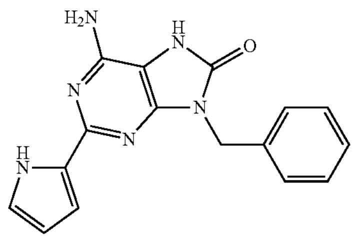 [SMILES: Nc1nc(-c2ccc[nH]2)nc2c1[nH]c(=O)n2Cc1ccccc1] | >24.59 | 3.23 | 20.31 | 3.81 | 2.58 | |
| 19 | 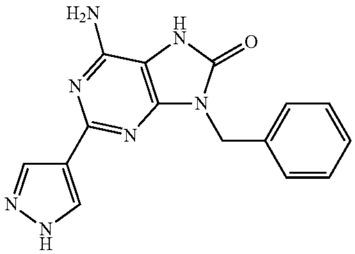 [SMILES: Nc1nc(-c2cn[nH]c2)nc2c1[nH]c(=O)n2Cc1ccccc1] | >24.59 | 13.31 | >25 | 16.6 | 12.36 | |
| 20 | 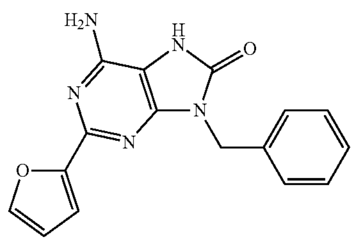 [SMILES: Nc1nc(-c2ccco2)nc2c1[nH]c(=O)n2Cc1ccccc1] | | 0.5 | 6.34 | 0.5 | 0.68 | |
| 23 | 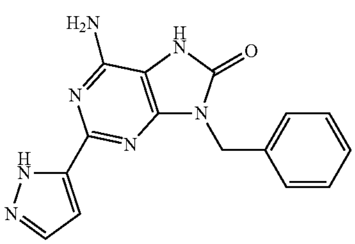 [SMILES: Nc1nc(-c2ccn[nH]2)nc2c1[nH]c(=O)n2Cc1ccccc1] | | 0.23 | 0.007 | 0.13 | 0.12 | |
| 24 | 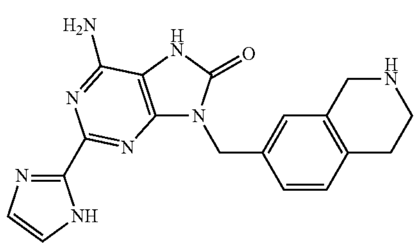 [SMILES: Nc1nc(-c2ncc[nH]2)nc2c1[nH]c(=O)n2Cc1ccc2c(c1)CNCC2] | | 1.81 | 0.11 | 0.046 | 0.03 | |
| 25 | 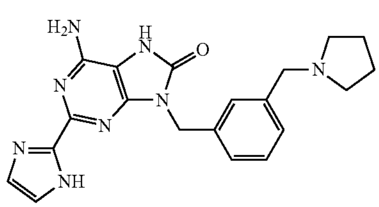 [SMILES: Nc1nc(-c2ncc[nH]2)nc2c1[nH]c(=O)n2Cc1cccc(CN2CCCC2)c1] | | 2.46 | 0.39 | 0.006 | 0.007 | |

TABLE 2-continued

Biological activity of compounds of formula (I)

| # | STRUCTURE | TLR7-wt_LEC 24 h (μM) | TLR7-dlRR2_LEC 24 h (μM) | TLR7-wt_LEC 48 h (μM) | TLR7-dlRR2_LEC 48 h (μM) | PBMC-HUH7_EC50 (μM) | PBMC HEK-ISRE-luc (LEC; μM) |
|---|---|---|---|---|---|---|---|
| 26 | 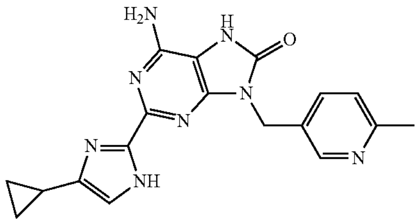 [SMILES: Cc1ccc(Cn2c(=O)[nH]c3c(N)nc(-c4nc(C5CC5)c[nH]4)nc32)cn1] | | | 2.42 | 0.21 | 0.005 | 0.006 |
| 27 | 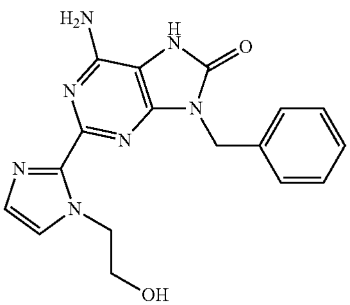 [SMILES: Nc1nc(-c2nccn2CCO)nc2c1[nH]c(=O)n2Cc1ccccc1] | | | 6.03 | 0.63 | 0.8 | 0.43 |
| 28 | 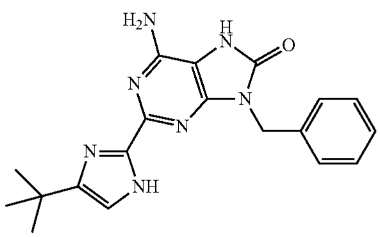 [SMILES: CC(C)(C)c1c[nH]c(-c2nc(N)c3[nH]c(=O)n(Cc4ccccc4)c3n2)n1] | | | >25 | 8.77 | >23.81 | >23.81 |
| 29 | 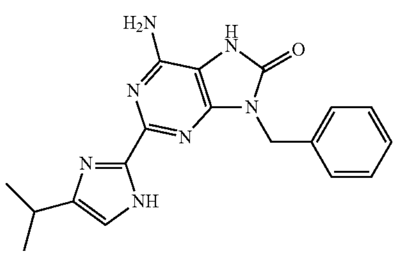 [SMILES: CC(C)c1c[nH]c(-c2nc(N)c3[nH]c(=O)n(Cc4ccccc4)c3n2)n1] | | | 1.58 | 1.66 | 0.82 | |
| 30 | 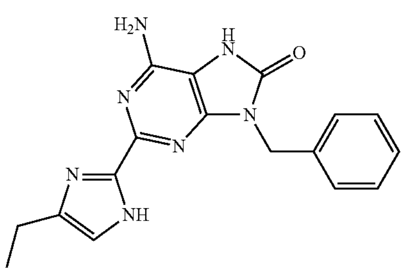 [SMILES: CCc1c[nH]c(-c2nc(N)c3[nH]c(=O)n(Cc4ccccc4)c3n2)n1] | | | 12.71 | 0.14 | 0.17 | 0.12 |
| 31 | 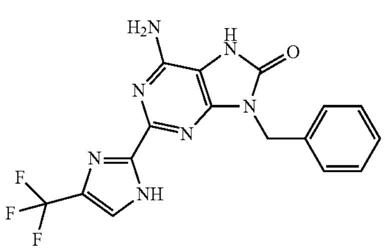 [SMILES: Nc1nc(-c2nc(C(F)(F)F)c[nH]2)nc2c1[nH]c(=O)n2Cc1ccccc1] | | | 23.33 | 0.51 | 1.3 | 2.2 |

TABLE 2-continued
Biological activity of compounds of formula (I)
| # | STRUCTURE | TLR7-wt_LEC 24 h (μM) | TLR7-dlRR2_LEC 24 h (μM) | TLR7-wt_LEC 48 h (μM) | TLR7-dlRR2_LEC 48 h (μM) | PBMC-HUH7_EC50 (μM) | PBMC HEK-ISRE-luc (LEC; μM) |
|---|---|---|---|---|---|---|---|
| 32 | 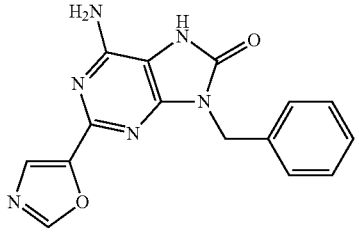 [SMILES: Nc1nc(-c2cnco2)nc2c1[nH]c(=O)n2Cc1ccccc1] | | | 6.5 | 0.97 | 1.51 | 0.97 |
| 33 | 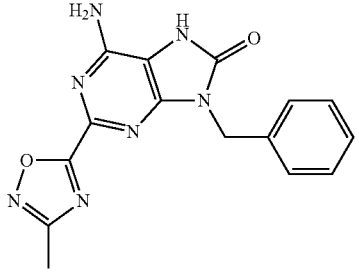 [SMILES: Cc1noc(-c2nc(N)c3[nH]c(=O)n(Cc4ccccc4)c3n2)n1] | | | 21.66 | 0.98 | 0.81 | 0.52 |
| 34 | 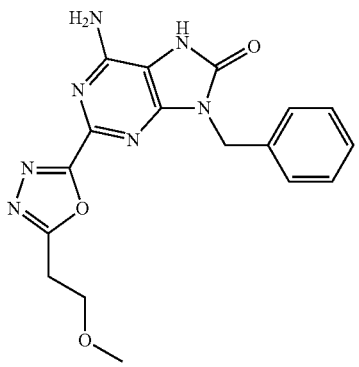 [SMILES: COCCc1nnc(-c2nc(N)c3[nH]c(=O)n(Cc4ccccc4)c3n2)o1] | | | >25 | 1.21 | 0.69 | 0.49 |
| 35 | 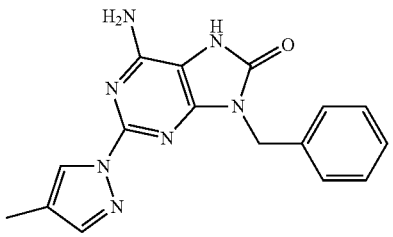 [SMILES: Cc1cnn(-c2nc(N)c3[nH]c(=O)n(Cc4ccccc4)c3n2)c1] | | | 0.36 | 0.033 | 0.17 | 0.10 |
| 36 | 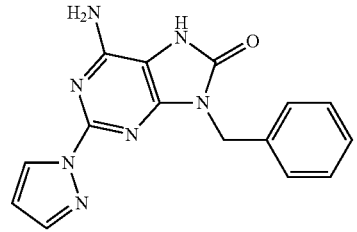 [SMILES: Nc1nc(-n2cccn2)nc2c1[nH]c(=O)n2Cc1ccccc1] | | | 0.22 | 0.017 | 0.047 | 0.033 |

TABLE 2-continued

Biological activity of compounds of formula (I)

| # | STRUCTURE | TLR7-wt_LEC 24 h (µM) | TLR7-dlRR2_LEC 24 h (µM) | TLR7-wt_LEC 48 h (µM) | TLR7-dlRR2_LEC 48 h (µM) | PBMC-HUH7_EC50 (µM) | PBMC HEK-ISRE-luc (LEC; µM) |
|---|---|---|---|---|---|---|---|
| 37 | (structure: 6-amino-2-(pyrazol-1-yl)-9-(3-(methoxycarbonyl)benzyl)-7,9-dihydro-8H-purin-8-one) | | | | | 0.05 | 0.01 |
| 38 | (structure: 6-amino-2-(pyrazol-1-yl)-9-(3-carboxybenzyl)-7,9-dihydro-8H-purin-8-one) | | | | | 0.38 | >25 |
| 39 | (structure: 6-amino-2-(pyrazol-1-yl)-9-(3-(hydroxymethyl)benzyl)-7,9-dihydro-8H-purin-8-one) | | | | | 0.05 | 0.01 |
| 40 | (structure: 6-amino-2-(pyrazol-1-yl)-9-(3-((diethoxyphosphoryl)methyl)benzyl)-7,9-dihydro-8H-purin-8-one) | | | | | 0.03 | 0.01 |
| 41 | (structure: 6-amino-2-(pyrazol-1-yl)-9-(3-(phosphonomethyl)benzyl)-7,9-dihydro-8H-purin-8-one · HCl) | | | | | 0.03 | 0.40 |

TABLE 2-continued

Biological activity of compounds of formula (I)

| # | STRUCTURE | TLR7-wt_LEC 24 h (μM) | TLR7-dlRR2_LEC 24 h (μM) | TLR7-wt_LEC 48 h (μM) | TLR7-dlRR2_LEC 48 h (μM) | PBMC-HUH7_EC50 (μM) | PBMC HEK-ISRE-luc (LEC; μM) |
|---|---|---|---|---|---|---|---|
| 42 | 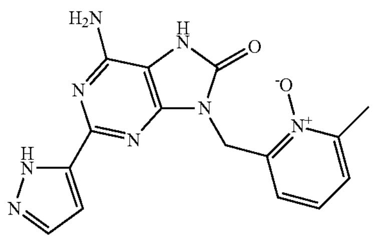 | | | | | 1.73 | 0.45 |
| 43 | 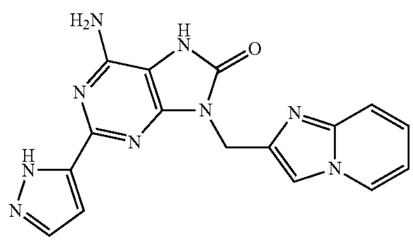 [SMILES: Nc1nc(-c2ccn[nH]2)nc2c1[nH]c(=O)n2Cc1cn2ccccc2n1] | | | | | 0.50 | 0.15 |
| 44 | 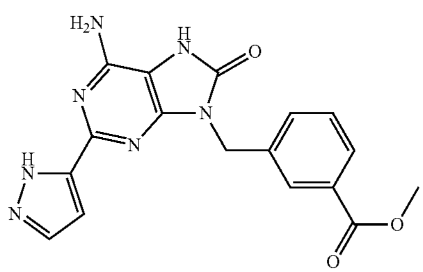 [SMILES: COC(=O)c1cccc(Cn2c(=O)[nH]c3c(N)nc(-c4ccn[nH]4)nc32)c1] | | | | | 0.10 | 0.04 |
| 45 | 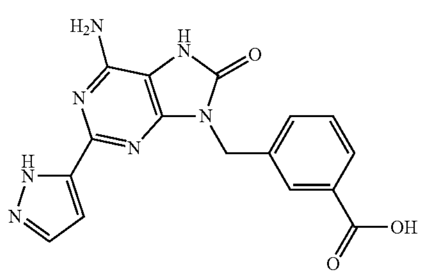 [SMILES: Nc1nc(-c2ccn[nH]2)nc2c1[nH]c(=O)n2Cc1cccc(C(=O)O)c1] | | | | | 0.58 | 1.37 |
| 46 | 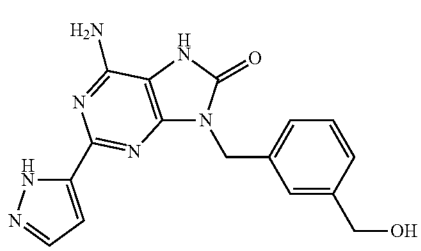 [SMILES: Nc1nc(-c2ccn[nH]2)nc2c1[nH]c(=O)n2Cc1cccc(CO)c1] | | | | | 0.21 | 0.03 |

TABLE 2-continued

Biological activity of compounds of formula (I)

| # | STRUCTURE | TLR7-wt_LEC 24 h (μM) | TLR7-dlRR2_LEC 24 h (μM) | TLR7-wt_LEC 48 h (μM) | TLR7-dlRR2_LEC 48 h (μM) | PBMC-HUH7_EC50 (μM) | PBMC HEK-ISRE-luc (LEC; μM) |
|---|---|---|---|---|---|---|---|
| 47 | 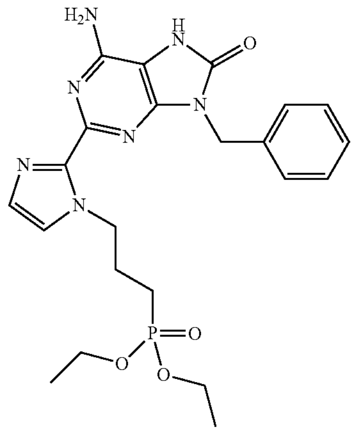 [SMILES: CCOP(=O)(CCCn1ccnc1-c1nc(N)c2[nH]c(=O)n(Cc3ccccc3)c2n1)OCC] | | | 14.12 | | | 1.64 |
| 48 | 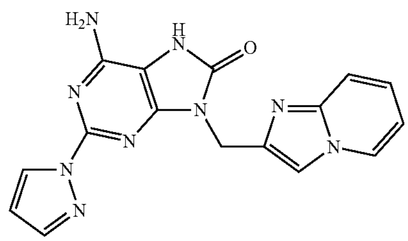 [SMILES: Nc1nc(-n2cccn2)nc2c1[nH]c(=O)n2Cc1cn2ccccc2n1] | | | 0.01 | | | 0.01 |
| 49 | 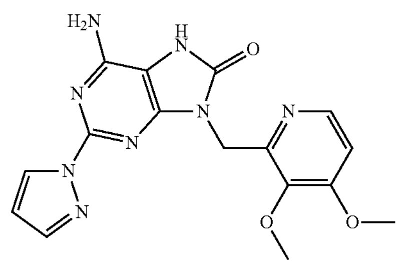 [SMILES: COc1ccnc(Cn2c(=O)[nH]c3c(N)nc(-n4cccn4)nc32)c1OC] | | | 0.31 | | | 0.06 |
| 50 | 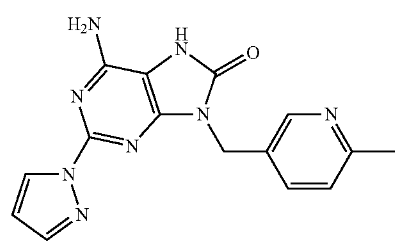 [SMILES: Cc1ccc(Cn2c(=O)[nH]c3c(N)nc(-n4cccn4)nc32)cn1] | | | 0.03 | | | 0.01 |
| 51 | 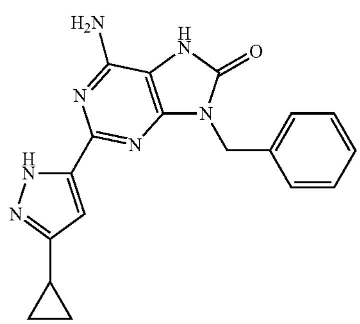 [SMILES: Nc1nc(-c2cc(C3CC3)n[nH]2)nc2c1[nH]c(=O)n2Cc1ccccc1] | | | 0.16 | | | 0.17 |

TABLE 2-continued

Biological activity of compounds of formula (I)

| # | STRUCTURE | TLR7-wt_LEC 24 h (μM) | TLR7-dlRR2_LEC 24 h (μM) | TLR7-wt_LEC 48 h (μM) | TLR7-dlRR2_LEC 48 h (μM) | PBMC-HUH7_EC50 (μM) | PBMC HEK-ISRE-luc (LEC; μM) |
|---|---|---|---|---|---|---|---|
| 52 | 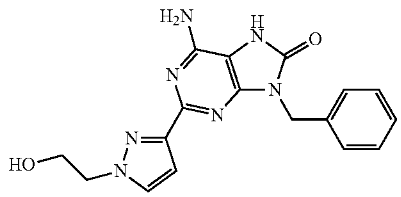 [SMILES: Nc1nc(-c2ccn(CCO)n2)nc2c1[nH]c(=O)n2Cc1ccccc1] | | | 4.42 | 0.41 | | 0.42 |
| 53 | 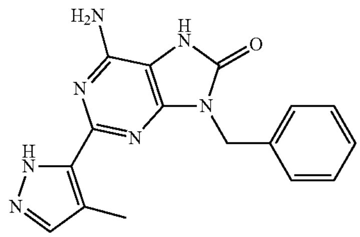 [SMILES: Cc1cn[nH]c1-c1nc(N)c2[nH]c(=O)n(Cc3ccccc3)c2n1] | | | 3.17 | 0.36 | 0.76 | |
| 54 | 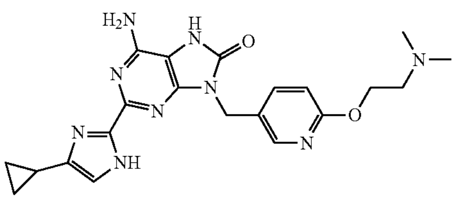 [SMILES: CN(C)CCOc1ccc(Cn2c(=O)[nH]c3c(N)nc(-c4nc(C5CC5)c[nH]4)nc32)cn1] | | | 16.1 | 5.65 | 0.05 | 0.07 |
| 55 | 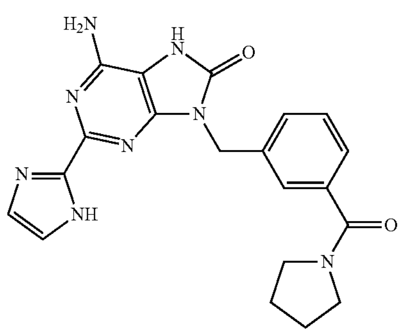 [SMILES: Nc1nc(-c2ncc[nH]2)nc2c1[nH]c(=O)n2Cc1cccc(C(=O)N2CCCC2)c1] | | | 4.11 | 0.06 | 1.27 | 1.16 |
| 57 | 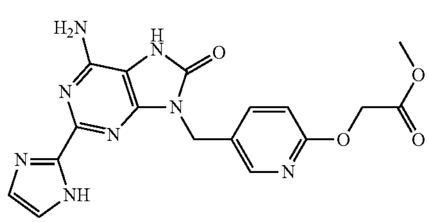 [SMILES: COC(=O)COc1ccc(Cn2c(=O)[nH]c3c(N)nc(-c4ncc[nH]4)nc32)cn1] | | | 0.44 | 0.06 | 1.21 | 1.38 |
| 58 | 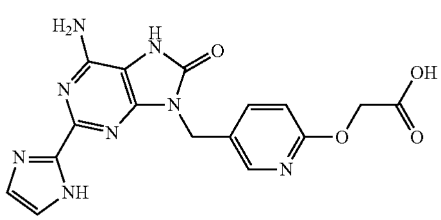 [SMILES: Nc1nc(-c2ncc[nH]2)nc2c1[nH]c(=O)n2Cc1ccc(OCC(=O)O)nc1] | | | 0.99 | 0.06 | 2.75 | 2.69 |

TABLE 2-continued

Biological activity of compounds of formula (I)

| # | STRUCTURE | TLR7-wt_LEC 24 h (μM) | TLR7-dlRR2_LEC 24 h (μM) | TLR7-wt_LEC 48 h (μM) | TLR7-dlRR2_LEC 48 h (μM) | PBMC-HUH7_EC50 (μM) | PBMC HEK-ISRE-luc (LEC; μM) |
|---|---|---|---|---|---|---|---|
| 60 | 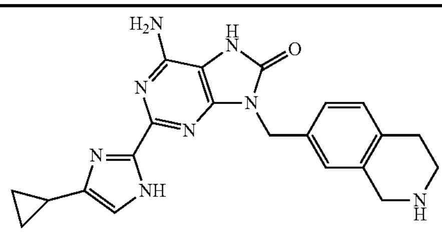 | | | >25 | 1.25 | 0.034 | 0.019 |
| 61 | 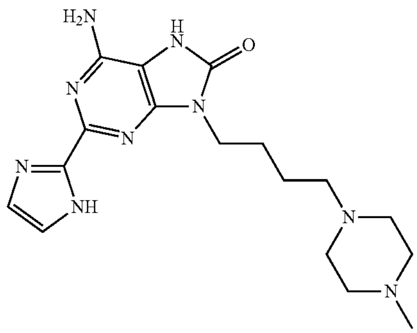 [SMILES: CN1CCN(CCCCn2c(=O)[nH]c3c(N)nc(-c4ncc[nH]4)nc32)CC1] | | | >25 | 9.73 | 1.34 | 0.95 |
| 62 | 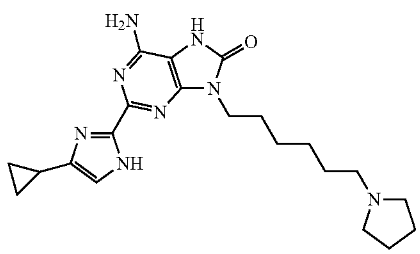 [SMILES: Nc1nc(-c2nc(C3CC3)c[nH]2)nc2c1[nH]c(=O)n2CCCCCCN1CCCC1] | | | 21.2 | >25 | 0.70 | 0.72 |
| 63 | 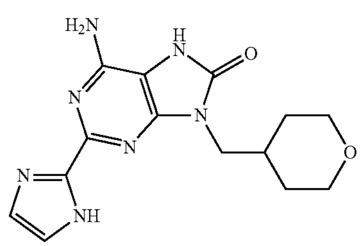 [SMILES: Nc1nc(-c2ncc[nH]2)nc2c1[nH]c(=O)n2CC1CCOCC1] | | | >25 | 2.58 | 5.72 | 4.39 |

All the compounds were tested in the reporter assays for assessment of TLR8 activity and showed LEC>17 μM.

The invention claimed is:

1. A compound of formula (I)

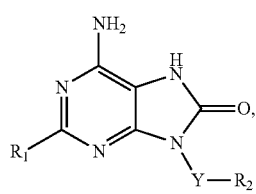

or a pharmaceutically acceptable salt, solvate or polymorph thereof, wherein Y is $C_{1-4}$ alkylene, $R_1$ is selected from the group consisting of imidazolyl, pyrimidyl, pyrrolyl, pyrazolyl, furyl, oxazolyl, oxadiazolyl, isoxazolyl, pyrazinyl and thiazolyl, wherein $R_1$ is optionally substituted by one or more substituents independently selected from the group consisting of hydroxyl, $C_{1-6}$ alkyl, $C_{1-4}$ alkoxy, trifluoromethyl, $C_{3-6}$ cycloalkyl, phenyl, halogen, hydroxyl-$C_{1-4}$ alkyl, $C_{1-4}$-alkoxy-$C_{1-4}$-alkyl- and $C_{1-4}$alkyl-diethoxyphosphoryl $R_2$ is selected from a group consisting of phenyl, naphtyl, anthracenyl and phenanthrenyl, wherein $R_2$ is optionally substituted by one or more substituents independently selected from the group consisting of hydroxyl, $C_{1-6}$ alkyl, $C_{1-4}$ alkoxy, trifluoromethyl, $CO_2R_3$, halogen, hydroxyl-$C_{1-4}$ alkyl-, $NR_6R_7$, $C(O)R_6$, $C(O)NR_6R_7$, $C_{1-4}$ alkyl-diethoxyphosphoryl or $C_{1-4}$ alkyl-phosphonic acid;

$R_3$ is selected from H and $C_{1-6}$ alkyl;

$R_6$ and $R_7$ are each independently selected from H, $C_{1-6}$ alkyl or $C_{1-4}$ alkoxy—after $C_{1-4}$ alkyl-diethoxyphosphoryl.

2. A pharmaceutical composition comprising a compound of formula (I) or a pharmaceutically acceptable salt, solvate or polymorph thereof according to claim 1, together with one or more pharmaceutically acceptable excipients, diluents or carriers.

3. A compound selected from the group consisting of:

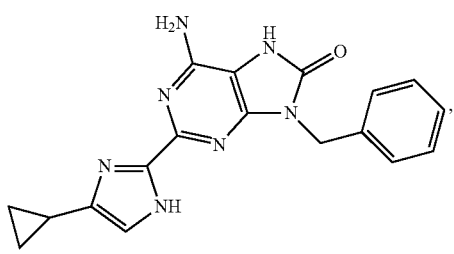

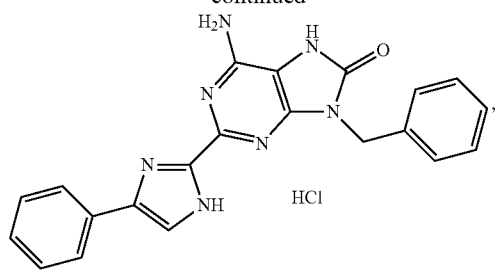

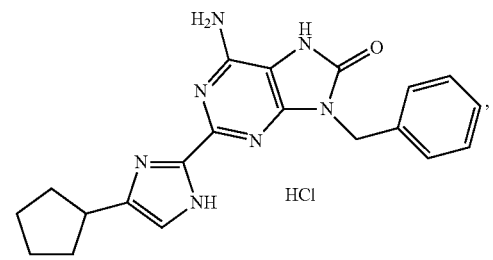

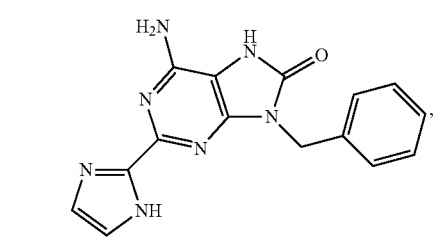 [SMILES: Nc1nc(-c2ncc[nH]2)nc2c1[nH]c(=O)n2CC1CCOCC1]

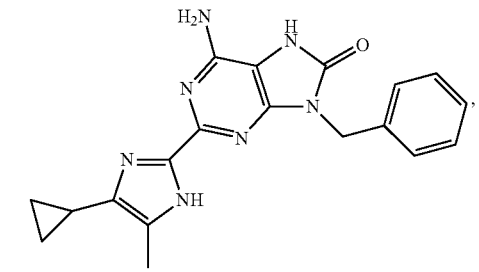

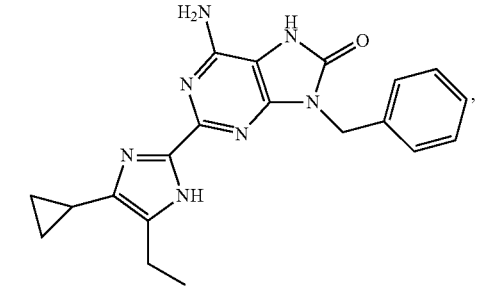

91
-continued
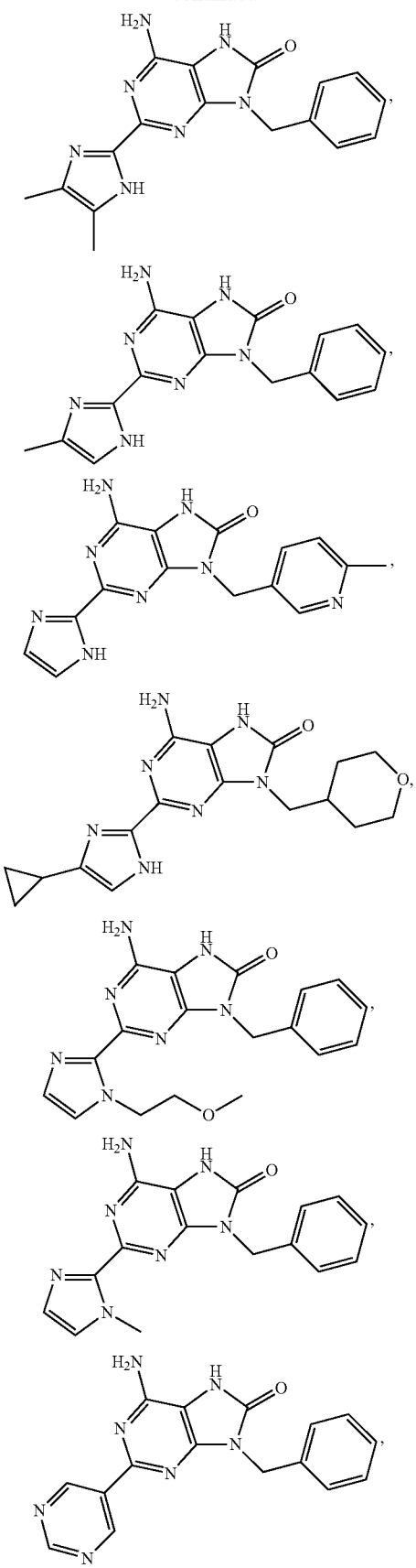
92
-continued
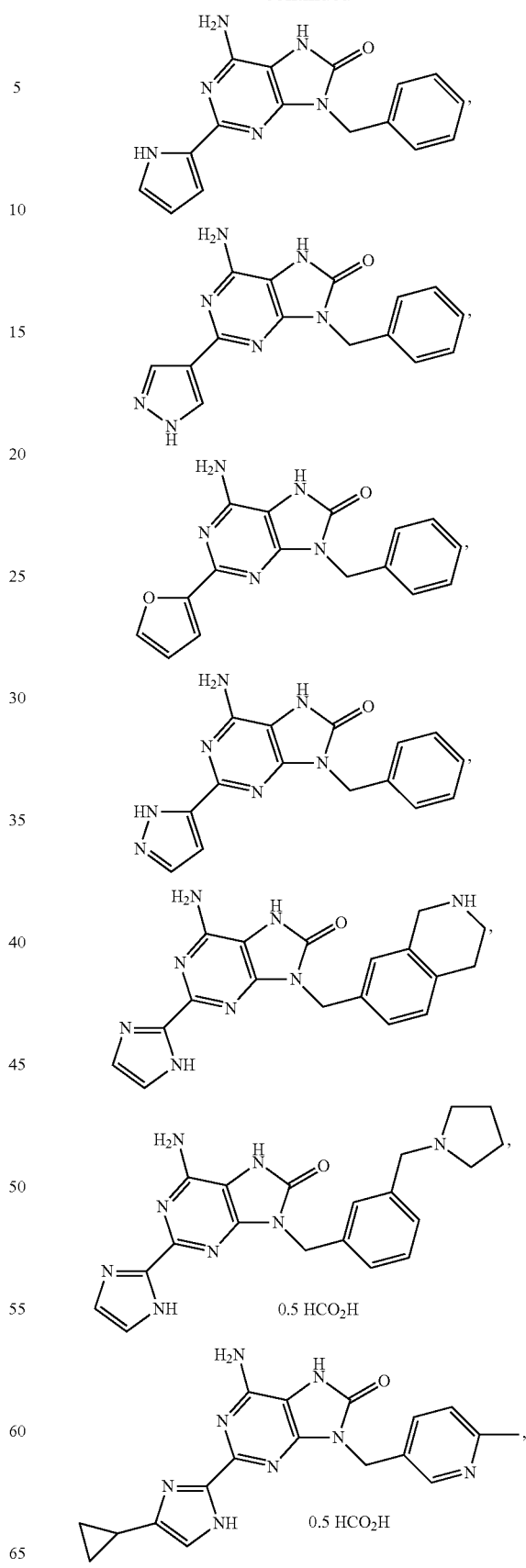

93
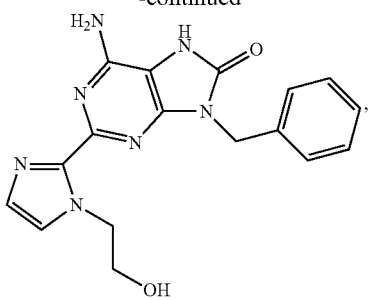
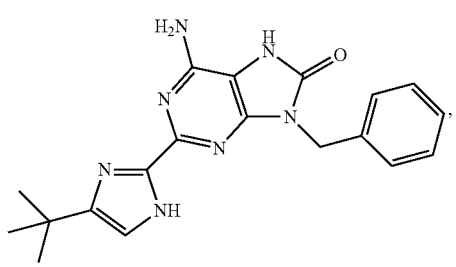
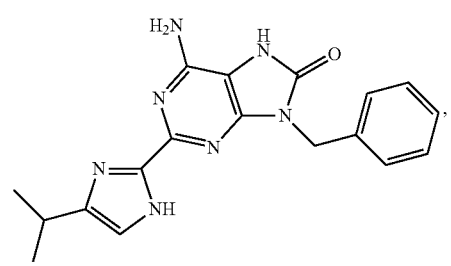
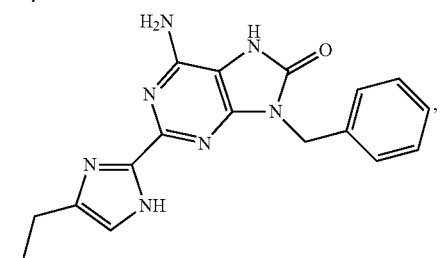
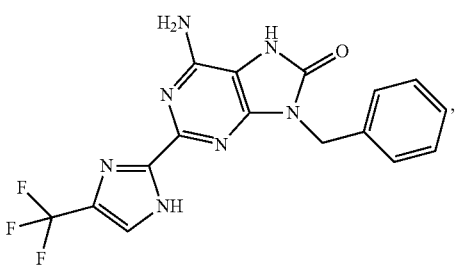
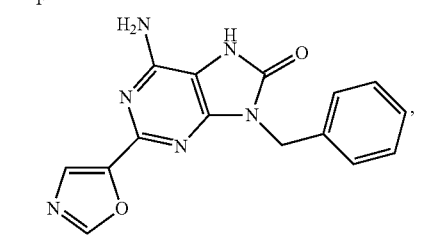
94
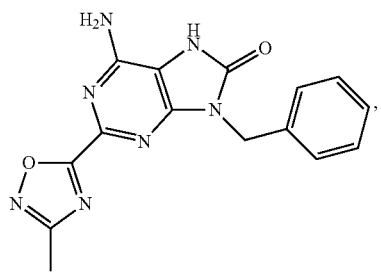
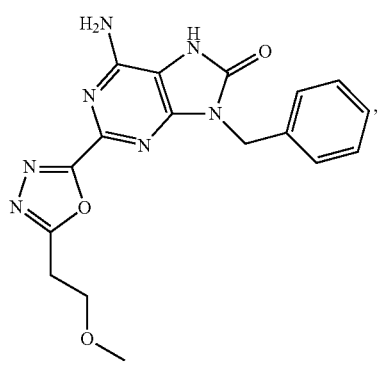
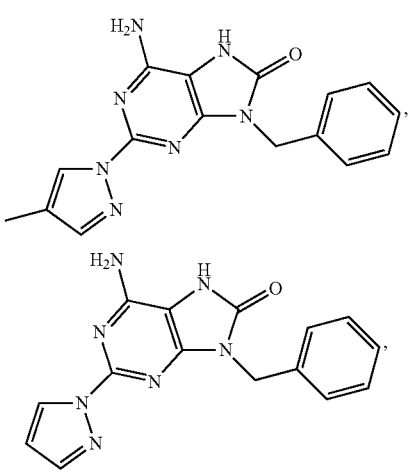
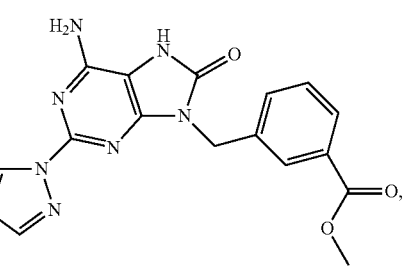
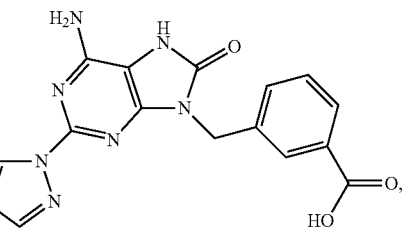

95
-continued
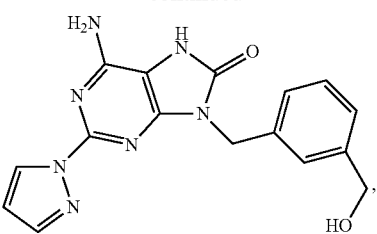
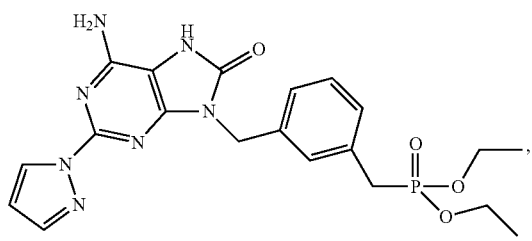
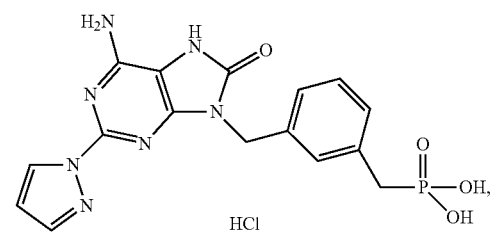
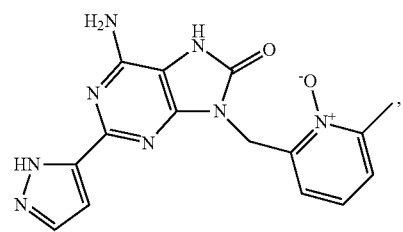
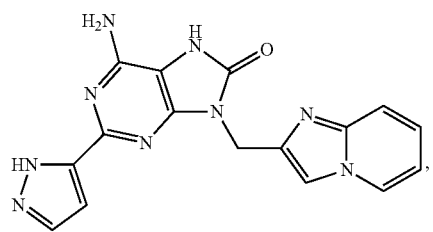
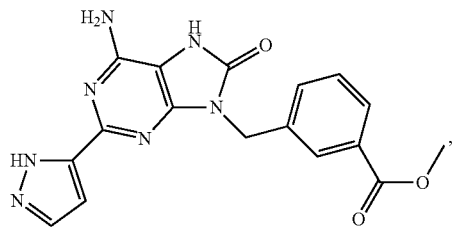
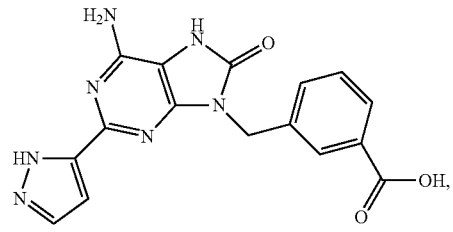
96
-continued
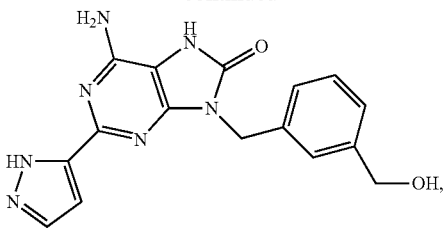
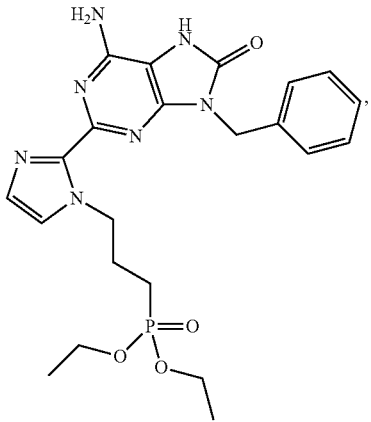
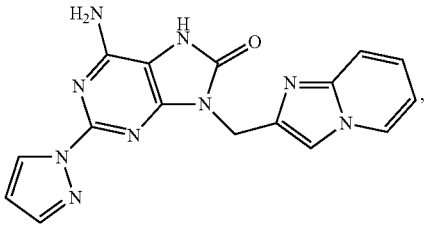
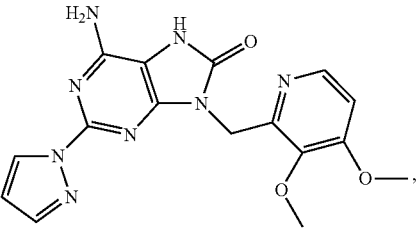
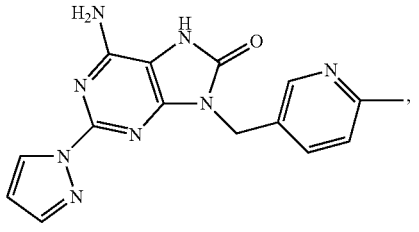
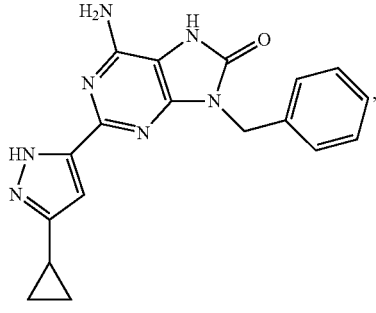

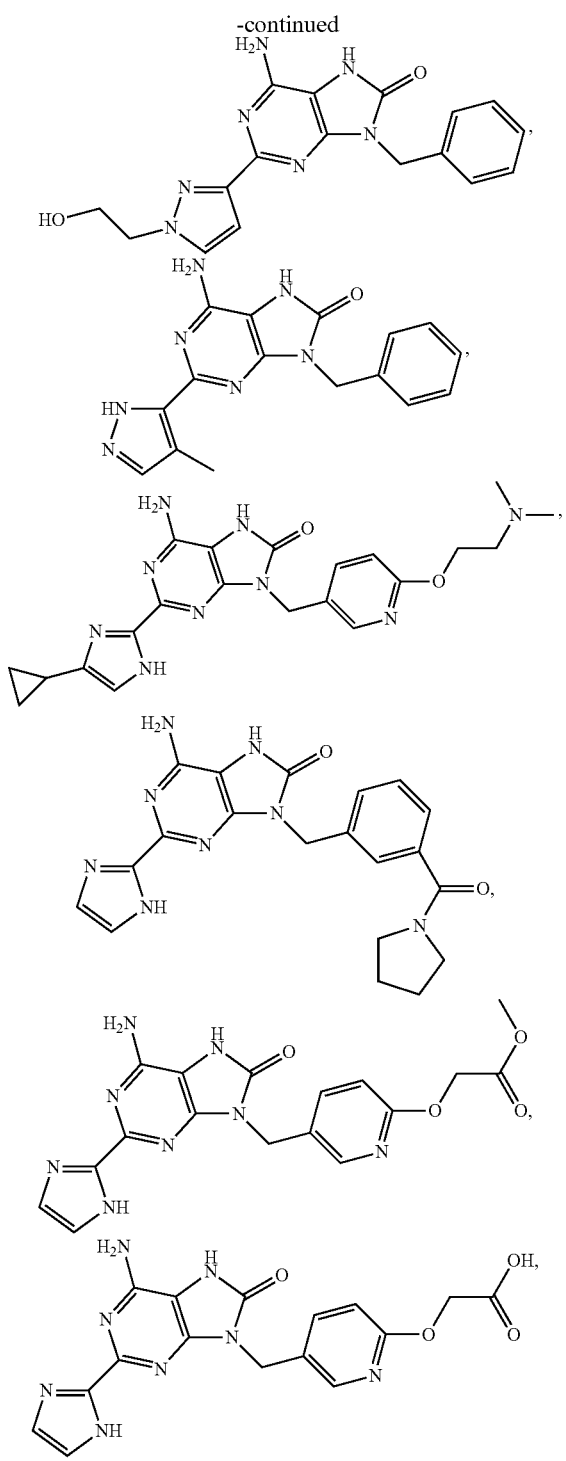
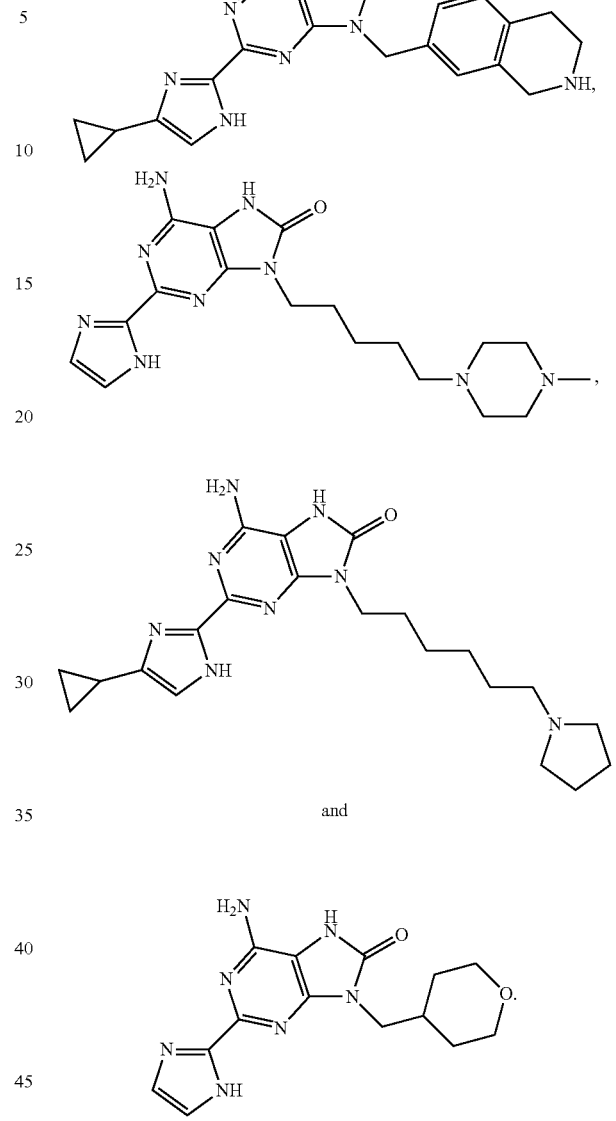
4. A pharmaceutical composition comprising a compound of formula (I) or a pharmaceutically acceptable salt, solvate or polymorph thereof according to claim 3, together with one or more pharmaceutically acceptable excipients, diluents or carriers.
* * * * *

UNITED STATES PATENT AND TRADEMARK OFFICE
CERTIFICATE OF CORRECTION

PATENT NO. : 9,556,176 B2
APPLICATION NO. : 14/357495
DATED : January 31, 2017
INVENTOR(S) : Jean-François Bonfanti et al.

Page 1 of 1

It is certified that error appears in the above-identified patent and that said Letters Patent is hereby corrected as shown below:

In the Specification

Please insert the following text in Column 1, following the paragraph entitled "CROSS-REFERENCE TO RELATED APPLICATIONS," which ends on Line 8:
--SEQUENCE LISTING
The instant application contains a Sequence Listing which has been submitted electronically in ASCII format and is hereby incorporated by reference in its entirety. Said ASCII copy, created on December 12, 2016, is named TIP0258USPCT_SL.txt and is 539 bytes in size.--

Please delete the following text in Column 68, Lines 16-19:
"reporter construct. The ISRE element of sequence GAAACTGAAACT is highly responsive to the STAT1-STAT2-IRF9 transcription factor, activated upon binding of IFN-I to the IFN receptor. Briefly, PBMCs"

Please insert the following text in Column 68, Lines 16-19:
--reporter construct. The ISRE element of sequence GAAACTGAAACT (SEQ ID NO: 1) is highly responsive to the STAT1-STAT2-IRF9 transcription factor, activated upon binding of IFN-I to the IFN receptor. Briefly, PBMCs--

Signed and Sealed this
Twentieth Day of August, 2019

Andrei Iancu
*Director of the United States Patent and Trademark Office*

SEQUENCE LISTING

<160> NUMBER OF SEQ ID NOS: 1

<210> SEQ ID NO 1
<211> LENGTH: 12
<212> TYPE: DNA
<213> ORGANISM: Artificial Sequence
<220> FEATURE:

```
<223> OTHER INFORMATION: Description of Artificial Sequence: Synthetic
      oligonucleotide

<400> SEQUENCE: 1
gaaactgaaa ct                                                        12
```